United States Patent
Behrens et al.

(10) Patent No.: US 6,649,641 B2
(45) Date of Patent: Nov. 18, 2003

(54) GLUCAGON ANTAGONISTS/INVERSE AGONISTS

(75) Inventors: Carsten Behrens, København (DK); Jesper Lau, Farum (DK); Peter Madsen, Bagsvaerd (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/996,025

(22) Filed: Nov. 16, 2001

(65) Prior Publication Data

US 2002/0187982 A1 Dec. 12, 2002

Related U.S. Application Data

(60) Provisional application No. 60/252,319, filed on Nov. 20, 2000.

(30) Foreign Application Priority Data

Nov. 1, 1970 (DK) .................................. PA 2000 01732

(51) Int. Cl.[7] ........................ A61K 31/41; C07D 257/04
(52) U.S. Cl. ........................................ 514/381; 548/253
(58) Field of Search ........................... 548/253; 514/381

(56) References Cited

U.S. PATENT DOCUMENTS

| 4,359,474 A | 11/1982 | Anderson et al. ............ 424/273 |
| 4,374,130 A | 2/1983 | Barcza ........................ 424/184 |
| 5,776,954 A | 7/1998 | de Laszlo et al. .......... 514/340 |
| 5,837,719 A | 11/1998 | de Laszlo et al. .......... 514/343 |
| 5,880,139 A | 3/1999 | Chang ........................ 514/326 |

FOREIGN PATENT DOCUMENTS

| WO | WO 94/14426 | 7/1994 |
| WO | WO 97/16442 | 5/1997 |
| WO | WO 98/04528 | 2/1998 |
| WO | WO 98/21957 | 5/1998 |
| WO | WO 98/22108 | 5/1998 |
| WO | WO 98/22109 | 5/1998 |
| WO | WO 98/24780 | 6/1998 |
| WO | WO 98/24782 | 6/1998 |
| WO | WO 99/01423 | 1/1999 |
| WO | WO 99/24404 | 5/1999 |
| WO | WO 99/32448 | 7/1999 |
| WO | WO 00/69810 | 6/2000 |
| WO | WO 00/39088 | 7/2000 |

OTHER PUBLICATIONS

C.L. Brand et al., Immunoneutralization of endogenous glucagons with Monoclonal glucagons antiody normalizes hyperglycaemia in moderately Streptozotocin–diabetic rats Diabetologia, vol. 37 pp. 985–993 (1994).
C.L. Brand et al [535] Diabetes 43, [suppl 1], 172A (1994).
C.L. Brand et al., Am J. Physiol. 269, E469–E477 (1995).
C.L. Brand et al [492] Diabetes 44 [suppl 1], 134A (1995).
C.L. Brand et al., "Evidence for a Major Role for Glucagon in Regu–lation of Plasma Glucose in Conscious, Nondiabetic, and Alloxan Induced Diabetic Rabbits", Diabetes vol. 45, pp. 1076–1083 (1996).
L.J. Jelinek et al., "Expression Cloning and Signaling Properties of the Rat Glucagon Receptor" Science vol. 259, pp. 1614–1616 (1993).
C.G. Unson et al., "Biological Activities of des–His$^1$[Glu$^9$] Glucagon Amide, A Glucagon Antagonist$^1$" Peptides, vol. 10 pp 1171–1177 (1998).
Post et al., "Mechanism of action of des–His$^1$[Glu$^9$]Glucagon Amide: A Peptide antagonist of the glucagons receptor system"Proc. Natl. Acad. Sci vol. 90 pp. 1662–1666 (1993).
Unson et al., Multiple–site Replacement Analogs of Glucagon The Journal of Biological Chemistry vol. 17, Issue of Apr. 29, pp. 12548–12551 (1994).
J.L. Collins et al., "CP–99, 711: A Non–Peptide Glucagon Receptor Antagonist"Bioorganic & Med.Chem. Ltr. vol. 2,No. 9, pp. 915–918 (1992).
Azizeh et al.,"[des His$^1$, des Phe$^6$, Glu$^9$]Glucagon Amide: A newly Designed "Pure" Glucagon Antagonist", Bioorganic & Med.Chem.Ltr, vol. 5, No. 16 pp. 1849–1852 (1995).
P. Madsen et al., Discovery and Structure–Activity Relationship of The First Non–Peptide Competitive Human Glucagon Receptor Antagonists J. Med.Chem. vol. 41, pp. 5150–5157 (1998).

*Primary Examiner*—Joseph K. McKane
*Assistant Examiner*—Rebecca Anderson
(74) *Attorney, Agent, or Firm*—Reza Green, Esq.; Richard W. Bork, Esq.; Marc A. Began, Esq.

(57) ABSTRACT

A novel class of compounds, which act to antagonize the action of the glucagon hormone on the glucagon receptor. Owing to their antagonizing effect of the glucagon receptor the compounds may be suitable for the treatment and/or prevention of any diseases and disorders, wherein a glucagon antagonistic action is beneficial, such as hyperglycemia, Type 1 diabetes, Type 2 diabetes, disorders of the lipid metabolism and obesity.

55 Claims, No Drawings

GLUCAGON ANTAGONISTS/INVERSE AGONISTS

CROSS-REFERENCE TO RELATED APPLICATIONS

This application claims priority under 35 U.S.C. 119 of Danish application PA 2000 01732, filed Nov. 17, 2000 and of U.S. application Ser. No. 60/252,319, filed Nov. 20, 2000, the contents of both of which are fully incorporated herein by reference.

FIELD OF THE INVENTION

The present invention relates to agents that act to antagonize the action of the glucagon peptide hormone on the glucagon receptor. More particularly, it relates to glucagon antagonists or inverse agonists.

BACKGROUND OF THE INVENTION

Glucagon is a key hormonal agent that, in co-operation with insulin, mediates homeostatic regulation of the amount of glucose in the blood. Glucagon primarily acts by stimulating certain cells (mostly liver cells) to release glucose when blood glucose levels fall. The action of glucagon is opposite to that of insulin, which stimulates cells to take up and store glucose whenever blood glucose levels rise. Both glucagon and insulin are peptide hormones.

Glucagon is produced in the alpha islet cells of the pancreas and insulin in the beta islet cells. Diabetes mellitus is a common disorder of glucose metabolism. The disease is characterized by hyperglycemia and may be classified as Type 1 diabetes, the insulin-dependent form, or Type 2 diabetes, which is non-insulin-dependent in character. Subjects with Type 1 diabetes are hyperglycemic and hypoinsulinemic, and the conventional treatment for this form of the disease is to provide insulin. However, in some patients with Type 1 or Type 2 diabetes, absolute or relative elevated glucagon levels have been shown to contribute to the hyperglycemic state. Both in healthy control animals as well as in animal models of Type 1 and Type 2 diabetes, removal of circulating glucagon with selective and specific antibodies has resulted in reduction of the glycemic level (Brand et al., Diabetologia 37, 985 (1994); Diabetes 43, [suppl 1], 172A (1994); Am. J. Physiol. 269, E469-E477 (1995); Diabetes 44 [suppl 1], 134A (1995); Diabetes 45, 1076 (1996)). These studies suggest that glucagon suppression or an action that antagonizes glucagon could be a useful adjunct to conventional treatment of hyperglycemia in diabetic patients. The action of glucagon can be suppressed by providing an antagonist or an inverse agonist, ie substances that inhibit or prevent glucagon-induced responses. The antagonist can be peptidic or non-peptidic in nature.

Native glucagon is a 29 amino acid peptide having the sequence:

His-Ser-Glu-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-OH

Glucagon exerts its action by binding to and activating its receptor, which is part of the Glucagon-Secretin branch of the 7-transmembrane G-protein coupled receptor family (Jelinek et al., Science 259, 1614, (1993)). The receptor functions by activating the adenylyl cyclase second messenger system and the result is an increase in cAMP levels.

Several publications disclose peptides that are stated to act as glucagon antagonists. Probably, the most thoroughly characterized antagonist is DesHis[1][Glu[9]]-glucagon amide (Unson et al., Peptides 10, 1171 (1989); Post et al., Proc. Natl. Acad. Sci. USA 90, 1662 (1993)). Other antagonists are DesHis[1],Phe[6][Glu[9]]-glucagon amide (Azizh et al., Bioorganic & Medicinal Chem. Lett. 16, 1849 (1995)) and NLeu[9],Ala[11,16]-glucagon amide (Unson et al., J. Biol. Chem. 269 (17), 12548 (1994)).

Peptide antagonists of peptide hormones are often quite potent. However, they are generally known not to be orally available because of degradation by physiological enzymes, and poor distribution in vivo. Therefore, orally available non-peptide antagonists of peptide hormones are generally preferred. Among the non-peptide glucagon antagonists, a quinoxaline derivative, (2-styryl-3-[3-(dimethylamino)-propylmethylamino]-6,7-dichloroquinoxaline was found to displace glucagon from the rat liver receptor (Collins, J. L. et al., Bioorganic and Medicinal Chemistry Letters 2(9): 915–918 (1992)). WO 94/14426 (The Wellcome Foundation Limited) discloses use of skyrin, a natural product comprising a pair of linked 9,10-anthracenedione groups, and its synthetic analogues, as glucagon antagonists. U.S. Pat. No. 4,359,474 (Sandoz) discloses the glucagon inhibiting properties of 1-phenyl pyrazole derivatives. U.S. Pat. No. 4,374,130 (Sandoz) discloses substituted disilacyclohexanes as glucagon inhibiting agents. WO 98/04528 (Bayer Corporation) discloses substituted pyridines and biphenyls as glucagon antagonists. U.S. Pat. No. 5,776,954 (Merck & Co., Inc.) discloses substituted pyridyl pyrroles as glucagon antagonists and WO 98/21957, WO 98/22108, WO 98/22109 and U.S. Pat. No. 5,880,139 (Merck & Co., Inc.) disclose 2,4-diaryl-5-pyridyl-imidazoles as glucagon antagonists. Furthermore, WO 97/16442 and U.S. Pat. No. 5,837,719 (Merck & Co., Inc.) disclose 2,5-substituted aryl pyrroles as glucagon antagonists. WO 98/24780, WO 98/24782, WO 99/24404 and WO 99/32448 (Amgen Inc.) disclose substituted pyrimidinone and pyridone compounds and substituted pyrimidine compounds, respectively, which are stated to possess glucagon antagonistic activity. Madsen et al. (J. Med. Chem. 1998 (41) 5151–7) discloses a series of 2-(benzimidazol-2-ylthio)-1-(3,4-dihydroxyphenyl)-1-ethanones as competitive human glucagon receptor antagonists. WO 99/01423 and WO 00/39088 (Novo Nordisk A/S) disclose different series of alkylidene hydrazides as glucagon antagonists/inverse agonists. These known glucagon antagonists differ structurally from the present compounds.

These known glucagon antagonists differ structurally from the present compounds.

DEFINITIONS

The following is a detailed definition of the terms used to describe the compounds of the invention:

"Halogen" designates an atom selected from the group consisting of F, Cl, Br and I.

The term "$C_{1-6}$-alkyl" as used herein represents a saturated, branched or straight hydrocarbon group having from 1 to 6 carbon atoms. Representative examples include, but are not limited to, methyl, ethyl, n-propyl, isopropyl, butyl, isobutyl, sec-butyl, tert-butyl, n-pentyl, isopentyl, neopentyl, tert-pentyl, n-hexyl, isohexyl and the like.

The term "$C_{2-6}$-alkenyl" as used herein represents a branched or straight hydrocarbon group having from 2 to 6 carbon atoms and at least one double bond. Examples of such groups include, but are not limited to, vinyl, 1-propenyl, 2-propenyl, iso-propenyl, 1,3-butadienyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 2,4-hexadienyl, 5-hexenyl and the like.

The term "C$_{2-6}$-alkynyl" as used herein represents a branched or straight hydrocarbon group having from 2 to 6 carbon atoms and at least one triple bond. Examples of such groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 2,4-hexadiynyl and the like.

The term "C$_{1-6}$-alkoxy" as used herein refers to the radical —O—C$_{1-6}$-alkyl, wherein C$_{1-6}$-alkyl is as defined above. Representative examples are methoxy, ethoxy, n-propoxy, isopropoxy, butoxy, sec-butoxy, tert-butoxy, pentoxy, isopentoxy, hexoxy, isohexoxy and the like.

The term "C$_{3-8}$-cycloalkyl" as used herein represents a saturated, carbocyclic group having from 3 to 8 carbon atoms. Representative examples are cyclopropyl, cyclobutyl, cyclopentyl, cyclohexyl, cycloheptyl, cyclooctyl and the like.

The term "C$_{4-8}$-cycloalkenyl" as used herein represents a non-aromatic, carbocyclic group having from 4 to 8 carbon atoms containing one or two double bonds. Representative examples are 1-cyclopentenyl, 2-cyclopentenyl, 3-cyclopentenyl, 1-cyclohexenyl, 2-cyclohexenyl, 3-cyclohexenyl, 2-cycloheptenyl, 3-cycloheptenyl, 2-cyclooctenyl, 1,4-cyclooctadienyl and the like.

The term "heterocyclyl" as used herein represents a non-aromatic 3 to 10 membered ring containing one or more heteroatoms selected from nitrogen, oxygen and sulfur and optionally containing one or two double bonds. Representative examples are pyrrolidinyl, piperidyl, piperazinyl, morpholinyl, thiomorpholinyl, aziridinyl, tetrahydrofuranyl and the like.

The term "aryl" as used herein is intended to include carbocyclic, aromatic ring systems such as 6 membered monocyclic and 9 to 14 membered bi- and tricyclic, carbocyclic, aromatic ring systems. Representative examples are phenyl, biphenylyl, naphthyl, anthracenyl, phenanthrenyl, fluorenyl, indenyl, azulenyl and the like. Aryl is also intended to include the partially hydrogenated derivatives of the ring systems enumerated above. Non-limiting examples of such partially hydrogenated derivatives are 1,2,3,4-tetrahydronaphthyl, 1,4-dihydronaphthyl and the like.

The term "arylene" as used herein is intended to include divalent, carbocyclic, aromatic ring systems such as 6 membered monocyclic and 9 to 14 membered bi- and tricyclic, divalent, carbocyclic, aromatic ring systems. Representative examples are phenylene, biphenylylene, naphthylene, anthracenylene, phenanthrenylene, fluorenylene, indenylene, azulenylene and the like. Arylene is also intended to include the partially hydrogenated derivatives of the ring systems enumerated above. Non-limiting examples of such partially hydrogenated derivatives are 1,2,3,4-tetrahydronaphthylene, 1,4-dihydronaphthylene and the like.

The term "aryloxy" as used herein denotes a group —O-aryl, wherein aryl is as defined above.

The term "aroyl" as used herein denotes a group —C(O)-aryl, wherein aryl is as defined above.

The term "heteroaryl" as used herein is intended to include aromatic, heterocyclic ring systems containing one or more heteroatoms selected from nitrogen, oxygen and sulfur such as 5 to 7 membered monocyclic and 8 to 14 membered bi- and tricyclic aromatic, heterocyclic ring systems containing one or more heteroatoms selected from nitrogen, oxygen and sulfur. Representative examples are furyl, thienyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuryl, benzothienyl, indazolyl, benzimidazolyl, benzthiazolyl, benzisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl and the like. Heteroaryl is also intended to include the partially hydrogenated derivatives of the ring systems enumerated above. Non-limiting examples of such partially hydrogenated derivatives are 2,3-dihydrobenzofuranyl, pyrrolinyl, pyrazolinyl, indolinyl, oxazolidinyl, oxazolinyl, oxazepinyl and the like.

"Aryl-C$_{1-6}$-alkyl", "heteroaryl-C$_{1-6}$-alkyl", "aryl-C$_{2-6}$-alkenyl" etc. mean C$_{1-6}$-alkyl or C$_{2-6}$-alkenyl as defined above, substituted by an aryl or heteroaryl as defined above, for example:

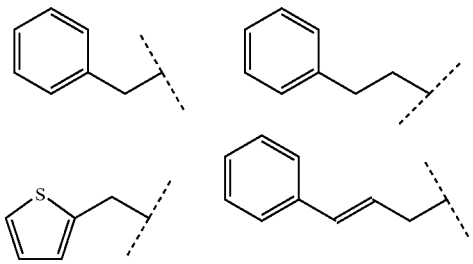

The term "optionally substituted" as used herein means that the groups in question are either unsubstituted or substituted with one or more of the substituents specified. When the groups in question are substituted with more than one substituent the substituents may be the same or different.

Certain of the above defined terms may occur more than once in the structural formulae, and upon such occurrence each term shall be defined independently of the other.

Furthermore, when using the terms "independently are" and "independently selected from" it should be understood that the groups in question may be the same or different.

DESCRIPTION OF THE INVENTION

The present invention is based on the unexpected observation that the compounds of the general formula (I) disclosed below show a high binding affinity for the glucagon receptor and antagonize the action of glucagon.

Accordingly, the invention is concerned with compounds of the general formula (I):

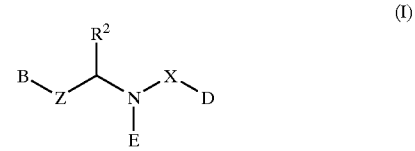

(I)

wherein

R$^2$ is hydrogen or C$_{1-6}$-alkyl,

B is

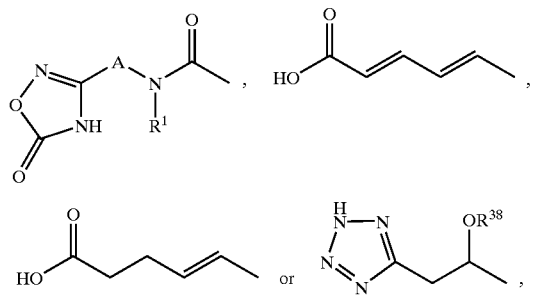

R³⁸ is hydrogen, —S(=O)₂—C₁₋₆-alkyl or —C(=O)—C₁₋₆-alkyl,

A is a valence bond, —(CR³R⁴)—, or —(CR³R⁴)(CR⁵R⁶)—,

R¹, R³, R⁴, R⁵ and R⁶ independently are hydrogen or C₁₋₆-alkyl,

Z is arylene or a divalent radical derived from a 5 or 6 membered heteroaromatic ring containing 1 or 2 heteroatoms selected from nitrogen, oxygen and sulfur, which may optionally be substituted with one or two groups R⁷ and R⁸ selected from halogen, —CN, —CF₃, —OCF₃, —NO₂, —OR⁹, —NR⁹R¹⁰ and C₁₋₆-alkyl, wherein R⁹ and R¹⁰ independently are hydrogen or C₁₋₆-alkyl, X is

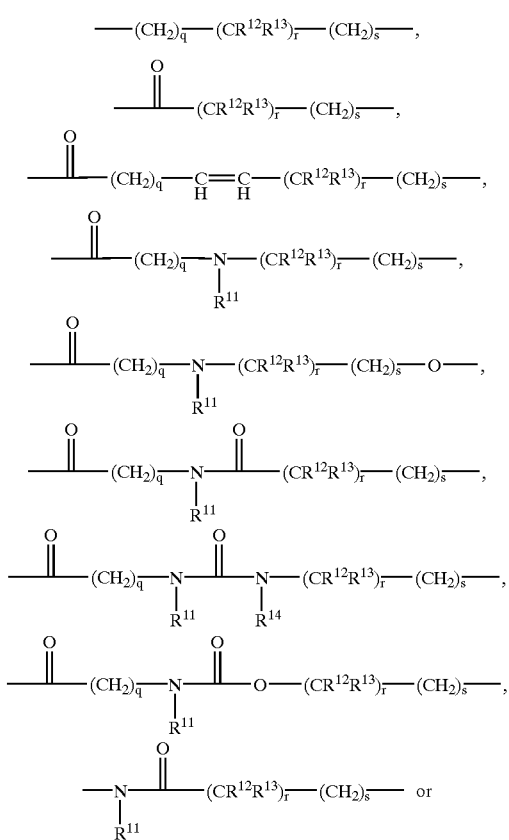

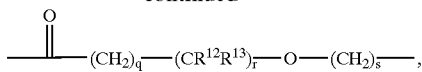

wherein
r is 0 or 1,
q and s independently are 0, 1, 2 or 3,
R¹¹, R¹², R¹³ and R¹⁴ independently are hydrogen or C₁₋₆-alkyl,
D is

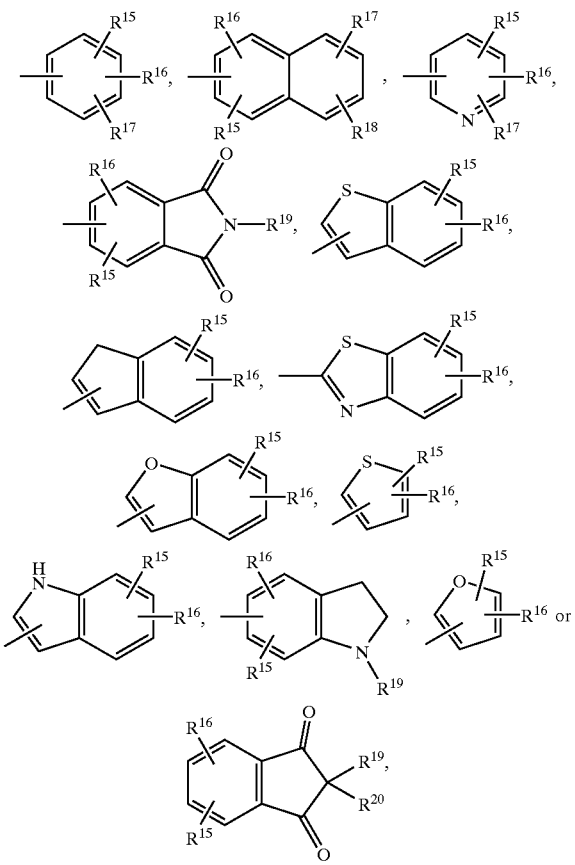

wherein
R¹⁵, R¹⁶, R¹⁷ and R¹⁸ independently are
hydrogen, halogen, —CN, —CH₂CN, —CHF₂, —CF₃, —OCF₃, —OCHF₂, —OCH₂CF₃, —OCF₂CHF₂, —S(O)₂CF₃, —SCF₃, —NO₂, —OR²¹, —NR²¹R²², —SR²¹, NR²¹S(O)₂R²², —S(O)₂NR²¹R²², S(O)NR²¹R²², —S(O)R²¹, —S(O)₂R²¹, —C(O)NR²¹R²², —OC(O)NR²¹R²², —NR²¹C(O)R²², —CH₂C(O)NR²¹R²², —OCH₂C(O)NR²¹R²², —CH₂OR²¹, —CH₂NR²¹R²², —OC(O)R²¹, —C(O)R²¹ or —C(O)OR²¹,
C₁₋₆-alkyl, C₂₋₆-alkenyl or C₂₋₆-alkynyl,
which may optionally be substituted with one or more substituents selected from halogen, —CN, —CF₃, —OCF₃, —NO₂, —OR²¹, —NR²¹R²² and C₁₋₆-alkyl, C₃₋₈-cycloalkyl, C₄₋₈-cycloalkenyl, heterocyclyl, C₃₋₈-cycloalkyl-C₁₋₆-alkyl, C₃₋₈-cycloalkyl-C₁₋₆-alkoxy, C₃₋₈-cycloalkyloxy, C₃₋₈-cycloalkyl-C₁₋₆-alkylthio, C₃₋₈-cycloalkylthio, C₃₋₈-cycloalkyl-C₂₋₆-alkenyl, C₃₋₈-cycloalkyl-C₂₋₆-alkynyl, C₄₋₈-cycloalkenyl- C$_{1-6}$-alkyl, C$_{4-8}$-cycloalkenyl-C$_{2-6}$-alkenyl, C$_{4-8}$-cycloalkenyl-C$_{2-6}$-alkynyl, heterocyclyl-C$_{1-6}$-alkyl, heterocyclyl-C$_{2-6}$-alkenyl, heterocyclyl-C$_{2-6}$-alkynyl, aryl, aryloxy, aryloxycarbonyl, aroyl, aryl-C$_{1-6}$-alkoxy, aryl-C$_{1-6}$-alkyl, aryl-C$_{2-6}$-alkenyl, aryl-C$_{2-6}$-alkynyl, heteroaryl, heteroaryl-C$_{1-6}$-alkyl, heteroaryl-C$_{2-6}$-alkenyl or heteroaryl-C$_{2-6}$-alkynyl, of which the cyclic moieties optionally may be substituted with one or more substituents selected from halogen, —CN, —CF$_3$, —OCF$_3$, —NO$_2$, —OR$^{21}$, —NR$^{21}$R$^{22}$ and C$_{1-6}$-alkyl, wherein R$^{21}$ and R$^{22}$ independently are hydrogen, C$_{1-6}$-alkyl or aryl, or R$^{21}$ and R$^{22}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, or two of the groups R$^{15}$ to R$^{18}$ when placed in adjacent positions together may form a bridge —(CR$^{23}$R$^{24}$)$_a$—O—(CR$^{25}$R$^{26}$)$_c$—O—, wherein a is 0, 1 or 2, c is 1 or 2, R$^{23}$, R$^{24}$, R$^{25}$ and R$^{26}$ independently are hydrogen, C$_{1-6}$-alkyl or fluorine, R$^{19}$ and R$^{20}$ independently are hydrogen, C$_{1-6}$-alkyl, C$_{3-8}$-cycloalkyl or C$_{3-8}$-cycloalkyl-C$_{1-6}$-alkyl, E is

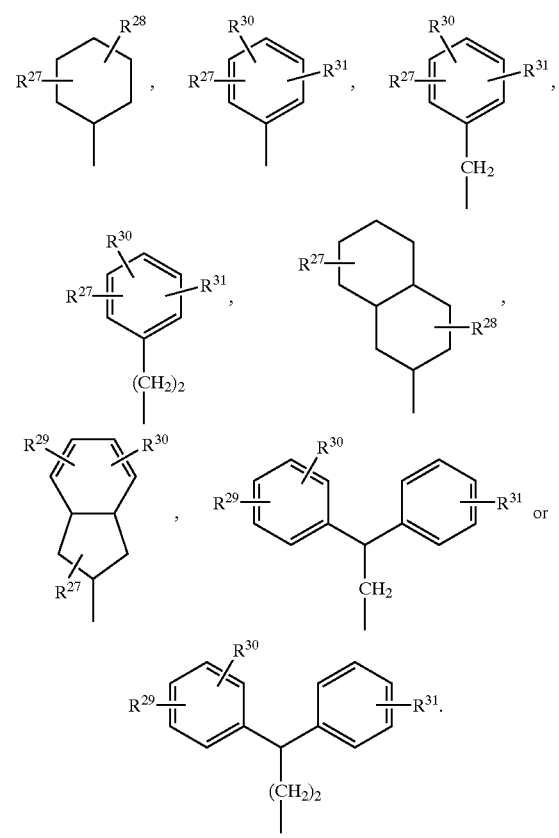

wherein

R$^{27}$ and R$^{28}$ independently are hydrogen, halogen, —CN, —CF$_3$, —OCF$_3$, —OR$^{32}$, —NR$^{32}$R$^{33}$, C$_{1-6}$-alkyl, C$_{3-8}$-cycloalkyl, C$_{4-8}$-cycloalkenyl or aryl, wherein the aryl group optionally may be substituted with one or more substituents selected from halogen, —CN, —CF$_3$, —OCF$_3$, —NO$_2$, —OR$^{32}$, —NR$^{32}$R$^{33}$ and C$_{1-6}$-alkyl, wherein R$^{32}$ and R$^{33}$ independently are hydrogen or C$_{1-6}$-alkyl, or R$^{32}$ and R$^{33}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, R$^{29}$, R$^{30}$ and R$^{31}$ independently are hydrogen, halogen, —CHF$_2$, —CF$_3$, —OCF$_3$, —OCHF$_2$, —OCH$_2$CF$_3$, —OCF$_2$CHF$_2$, —SCF$_3$, —OR$^{34}$, —NR$^{34}$R$^{35}$, —SR$^{34}$, —S(O)R$^{34}$, —S(O)$_2$R$^{34}$, —C(O)NR$^{34}$R$^{35}$, —OC(O)NR$^{34}$R$^{35}$, —NR$^{34}$C(O)R$^{35}$, —OCH$_2$C(O)NR$^{34}$R$^{35}$, —C(O)R$^{34}$ or —C(O)OR$^{34}$, C$_{1-6}$-alkyl, C$_{2-6}$-alkenyl or C$_{2-6}$-alkynyl, which may optionally be substituted with one or more substituents selected from halogen, —CN, —CF$_3$, —OCF$_3$, —NO$_2$, —OR$^{34}$, —NR$^{34}$R$^{35}$ and C$_{1-6}$-alkyl, C$_{3-8}$-cycloalkyl, C$_{4-8}$-cycloalkenyl, heterocyclyl, C$_{3-8}$-cycloalkyl-C$_{1-6}$-alkyl, C$_{3-8}$-cycloalkyl-C$_{2-6}$-alkenyl, C$_{3-8}$-cycloalkyl-C$_{2-6}$-alkynyl, C$_{4-8}$-cycloalkenyl-C$_{1-6}$-alkyl, C$_{4-8}$-cycloalkenyl-C$_{2-6}$-alkenyl, C$_{4-8}$-cycloalkenyl-C$_{2-6}$-alkynyl, heterocyclyl-C$_{1-6}$-alkyl, heterocyclyl-C$_{2-6}$-alkenyl, heterocyclyl-C$_{2-6}$-alkynyl, aryl, aryloxy, aroyl, aryl-C$_{1-6}$-alkoxy, aryl-C$_{1-6}$-alkyl, aryl-C$_{2-6}$-alkenyl, aryl-C$_{2-6}$-alkynyl, heteroaryl, heteroaryl-C$_{1-6}$-alkyl, heteroaryl-C$_{2-6}$-alkenyl or heteroaryl-C$_{2-6}$-alkynyl, of which the cyclic moieties optionally may be substituted with one or more substituents selected from halogen, —CN, —CF$_3$, —OCF$_3$, —NO$_2$, —OR$^{34}$, —NR$^{34}$R$^{35}$ and C$_{1-6}$-alkyl, wherein R$^{34}$ and R$^{35}$ independently are hydrogen, C$_{1-6}$-alkyl or aryl, or R$^{34}$ and R$^{35}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, or two of the groups R$^{29}$, R$^{30}$ and R$^{31}$ when attached to the same ring carbon atom or different ring carbon atoms together may form a radical —O—(CH$_2$)$_t$—CR$^{36}$R$^{37}$—(CH$_2$)$_l$—O—, —(CH$_2$)$_t$—CR$^{36}$R$^{37}$—(CH$_2$)$_l$— or —S—(CH$_2$)$_t$—CR$^{36}$R$^{37}$—(CH$_2$)$_l$—S—, wherein t and l independently are 0, 1, 2, 3, 4 or 5, R$^{36}$ and R$^{37}$ independently are hydrogen or C$_{1-6}$-alkyl, as well as any optical or geometric isomer or tautomeric form thereof including mixtures of these or a pharmaceutically acceptable salt thereof.

In one embodiment B is

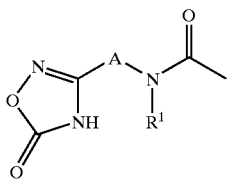

wherein A and $R^1$ are as defined for formula (I).

In a further embodiment A is a valence bond, —$CH_2$— or —$CH_2CH_2$—, such as A —$CH_2$—.

In still a further embodiment $R^1$ is hydrogen.

In another embodiment B is

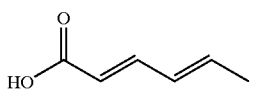

In still another embodiment B is

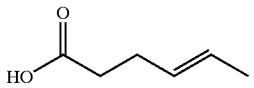

In yet another embodiment B is

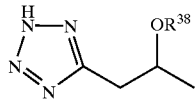

wherein $R^{38}$ is as defined for formula (I).

In still a further embodiment $R^2$ is hydrogen.

In another embodiment Z is

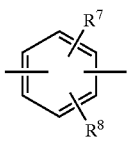

wherein $R^7$ and $R^8$ are as defined for formula (I).

In still another embodiment Z is

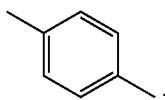

In yet another embodiment X is

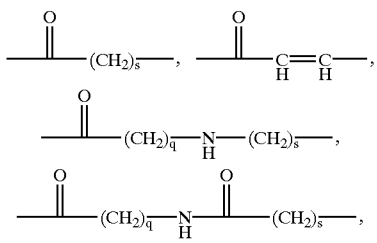

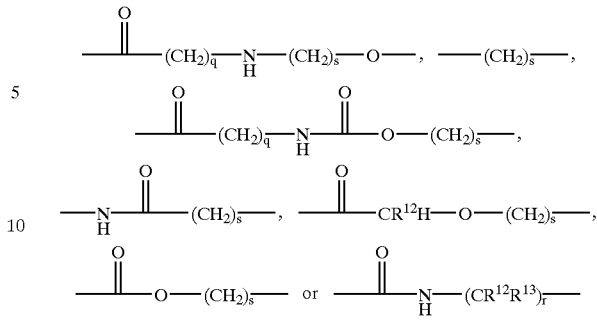

wherein q is 0 or 1, r is 0 or 1, s is 0, 1 or 2, and $R^{12}$ and $R^{13}$ independently are hydrogen or $C_{1-6}$-alkyl.

In still another embodiment X is —C(O)NH—, —C(O)NHCH$_2$—, —C(O)NHCH(CH$_3$)—, —C(O)NHCH$_2$CH$_2$—, —C(O)CH$_2$—, —C(O)CH=CH—, —(CH$_2$)$_s$—, —C(O)—, —C(O)O— or —NHC(O)—, wherein s is 0 or 1.

In a further embodiment X is —C(O)NH—, —C(O)NHCH$_2$—, —C(O)NHCH(CH$_3$)—, —C(O)NHCH$_2$CH$_2$—, —C(O)CH$_2$—, —CH$_2$—, —C(O)— or —NHC(O)—, such as —C(O)NH—.

In another embodiment D is

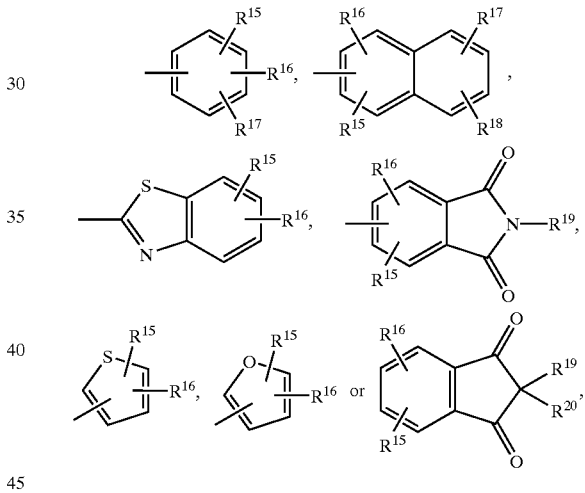

wherein $R^{15}$, $R^{16}$, $R^{17}$, $R^{18}$, $R^{19}$ and $R^{20}$ are as defined for formula (I).

In still another embodiment D is

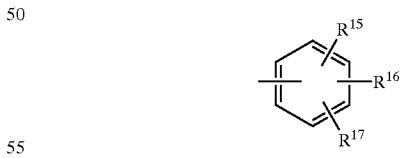

wherein $R^{15}$, $R^{16}$ and $R^{17}$ are as defined for formula (I).

In an embodiment thereof $R^{15}$, $R^{16}$ and $R^{17}$ are independently hydrogen, halogen, —CN, —NO$_2$, —CF$_3$, —OCF$_3$, —SCF$_3$, $C_{1-6}$-alkyl, $C_{1-6}$-alkoxy, —S—$C_{1-6}$-alkyl, —C(O)OR$^{21}$, —C(O)R$^{21}$, —CH$_2$OR$^{21}$, —C(O)NR$^{21}$R$^{22}$, —S(O)$_2$R$^{21}$, —S(O)$_2$CF$_3$, —S(O)$_2$NR$^{21}$R$^{22}$, $C_{3-8}$-cycloalkyl or aryl, or two of the groups $R^{15}$, $R^{16}$ and $R^{17}$ when placed in adjacent positions together form a bridge —(CR$^{23}$R$^{24}$)$_a$—O—(CR$^{25}$R$^{26}$)$_c$—O—, wherein $R^{21}$ and $R^{22}$ independently are hydrogen or $C_{1-6}$-alkyl, and a, c, $R^{23}$, $R^{24}$, $R^{25}$ and $R^{26}$ are as defined for formula (I).

In another embodiment thereof $R^{15}$, $R^{16}$ and $R^{17}$ are independently hydrogen, —S—$C_{1-6}$-alkyl, halogen, —CN, —$CF_3$, —$OCF_3$ or $C_{1-6}$-alkoxy, or wherein two of the substituents in adjacent positions form the bridge —$CF_2$—O—$CF_2$—O—.

In yet another embodiment thereof $R^{15}$, $R^{16}$ and $R^{17}$ are independently hydrogen, halogen, —S—$CH_3$, —$CF_3$ or —$OCF_3$, or wherein two of the substituents in adjacent positions form the bridge —$CF_2$—O—$CF_2$—O—.

In a further embodiment E is

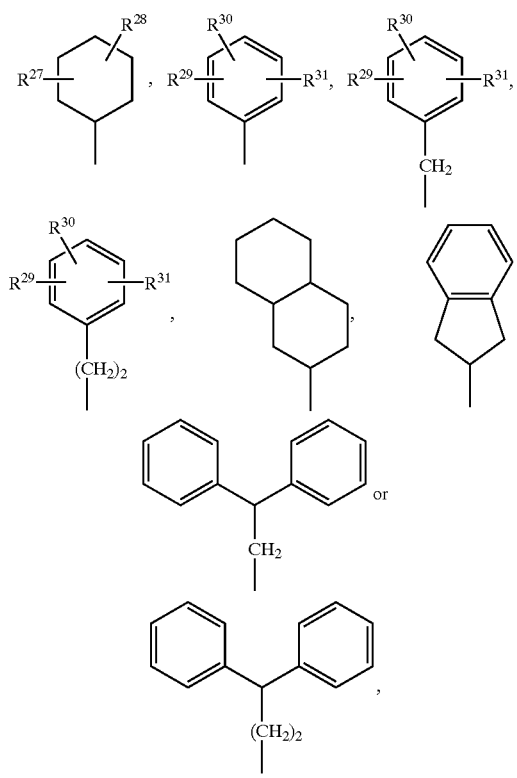

wherein $R^{27}$, $R^{28}$, $R^{29}$, $R^{30}$ and $R^{31}$ are as defined for formula (I).

In still a further embodiment E is

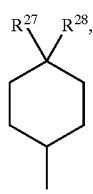

wherein $R^{27}$ and $R^{28}$ are as defined for formula (I).

In an embodiment thereof $R^{27}$ and $R^{28}$ are independently hydrogen, $C_{1-6}$alkyl, $C_{3-8}$-cycloalkyl, $C_{4-8}$-cycloalkenyl or phenyl.

In another embodiment thereof $R^{27}$ is hydrogen and $R^{28}$ is $C_{1-6}$-alkyl, $C_{4-8}$-cycloalkenyl or $C_{3-8}$-cycloalkyl.

In still another embodiment E is

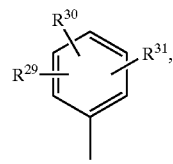

wherein $R^{29}$, $R^{30}$ and $R^{31}$ are as defined for formula (I).
In yet another embodiment E is

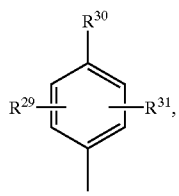

wherein $R^{29}$, $R^{30}$ and $R^{31}$ are as defined for formula (I).

In an embodiment thereof $R^{29}$, $R^{30}$ and $R^{31}$ are independently
  hydrogen, —$CHF_2$, —$CF_3$, —$OCF_3$, —$OCHF_2$, —$OCH_2CF_3$, —$OCF_2CHF_2$, —$SCF_3$, —$OR^{34}$, —$NR^{34}R^{35}$, —$SR^{34}$, —$S(O)R^{34}$, —$S(O)_2R^{34}$, —$C(O)NR^{34}R^{35}$, —$OC(O)NR^{34}R^{35}$, —$NR^{34}C(O)R^{35}$, —$OCH_2C(O)NR^{34}R^{35}$, —$C(O)R^{34}$ or —$C(O)OR^{34}$,
  $C_{1-6}$-alkyl, $C_{2-6}$-alkenyl or $C_{2-6}$-alkynyl,
    which may optionally be substituted with one or more substituents selected from halogen, —CN, —$CF_3$, —$OCF_3$, —$NO_2$, —$OR^{34}$, —$NR^{34}R^{35}$ and $C_{1-6}$alkyl,
  $C_{3-8}$-cycloalkyl or $C_{4-8}$-cycloalkenyl,
    which may optionally be substituted with one or more substituents selected from halogen, —CN, —$CF_3$, —$OCF_3$, —$NO_2$, —$OR^{34}$, —$NR^{34}R^{35}$ and $C_{1-6}$-alkyl,
  wherein $R^{34}$ and $R^{35}$ independently are hydrogen, $C_{1-6}$alkyl or aryl,
  or $R^{34}$ and $R^{35}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds.

In another embodiment thereof $R^{29}$, $R^{30}$ and $R^{31}$ are independently
  hydrogen, $C_{1-6}$alkoxy, —$CF_3$, —$OCF_3$ or —$NR^{34}R^{35}$, wherein $R^{34}$ and $R^{35}$ are as defined for formula (I), or
  $C_{1-6}$alkyl, $C_{3-8}$-cycloalkyl or $C_{4-8}$-cycloalkenyl, which are optionally substituted as defined for formula (I).

In yet another embodiment thereof $R^{29}$, $R^{30}$ and $R^{31}$ are independently
  hydrogen or
  $C_{1-6}$-alkyl, $C_{3-8}$-cycloalkyl or $C_{4-8}$-cycloalkenyl, which are optionally substituted as defined for formula (I).

In yet another embodiment thereof $R^{29}$, $R^{30}$ and $R^{31}$ are independently hydrogen, $C_{1-6}$-alkyl, $C_{3-8}$-cycloalkyl or $C_{4-8}$-cycloalkenyl.

In still another embodiment thereof $R^{29}$ and $R^{31}$ are both hydrogen and $R^{30}$ is $C_{1-6}$-alkyl, $C_{3-8}$-cycloalkyl or $C_{4-8}$-cycloalkenyl, such as $C_{1-6}$-alkyl.

In another embodiment the invention relates to compounds of the general formula (Ia):

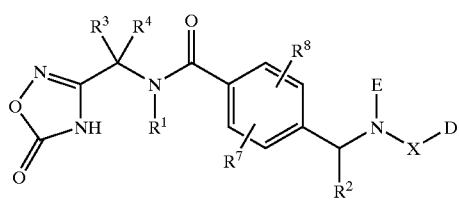
(Ia)

wherein $R^1$, $R^2$, $R^3$, $R^4$, $R^7$, $R^8$, X, D and E are as defined for formula (I) or as defined in the embodiments above.

In one embodiment thereof $R^1$, $R^2$, $R^3$, $R^4$, $R^7$ and $R^8$ are hydrogen.

In another embodiment the invention relates to compounds of the general formula (Ib):

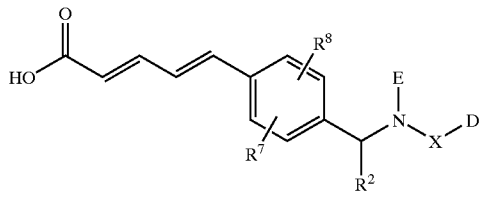
(Ib)

wherein $R^2$, $R^7$, $R^8$, X, D and E are as defined for formula (I) or as defined in the embodiments above.

In still another embodiment the invention relates to compounds of the general formula (Ic):

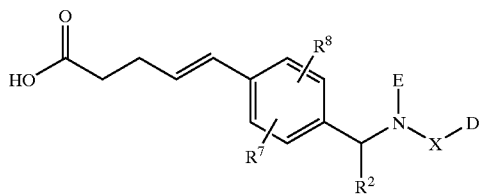
(Ic)

wherein $R^2$, $R^7$, $R^8$, X, D and E are as defined for formula (I) or as defined in the embodiments above.

In yet another embodiment the invention relates to compounds of the general formula (Id):

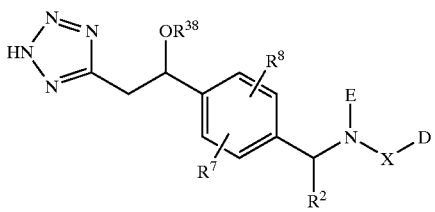
(Id)

wherein $R^2$, $R^7$, $R^8$, $R^{38}$; X, D and E are as defined for formula (I) or as defined in the embodiments above.

In an embodiment $R^2$, $R^7$ and $R^8$ are hydrogen in the formulae (Ia), (Ib), (Ic) and (Id).

In another aspect, the invention is concerned with compounds of the general formula (I'):

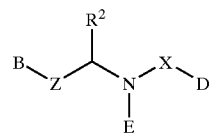
(I')

wherein $R^2$ is hydrogen or $C_{1-6}$-alkyl,

B is

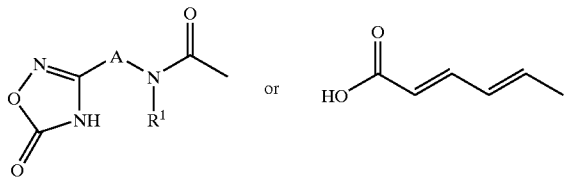

wherein

A is a valence bond, —(CR$^3$R$^4$)—, or —(CR$^3$R$^4$)(CR$^5$R$^6$)—, $R^1$, $R^3$, $R^4$, $R^5$ and $R^6$ independently are hydrogen or $C_{1-6}$-alkyl, Z is arylene or a divalent radical derived from a 5 or 6 membered heteroaromatic ring containing 1 or 2 heteroatoms selected from nitrogen, oxygen and sulfur, which may optionally be substituted with one or two groups $R^7$ and $R^8$ selected from halogen, —CN, —CF$_3$, —OCF$_3$, —NO$_2$, —OR$^9$, —NR$^9$R$^{10}$ and $C_{1-6}$-alkyl, wherein $R^9$ and $R^{10}$ independently are hydrogen or $C_{1-6}$-alkyl, X is

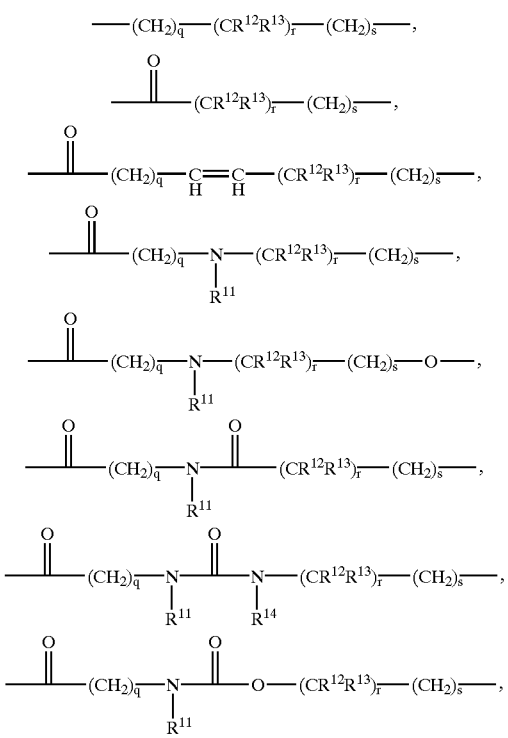

-continued

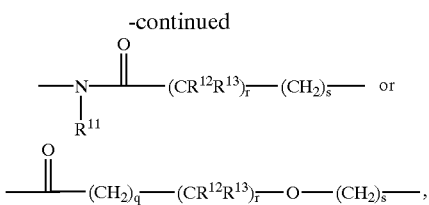

wherein
r is 0 or 1,
q and s independently are 0, 1, 2 or 3,
$R^{11}$, $R^{12}$, $R^{13}$ and $R^{14}$ independently are hydrogen or $C_{1-6}$-alkyl,
D is

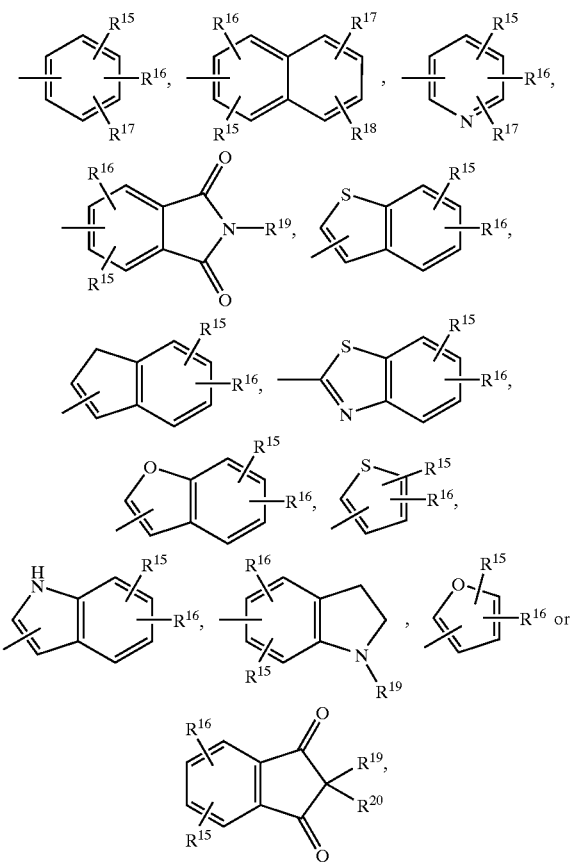

wherein
$R^{15}$, $R^{16}$, $R^{17}$ and $R^{18}$ independently are
hydrogen, halogen, —CN, —$CH_2CN$, —$CHF_2$, —$CF_3$, —$OCF_3$, —$OCHF_2$, —$OCH_2CF_3$, —$OCF_2CHF_2$, —$S(O)_2CF_3$, —$SCF_3$, —$NO_2$, —$OR^{21}$, —$NR^{21}R^{22}$, —$SR^{21}$, —$NR^{21}S(O)_2R^{22}$, —$S(O)_2NR^{21}R^{22}$, —$S(O)NR^{21}R^{22}$, —$S(O)R^{21}$, —$S(O)_2R^{21}$, —$C(O)NR^{21}R^{22}$, $OC(O)NR^{21}R^{22}$, —$NR^{21}C(O)R^{22}$, —$CH_2C(O)NR^{21}R^{22}$, —$OCH_2C(O)NR^{21}R^{22}$, —$CH_2OR^{21}$, —$CH_2NR^{21}R^{22}$, —$OC(O)R^{21}$, —$C(O)R^{21}$ or —$C(O)OR^{21}$,
$C_{1-6}$-alkyl, $C_{2-6}$-alkenyl or $C_{2-6}$-alkynyl,
which may optionally be substituted with one or more substituents selected from halogen, —CN, —$CF_3$, —$OCF_3$, —$NO_2$, —$OR^{21}$, —$NR^{21}R^{22}$ and $C_{1-6}$-alkyl,
$C_{3-8}$-cycloalkyl, $C_{4-8}$-cycloalkenyl, heterocyclyl, $C_{3-8}$-cycloalkyl-$C_{1-6}$-alkyl, $C_{3-8}$-cycloalkyl-$C_{1-6}$-alkoxy, $C_{3-8}$-cycloalkyloxy, $C_{3-8}$-cycloalkyl-$C_{1-6}$-alkylthio, $C_{3-8}$-cycloalkylthio, $C_{3-8}$-cycloalkyl-$C_{2-6}$-alkenyl, $C_{3-8}$-cycloalkyl-$C_{2-6}$-alkynyl, $C_{4-8}$-cycloalkenyl-$C_{1-6}$-alkyl, $C_{4-8}$-cycloalkenyl-$C_{2-6}$-alkenyl, $C_{4-8}$-cycloalkenyl-$C_{2-6}$-alkynyl, heterocyclyl-$C_{1-6}$-alkyl, heterocyclyl-$C_{2-6}$-alkenyl, heterocyclyl-$C_{2-6}$-alkynyl, aryl, aryloxy, aryloxycarbonyl, aroyl, aryl-$C_{1-6}$-alkoxy, aryl-$C_{1-6}$-alkyl, aryl-$C_{2-6}$-alkenyl, aryl-$C_{2-6}$-alkynyl, heteroaryl, heteroaryl-$C_{1-6}$-alkyl, heteroaryl-$C_{2-4}$-alkenyl or heteroaryl-$C_{2-6}$-alkynyl, of which the cyclic moieties optionally may be substituted with one or more substituents selected from halogen, —CN, —$CF_3$, —$OCF_3$, —$NO_2$, —$OR^{21}$, —$NR^{21}R^{22}$ and $C_{1-6}$-alkyl, wherein $R^{21}$ and $R^{22}$ independently are hydrogen, $C_{1-6}$-alkyl or aryl,
or $R^{21}$ and $R^{22}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, or two of the groups $R^{15}$ to $R^{18}$ when placed in adjacent positions together may form a bridge —$(CR^{23}R^{24})_a$—O—$(CR^{25}R^{26})_c$—O—, wherein a is 0, 1 or 2,
c is 1 or 2,
$R^{23}$, $R^{24}$, $R^{25}$ and $R^{26}$ independently are hydrogen, $C_{1-6}$-alkyl or fluorine,
$R^{19}$ and $R^{20}$ independently are hydrogen, $C_{1-6}$-alkyl, $C_{3-8}$-cycloalkyl or $C_{3-8}$-cycloalkyl-$C_{1-6}$-alkyl,
E is

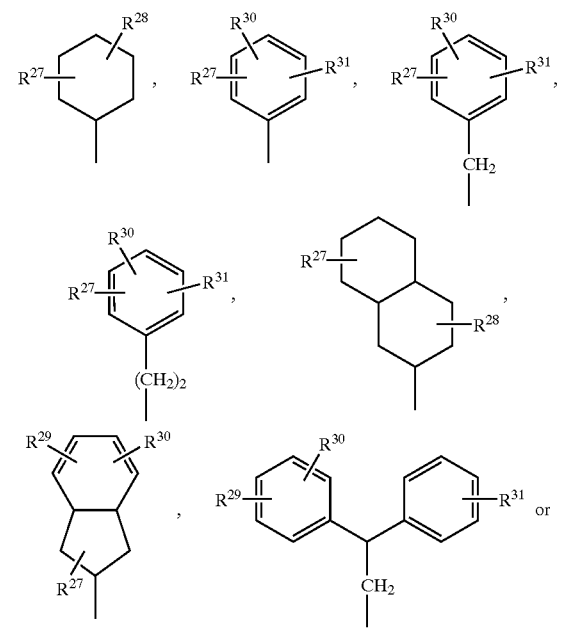

-continued

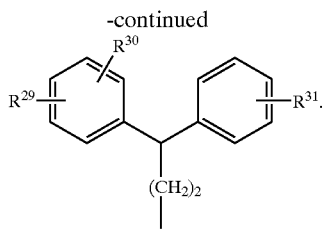

wherein
R$^{27}$ and R$^{28}$ independently are
hydrogen, halogen, —CN, —CF$_3$, —OCF$_3$, —OR$^{32}$, —NR$^{32}$R$^{33}$, C$_{1-6}$-alkyl, C$_{3-8}$-cycloalkyl, C$_{4-8}$-cycloalkenyl or aryl,
wherein the aryl group optionally may be substituted with one or more substituents selected from halogen, —CN, —CF$_3$, —OCF$_3$, —NO$_2$, —OR$^{32}$, —NR$^{32}$R$^{33}$ and C$_{1-6}$-alkyl,
wherein
R$^{32}$ and R$^{33}$ independently are hydrogen or $_{1-6}$-alkyl, or
R$^{32}$ and R$^{33}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds,
R$^{29}$, R$^{30}$ and R$^{31}$ independently are
hydrogen, halogen, —CHF$_2$, —CF$_3$, —OCF$_3$, —OCHF$_2$, —OCH$_2$CF$_3$, —OCF$_2$CHF$_2$, —SCF$_3$, —OR$^{34}$, —NR$^{34}$R$^{35}$, —SR$^{34}$, —S(O)R$^{34}$, —S(O)$_2$R$^{34}$, —C(O)NR$^{34}$R$^{35}$, —OC(O)NR$^{34}$R$^{35}$, —NR$^{34}$C(O)R$^{35}$, —OCH$_2$C(O)NR$^{34}$R$^{35}$, —C(O)R$^{34}$ or —C(O)OR$^{34}$,
C$_{1-6}$-alkyl, C$_{2-6}$-alkenyl or C$_{2-6}$-alkynyl,
which may optionally be substituted with one or more substituents selected from halogen, —CN, —CF$_3$, —OCF$_3$, —NO$_2$, —OR$^{34}$, —NR$^{34}$R$^{35}$ and C$_{1-6}$-alkyl,
C$_{3-8}$-cycloalkyl, C$_{4-8}$-cycloalkenyl, heterocyclyl, C$_{3-8}$-cycloalkyl-C$_{1-6}$-alkyl, C$_{3-8}$-cycloalkyl-C$_{2-6}$-alkenyl, C$_{3-8}$-cycloalkyl-C$_{2-6}$-alkynyl, C$_{4-8}$-cycloalkenyl-C$_{1-6}$-alkyl, C$_{4-8}$-cycloalkenyl-C$_{2-6}$-alkenyl, C$_{4-8}$-cycloalkenyl-C$_{2-6}$-alkynyl, heterocyclyl-C$_{1-6}$-alkyl, heterocyclyl-C$_{2-6}$-alkenyl, heterocyclyl-C$_{2-6}$-alkynyl, aryl, aryloxy, aroyl, aryl-C$_{1-6}$-alkoxy, aryl-C$_{1-6}$-alkyl, aryl-C$_{2-6}$-alkenyl, aryl-C$_{2-6}$-alkynyl, heteroaryl, heteroaryl-C$_{1-6}$-alkyl, heteroaryl-C$_{2-6}$-alkenyl or heteroaryl-C$_{2-6}$-alkynyl,
of which the cyclic moieties optionally may be substituted with one or more substituents selected from halogen, —CN, —CF$_3$, —OCF$_3$, —NO$_2$, —OR$^{34}$, —NR$^{34}$R$^{35}$ and C$_{1-6}$-alkyl,
wherein R$^{34}$ and R$^{35}$ independently are hydrogen, C$_{1-6}$-alkyl or aryl,
or R$^{34}$ and R$^{35}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds,
or two of the groups R$^{29}$, R$^{30}$ and R$^{31}$ when attached to the same ring carbon atom or different ring carbon atoms together may form a radical —O—(CH$_2$)$_t$—CR$^{36}$R$^{37}$—(CH$_2$)$_l$—O—, —(CH$_2$)$_t$—CR$^{36}$R$^{37}$—(CH$_2$)$_l$— or —S—(CH$_2$)$_t$—CR$^{36}$R$^{37}$—(CH$_2$)$_l$—S—, wherein
t and l independently are 0, 1, 2, 3, 4 or 5,
R$^{36}$ and R$^{37}$ independently are hydrogen or C$_{1-6}$-alkyl,
as well as any optical or geometric isomer or tautomeric form thereof including mixtures of these or a pharmaceutically acceptable salt thereof.

The compounds of the present invention may have one or more asymmetric centres and it is intended that any optical isomers, as separated, pure or partially purified optical isomers or racemic mixtures thereof are included within the scope of the invention.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

The present invention also encompasses pharmaceutically acceptable salts of the present compounds. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methyl-, dimethyl-, trimethyl-, ethyl-, hydroxyethyl-, diethyl-, butyl-, tetramethylammonium salts and the like.

Also intended as pharmaceutically acceptable acid addition salts are the hydrates which the present compounds are able to form.

Furthermore, the pharmaceutically acceptable salts comprise basic amino acid salts such as lysine, arginine and ornithine.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of the present invention may form solvates with standard low molecular weight solvents using methods well known to the person skilled in the art. Such solvates are also contemplated as being within the scope of the present invention.

The invention also encompasses prodrugs of the present compounds, which on administration undergo chemical conversion by metabolic processes before becoming pharmacologically active substances. In general, such prodrugs will be functional derivatives of the compounds of the general formula (I), which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The compounds according to the present invention act to antagonize the action of glucagon and are accordingly useful for the treatment and/or prevention of disorders and diseases in which such an antagonism is beneficial.

Accordingly, the present compounds may be applicable for the treatment and/or prevention of hyperglycemia, IGT (impaired glucose tolerance), insulin resistance syndromes, syndrome X, Type 1 diabetes, Type 2 diabetes, hyperlipidemia, dyslipidemia, hypertriglyceridemia, hyperlipoproteinemia, hypercholesteroleria, arteriosclerosis including atherosclerosis, glucagonomas, acute pancreatitis, cardiovascular diseases, hypertension, cardiac hypertrophy, gastrointestinal disorders, obesity, diabetes as a consequence of obesity, diabetic dyslipidemia, etc.

Furthermore, they may be applicable as diagnostic agents for identifying patients having a defect in the glucagon receptor, as a therapy to increase gastric acid secretions and to reverse intestinal hypomobility due to glucagon administration.

They may also be useful as tool or reference molecules in labelled form in binding assays to identify new glucagon antagonists.

Accordingly, in a further aspect the invention relates to a compound according to the invention for use as a medicament.

The invention also relates to pharmaceutical compositions comprising, as an active ingredient, at least one compound according to the invention together with one or more pharmaceutically acceptable carriers or excipients.

The pharmaceutical composition is preferably in unit dosage form, comprising from about 0.05 mg to about 1000 mg, preferably from about 0.1 mg to about 500 mg and especially preferred from about 0.5 mg to about 200 mg of the compound according to the invention.

Furthermore, the invention relates to the use of a compound according to the invention for the preparation of a pharmaceutical composition for the treatment and/or prevention of a disorder or disease, wherein a glucagon antagonistic action is beneficial.

The invention also relates to a method for the treatment and/or prevention of disorders or diseases, wherein a glucagon antagonistic action is beneficial the method comprising administering to a subject in need thereof an effective amount of a compound according to the invention.

In a preferred embodiment of the invention the present compounds are used for the preparation of a medicament for the treatment and/or prevention of any glucagon-mediated conditions and diseases.

In a preferred embodiment of the invention the present compounds are used for the preparation of a medicament for the treatment and/or prevention of hyperglycemia.

In yet a preferred embodiment of the invention the present compounds are used for the preparation of a medicament for lowering blood glucose in a mammal. The present compounds are effective in lowering the blood glucose, both in the fasting and the postprandial stage.

In another preferred embodiment of the invention the present compounds are used for the preparation of a pharmaceutical composition for the treatment and/or prevention of IGT.

In still another preferred embodiment of the invention the present compounds are used for the preparation of a pharmaceutical composition for the treatment and/or prevention of Type 2 diabetes.

In yet another preferred embodiment of the invention the present compounds are used for the preparation of a pharmaceutical composition for the delaying or prevention of the progression from IGT to Type 2 diabetes.

In yet another preferred embodiment of the invention the present compounds are used for the preparation of a pharmaceutical composition for the delaying or prevention of the progression from non-insulin requiring Type 2 diabetes to insulin requiring Type 2 diabetes.

In a further preferred embodiment of the invention the present compounds are used for the preparation of a pharmaceutical composition for the treatment and/or prevention of Type 1 diabetes. Such treatment and/or prevention is normally accompanied by insulin therapy.

In a further preferred embodiment of the invention the present compounds are used for the preparation of a pharmaceutical composition for the treatment and/or prevention of obesity.

In yet a further preferred embodiment of the invention the present compounds are used for the preparation of a pharmaceutical composition for the treatment and/or prevention of disorders of the lipid metabolism.

In still a further preferred embodiment of the invention the present compounds are used for the preparation of a pharmaceutical composition for the treatment and/or prevention of an appetite regulation or energy expenditure disorder.

In a further aspect of the invention, treatment of a patient with the present compounds is combined with diet and/or exercise.

In still a further aspect of the invention the present compounds are administered in combination with one or more further active substances in any suitable ratios. Such further active substances may eg be selected from antiobesity agents, antidiabetics, antihypertensive agents, agents for the treatment of complications resulting from or associated with diabetes and agents for the treatment of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, MC3 (melanocortin 3) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin re-uptake inhibitors such as fluoxetine, seroxat or citalopram, serotonin and noradrena line re-uptake inhibitors, mixed serotonin and noradrenergic compounds, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, H3 histamine antagonists, opioid antagonists (such as naitrexone), exendin-4, GLP-1 and ciliary neurotrophic factor.

In one embodiment of the invention the antiobesity agent is leptin.

In another embodiment the antiobesity agent is dexamphetamine or amphetamine.

In another embodiment the antiobesity-agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

In still another embodiment the antiobesity agent is phendimetrazine, diethylpropion, fluoxetine, bupropion, topiramate or ecopipam.

Suitable antidiabetic agents include insulin, insulin analogues and derivatives such as those disclosed in EP 792 290 (Novo Nordisk A/S), eg $N^{\epsilon B29}$-tetradecanoyl des (B30) human insulin, EP 214 826 and EP 705 275 (Novo Nordisk A/S), eg $Asp^{B28}$ human insulin, U.S. Pat. No. 5,504,188 (Eli Lilly), eg $Lys^{B28}$ $Pro^{B29}$ human insulin, EP 368 187 (Aventis), eg Lantus, which are all incorporated herein by reference, GLP-1 and GLP-1 derivatives such as those disclosed in WO 98/08871 (Novo Nordisk A/S), which is incorporated herein by reference, as well as orally active hypoglycemic agents.

The orally active hypoglycemic agents preferably comprise imidazolines, sulphonylureas, biguanides, meglitinides, oxadiazolidinediones, thiazolidinediones, insulin sensitizers, insulin secretagogues such as glimepride, α-glucosidase inhibitors, agents acting on the ATP-dependent potassium channel of the β-cells eg potassium channel openers such as those disclosed in WO 97/26265, WO 99/03861 and WO 00/37474 (Novo Nordisk A/S) which are incorporated herein by reference, or mitiglinide, or a potassium channel blocker, such as BTS-67582, nateglinide, glucagon antagonists such as those disclosed in WO 99/01423 and WO 00/39088 (Novo Nordisk A/S and Agouron Pharmaceuticals, Inc.), which are incorporated herein by reference, GLP-1 agonists such as those disclosed in WO 00/42026 (Novo Nordisk A/S and Agouron Pharmaceuticals, Inc.), which are incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antilipidemic agents, compounds lowering food intake, PPAR (peroxisome proliferator-activated receptor) and RXR (retinoid X receptor) agonists, such as ALRT-268; LG-1268 or LG-1069.

In one embodiment, the present compounds are administered in combination with insulin or an insulin analogue or derivative, such as $N^{\epsilon B29}$-tetradecanoyl des (B30) human insulin, $Asp^{B28}$ human insulin, $Lys^{B28}$ $Pro^{B29}$ human insulin, Lantus®, or a mix-preparation comprising one or more of these.

In a further embodiment of the invention the present compounds are administered in combination with a sulphonylurea eg tolbutamide, chlorpropamide, tolazamide, glibenclamide, glipizide, glimepiride, glicazide or glyburide.

In another embodiment of the invention the present compounds are administered in combination with a biguanide eg metformin.

In yet another embodiment of the invention the present compounds are administered in combination with a meglitinide eg repaglinide or nateglinide.

In still another embodiment of the invention the present compounds are administered in combination with a thiazolidinedione insulin sensitizer eg troglitazone, ciglitazone, pioglitazone, rosiglitazone, isaglitazone, darglitazone, englitazone, CS-011/CI-1037 or T 174 or the compounds disclosed in WO 97/41097, WO 97/41119, WO 97/41120, WO 00/41121 and WO 98/45292 (Dr. Reddy's Research Foundation), which are incorporated herein by reference.

In still another embodiment of the invention the present compounds may be administered in combination with an insulin sensitizer eg such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313, WO 00/50414, WO 00/63191, WO 00/63192, WO 00/63193 (Dr. Reddy's Research Foundation) and WO 00/23425, WO 00/23415, WO 00/23451, WO 00/23445, WO 00/23417, WO 00/23416, WO 00/63153, WO 00/63196, WO 00/63209, WO 00/63190 and WO 00/63189 (Novo Nordisk A/S), which are incorporated herein by reference.

In a further embodiment of the invention the present compounds are administered in combination with an α-glucosidase inhibitor eg voglibose, emiglitate, miglitol or acarbose.

In another embodiment of the invention the present compounds are administered in combination with an agent acting on the ATP-dependent potassium channel of the β-cells eg tolbutamide, glibenclamide, glipizide, glicazide, BTS-67582 or repaglinide.

In yet another embodiment of the invention the present compounds may be administered in combination with nateglinide.

In still another embodiment of the invention the present compounds are administered in combination with an antilipidemic agent eg cholestyramine, colestipol, clofibrate, gemfibrozil, lovastatin, pravastatin, simvastatin, probucol or dextrothyroxine.

In another aspect of the invention, the present compounds are administered in combination with more than one of the above-mentioned compounds eg in combination with metformin and a sulphonylurea such as glyburide; a sulphonylurea and acarbose; nateglinide and metformin; acarbose and metformin; a sulphonylurea, metformin and troglitazone; insulin and a sulphonylurea; insulin and metformin; insulin, metformin and a sulphonylurea; insulin and troglitazone; insulin and lovastatin; etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

It should be understood that any suitable combination of the compounds according to the invention with diet and/or exercise, one or more of the abovementioned compounds and optionally one or more other active substances are considered to be within the scope of the present invention.

Pharmaceutical Compositions

The compounds of the invention may be administered alone or in combination with pharma-ceutically acceptable carriers or excipients, in either single or multiple doses. The pharmaceu-tical compositions according to the invention may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracistemal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.05 to about 1000 mg, preferably from about 0.1 to about 500 mg, and more preferred from about 0.5 mg to about 200 mg.

For parenteral routes such as intravenous, intrathecal, intramuscular and similar administration, typically doses are in the order of about half the dose employed for oral administration.

The compounds of this invention are generally utilized as the free substance or as a pharmaceutically acceptable salt thereof. One example is an acid addition salt of a compound having the utility of a free base. When a compound of the formula (I) contains a free base such salts are prepared in a conventional manner by treating a solution or suspension of a free base of the formula (I) with a chemical equivalent of a pharmaceutically acceptable acid. Representative examples are mentioned above. Physiologically acceptable salts of a compound with a hydroxy group include the anion of said compound in combination with a suitable cation such as sodium or ammonium ion.

For parenteral administration, solutions of the novel compounds of the formula (I) in sterile aqueous solution, aqueous propylene glycol or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the novel compounds of the formula (I) and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet that may be prepared by conventional tabletting techniques may contain:

| Core: | |
|---|---|
| Active compound (as free compound or salt thereof) | 5.0 mg |
| Lactosum Ph. Eur. | 67.8 mg |
| Cellulose, microcryst. (Avicel) | 31.4 mg |
| Amberlite ® IRP88* | 1.0 mg |
| *Magnesii stearas* Ph. Eur. | q.s. |
| Coating: | |
| Hydroxypropyl methylcellulose | approx. 9 mg |
| Mywacett 9-40 T** | approx. 0.9 mg |

*Polacrillin potassium NF, tablet disintegrant, Rohm and Haas.
**Acylated monoglyceride used as plasticizer for film coating.

If desired, the pharmaceutical composition of the invention may comprise the compound of the formula (I) in combination with further pharmacologically active substances such as those described in the foregoing.

EXAMPLES

The preparation of the compounds of the present invention is described in detail using the following examples, but the chemical reactions described are disclosed in terms of their general applicability to the preparation of the glucagon antagonists of the invention. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, that is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting, materials are known or may easily be prepared from known starting materials. All temperatures are set forth in degrees Celsius and unless otherwise indicated, all parts and percentages are by weight when referring to yields and all parts are by volume when referring to solvents and eluents.

Some of the NMR data shown in the following examples are only selected data.

In the examples and pharmacological methods the following terms are intended to have the following meanings:

DCM: dichloromethane
DCP: 1,2-dichloropropane
DIPEA: diisopropylethylamine
DMF: N,N-dimethylformamide
DMSO: dimethyl sulphoxide
M.p.: melting point
EDAC: 1-ethyl-3-(3-dimethylaminopropyl)carbodiimide hydrochloride
EGTA: ethylene glycol bis(β-aminoethyl ether) N,N,N',N'-tetracetic acid
IBMX: isobutylmethylxanthine
TFA: trifluoroacetic acid
THF: tetrahydrofuran
TMOF: trimethyl orthoformiate

HPLC-MS (Method A)

The following instrumentation was used:
Sciex API 100 Single quadropole mass spectrometer
Perkin Elmer Series 200 Quard pump
Perkin Elmer Series 200 autosampler
Applied Biosystems 785A UV detector
Sedex 55 evaporative light scattering detector
A Valco column switch with a Valco actuator controlled by timed events from the pump.

The Sciex Sample control software running on a Macintosh PowerPC 7200 computer was used for the instrument control and data acquisition.

The HPLC pump was connected to four eluent reservoirs containing:

A: Acetonitrile
B: Water
C: 0.5% TFA in water
D: 0.02 M ammonium acetate

The requirements for samples are that they contain approximately 500 μg/ml of the compound to be analysed in an acceptable solvent such as methanol, ethanol, acetonitrile, THF, water and mixtures thereof. (High concentrations of strongly eluting solvents will interfere with the chromatography at low acetonitrile concentrations.)

The analysis was performed at room temperature by injecting 20 μl of the sample solution on the column, which was eluted with a gradient of acetonitrile in either 0.05% TFA or 0.002 M ammonium acetate. Depending on the analysis method varying elution conditions were used.

The eluate from the column was passed through a flow splitting T-connector, which passed approximately 20 μl/min through approx. 1 m 75μ fused silica capillary to the API interface of API 100 spectrometer.

The remaining 1.48 ml/min was passed through the UV detector and to the ELS detector.

During the LC-analysis the detection data were acquired concurrently from the mass spectrometer, the UV detector and the ELS detector.

The LC conditions, detector settings and mass spectrometer settings used for the different methods are given in the following table.

| | |
|---|---|
| Column | YMC ODS-A 120Ås-5μ 3 mm × 50 mm id |
| Gradient | 5%–90% acetonitrile in 0.05% TFA linearly during 7.5 min at 1.5 ml/min |
| Detection | UV: 214 nm          ELS: 40° C. |
| MS | Experiment: Start: 100 amu   Stop: 800 amu   Step: 0.2 amu |
| | Dwell: 0.571 msec |
| | Method: Scan 284 times = 9.5 min |

Building Block to be Used in Examples 1 and 2
4-[(4-tert-Butylphenylamino)methyl]benzoic Acid Methyl Ester 4-Formylbenzoic acid methyl ester (10.6 g, 64 mmol) was dissolved in methanol (200 ml). 4-tert-Butylaniline (9.61 g, 64 mmol) was added and the resulting suspension was refluxed for 15 minutes. After cooling to room temperature, TFA (5.18 ml, 68 mmol) was added followed by portion wise addition of sodium cyanoborohydride (3.26 g, 52 mmol). The resulting mixture was stirred at room temperature for 2 hours and concentrated in vacuo. The residue was partitioned between ethyl acetate (200 ml) and 1N aqueous sodium hydroxide (150 and 100 ml). The organic phase was dried (magnesium sulphate) and evaporated in vacuo to afford 19.0 g (99%) of 4-[(4-tert-butylphenylamino)methyl]benzoic acid methyl ester as a solid.

$^1$H NMR (CDCl$_3$): δ 1.28 (9H, s), 3.92 (3H, s), 4.39 (2H, s), 6.57 (2H, d), 7.20 (2H, d), 7.44 (2H, d), 8.00 (2H, d).

Building Block to be Used in Example 12

Step A: 4-Cyclohex-1-enylaniline

This compound was prepared similarly as described in J. v. Braun et al., *J. Liebigs Ann. Chem.*, 472 (1929), 1–89, from refluxing aniline (2 equivalents), cyclohexanone (1 equivalent) in ethanol and 37% hydrochloric acid for 4–5 days, followed by addition of ethyl acetate, water, and sodium hydroxide, neutralisation with 85% phosphoric acid, phase separation, and distillation of the organic phase. The residue was added a catalytic amount of sulphuric acid and distilled (180° C., 5–7 mbar). The distillate was redistilled (120° C., 3 mbar) to afford (in the residue) a 49% yield of the desired 4-cyclohex-1-enylaniline.

$^1$H NMR (DMSO-$d_6$): δ 1.50–1.60 (m, 2H), 1.60–1.70 (m, 2H), 2.10–2.15 (m, 2H), 2.20–2.30 (brd s, 2H), 5.00 (s, 2H), 5.90 (t, 1H), 6.50 (d, 2H), 7.10 (d, 2H).

Step B: 4-[(4-Cyclohex-1-enylphenylamino)methyl]benzoic Acid Methyl Ester

To a solution of 4-cyclohexenylaniline (3,40 g, 0.023 mol) and methyl 4-formylbenzoate (3.77 g, 0.023 mol) in DCM (50 ml) and methanol (15 ml) was added a catalytic amount of acetic acid. After stirring the solution for 3 hours, Na(OAc)$_3$BH (24 g, 0.115 mol) was added. The reaction was allowed to stir at room temperature for 16 hours. The reaction mixture was diluted with ethyl acetate and washed with aqueous sodium bicarbonate (3×), brine (2×), dried over magnesium sulphate, filtered, and concentrated to give an orange solid. The crude product was introduced into a column of silica gel and eluted with ethyl acetate:hexane (5:95) to give 4-[(4-cyclohex-1-enylphenylamino)methyl] benzoic acid methyl ester (5 g, 0.015 mol).

$^1$H NMR (DMSO-$d_6$): δ 1.56 (m, 2H), 1.67 (m, 2H), 2.11 (m, 2H), 2.25 (m, 2H), 3.81 (s, 3H), 4.34 (d, 2H), 5.89 (t, 1H), 6.34 (t, 1H), 6.49 (d, 2H), 7.10 (d, 2H), 7.47 (2H, d), 7.90 (d, 2H); MS (APCl, pos): 322.1, 323.1.

Step C: 4-[3-(3,5-Dichlorophenyl-1-(cyclohex-1-enylphenyl)ureidomethyl]benzoic Acid Methyl Ester The above 4-[(4-cyclohex-1-enylphenylamino)methyl] benzoic acid methyl ester (5 g, 0.015 mol) was dissolved in anhydrous DCM and diisopropylethylamine (5.8 g, 0.045 mol) was added. To this solution was added an isocyanate (eg 3,5-dichlorophenylisocyanate) (0.018 mol). After stirring the reaction mixture for 3 hours, the solution was diluted with ethyl acetate and washed with 1 N hydrochloric acid (2×), water, brine, dried over magnesium sulphate, filtered, and concentrated under reduced pressure. The residue was introduced into a silica gel column and eluted with ethyl acetate:hexane (10:90) to give 4-[3-(3,5-dichlorophenyl-1-(cyclohex-1-enylphenyl)ureidomethyl] benzoic acid methyl ester (4 g).

$^1$H NMR (DMSO-$d_6$): δ 1.58 (m, 2H); 1.70 (m, 2H); 2.16 (m, 2H); 2.32 (m, 2H); 3.71 (s, 3H); 4.98 (s, 2H); 6.18 (t, 1H); 7.12 (s, 1H); 7.20 (d, 2H); 7.39 (d, 2H); 7.41 (d, 2H); 7.62 (s, 2H); 7.89 (d, 2H); 8.56 (s, 1H); MS (APCl, pos): 509.0. 510.0, 511.1.

General Procedure A

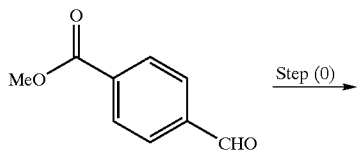

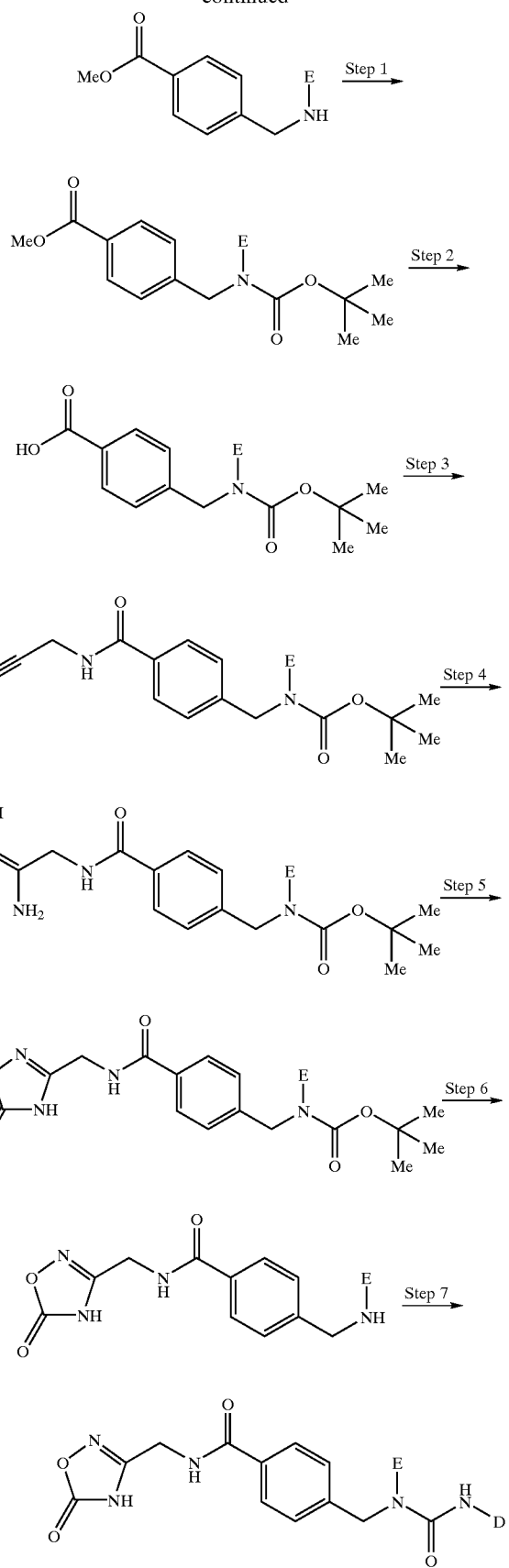

Example 1

General Procedure (A)
4-[1-(4-tert-Butylphenyl)-3-(4-trifluoromethoxyphenyl) ureidomethyl]-N-5-oxo-4,5-dihydro-[1,2,4]oxadiazol-3-ylmethyl)benzamide

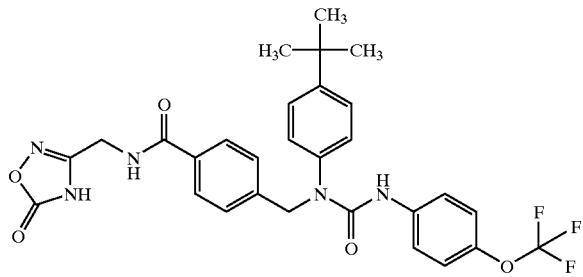

Step 1: 4-{[tert-Butoxycarbonyl-(4-tert-butylphenylamino] methyl}benzoic Acid Methyl Ester

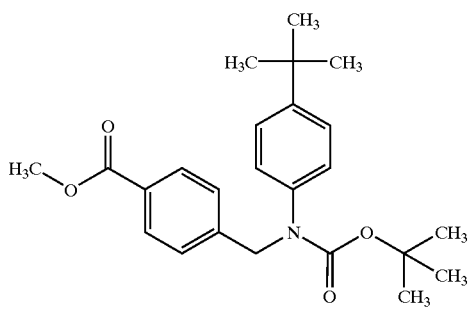

4-[(4-tert-Butylphenylamino)methyl]benzoic acid methyl ester (5 g, 16.8 mmol) was dissolved in a mixture of THF (10 ml) and aqueous sodium hydroxide (1 N, 16.8 ml). A solution of di-tert-butylpyrocarbonate in THF (20 ml) was added dropwise, and the mixture was stirred at room temperature for 16 hours. The reaction mixture was concentrated in vacuo and ethyl acetate (150 ml), water (50 ml) and hydrochloric acid (4 N, 8.4 ml) were added. The aqueous phase was extracted with ethyl acetate (25 ml). The combined organic phases were washed with water (3×30 ml), dried (magnesium sulphate) and concentrated in vacuo to afford 6.9 g of 4-{[tert-butoxycarbonyl-(4-tert-butylphenyl-amino)]methyl}benzoic acid methyl ester.

$^1$H NMR (DMSO-d$_6$): δ 1.25 (s, 9H); 1.37 (s, 9H); 3.34 (s, 3H); 3.84 (s, 2H); 4.90 (s, 1H); 7.13–7.19 (d, 2H); 7.3–7.4 (dd, 4H); 7.9–7.96 (d, 2H).

Step 2: 4-{[tert-Butoxycarbonyl-(4-tert-butylphenyl)amino] methyl}benzoic Acid

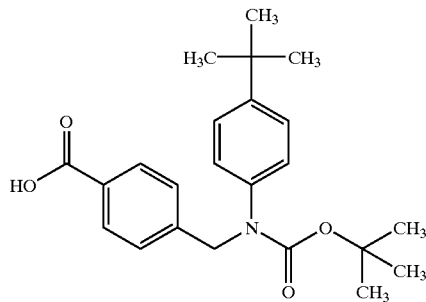

4-{[tert-Butoxycarbonyl-(4-tert-butylphenylamino] methyl}benzoic acid methyl ester (6.9 g, 17.4 mmol) was suspended in a mixture of ethanol (96%, 80 ml) and aqueous sodium hydroxide (4 N, 17 ml) and stirred at room temperature for 16 hours. The reaction mixture was concentrated in vacuo, and the residue was dissolved in water (50 ml), acidified with hydrochloric acid (4 N, 14 ml), and extracted with ethyl acetate (50 ml). The aqueous phase was extracted with ethyl acetate (50 ml). The combined organic phases were washed with water (3×30 ml), dried (magnesium sulphate) and concentrated in vacuo. The residue was crystallised from ethyl acetate:n-heptane to give 4.11 g of 4-{[tert-butoxycarbonyl-(4-tert-butylphenyl)amino]methyl}benzoic acid.

$^1$H NMR (DMSO-d$_6$): δ 1.24 (s, 9H); 1.35 (s, 9H); 4.88 (2H); 7.10–7.18 (d, 2H); 7.28–7.36 (dd, 4H); 7.85–7.93 (d, 2H); 12.90 (broad, 1H).

Step 3: N-(4-tert-Butylphenyl)-N-[4-(cyanomethylcarba-moyl)benzyl]carbamic Acid tert-Butyl Ester

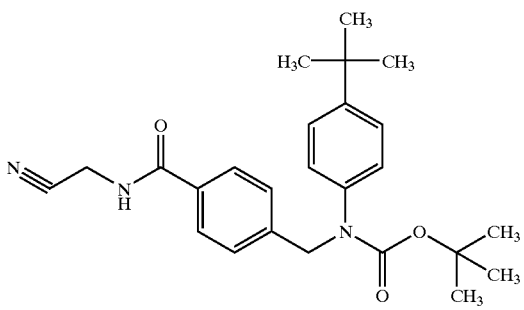

4-{[tert-Butoxycarbonyl-(4-tert-butylphenyl)amino] methyl}benzoic acid (4.1 g, 10.7mmol) was dissolved in DMF (40 ml). Hydroxybenzotriazole (1.59 g, 11.8 mmol) and EDAC (2.25 g, 1.8 mmol) were added and the reaction mixture was stirred at room temperature for 30 min. Aminoacetonitrile hydrochloride (1.38 g, 15 mmol) and diisopropylethylamine (2.55 ml, 15 mmol) were added and the reaction mixture was stirred at room temperature for 16 hours. The reaction mixture was diluted with ethyl acetate (150 ml) and extracted with water (125 ml). The aqueous phase was extracted with ethyl acetate (50 ml). The combined organic phases were washed with hydrochloric acid (0.2 N, 3×50 ml) and a mixture of water and saturated sodium chloride (1:1, 3×50 ml), dried (magnesium sulphate) and concentrated in vacuo. The residue was purified by column chromatography on silica gel (150 g) using ethyl acetate/n-heptane (3:7) as eluent to afford 3.8 g of N-(4-tert-butylphenyl)-N-[4-(cyano-methylcarbamoyl)benzyl] carbamic acid tert-butyl ester.

$^1$H NMR (DMSO-d$_6$): δ 1.25 (9H, s), 1.35 (9H, s), 4.3 (2H, d), 4.89 (2H, s), 7.15 (2H, d), 7.30–7.38 (4H, dd), 7.82 (2H, d), 9.15 (1H, t); HPLC-MS (Method A): m/z: 422; R$_t$=7.50 min.

Step 4: N-(4-tert-Butylphenyl)-N-{4-[(N-hydroxyamidino-methyl)carbamoyl]benzyl}-carbamic Acid tert-Butyl Ester

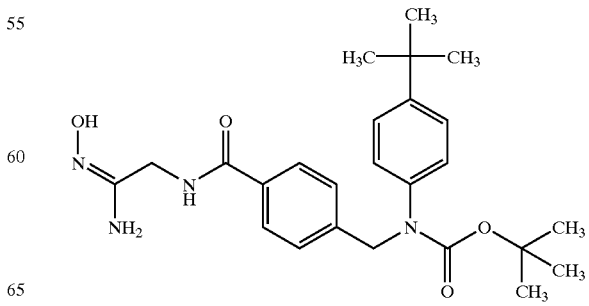

Triethylamine (2.29 g, 22.6 mmol) was added to a solution of hydroxylamine hydrochloride (1.57 g, 22.6 mmol) in DMSO (7 ml). After 10 min, the mixture was filtered and the filter was washed with THF. The combined filtrates were concentrated in vacuo. N-(4-tert-butylphenyl)-[4-(cyanomethylcarbamoyl)benzyl]carbamic acid tert-butyl ester (1.9 g, 4.5 mmol) was added to the DMSO solution containing the hydroxylamine, and the reaction mixture was stirred at 85° C. for 16 hours. The reaction mixture was diluted with ethyl acetate (50 ml) and water (20 ml). The organic phase was extracted with hydrochloric acid (1 N, 9 ml) and water (2×20 ml), dried (magnesium sulphate) and concentrated in vacuo. The residue was crystallised from heptane and ethyl acetate to afford 1.02 g of N-(4-tert-butylphenyl)-N-{4-[(N-hydroxyamidinomethyl)carbamoyl]benzyl}carbamic acid tert-butyl ester. M.p. 154–156° C.

$^1$H NMR (DMSO-$d_6$): δ 1.22 (9H, s), 1.39 (9H, s), 4.21 (2H, d), 4.89 (2H, s), 7.12 (2H, d), 7.32 (4H, dd), 7.88 (2H, d), 9.05 (1H, t), 10.80 (1H, s), 12.50 (1H, broad); HPLC-MS (Method A): m/z: 455; $R_t$=5.55 min.

Microanalysis: Calculated for $C_{25}H_{35}Cl_1N_4O_4$: C, 61.15%; H, 7.18%; N, 11.41%. Found: C, 61.52%; H, 7.39%; N, 11.16%.

Step 5: N-(4-tert-Butylphenyl)-N-{4-[5-oxo-4,5-dihydro-[1,2,4]oxadiazol-3-ylmethyl)-carbamoyl]benzyl}carbamic Acid tert-Butyl Ester

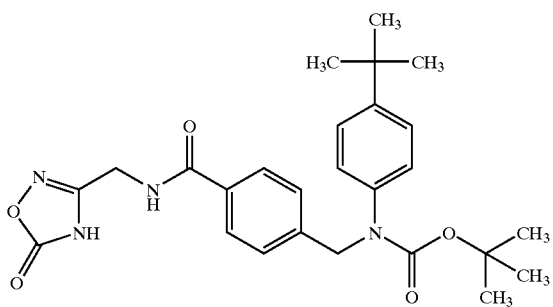

2-Ethylhexyl chloroformate (0.34 g, 1.76 mmol) was added dropwise to a solution of N-(4-tert-butylphenyl)-N-{4-[(N-hydroxyamidinomethyl)carbamoyl]benzyl}-carbamic acid tert-butyl ester (0.80 g, 1.76 mmol) and pyridine (0.15 g, 1.90 mmol) in DMF (5 ml) keeping the temperature at 0° C. After 30 min at 0° C. the reaction mixture was diluted with ethyl acetate (25 ml) and water (10 ml). The organic phase was washed with water (5×10 ml), dried (magnesium sulphate) and concentrated in vacuo. The residue was dissolved in m-xylene (10 ml) and refluxed for 2 hours. The reaction mixture was concentrated in vacuo and the residue was purified by column chromatography on silica gel (33 g) eluting with a mixture of ethyl acetate and heptane (7:3) to afford 0.31 g of N-(4-tert-butylphenyl)-N-{4-[5-oxo-4,5-dihydro-[1,2,4]-oxadiazol-3-ylmethyl)carbamoyl]benzyl}carbamic acid tert-butyl ester.

$^1$H NMR (DMSO-$d_6$): δ 1.22 (9H, s), 1.39 (9H, s), 4.38 (2H, d), 4.88 (2H, s), 7.12 (2H, d), 7.30 (4H, dd), 7.82 (2H, d), 9.00 (1H, t), 12.40 (1H, broad); HPLC-MS (Method B): m/z=381 (M+1); $R_t$=7.10 min.

Step 6: 4-[(4-tert-Butylphenylamino)methyl]-N-(5-oxo-4,5-dihydro-[1,2,4]oxadiazol-3-ylmethyl)benzamide

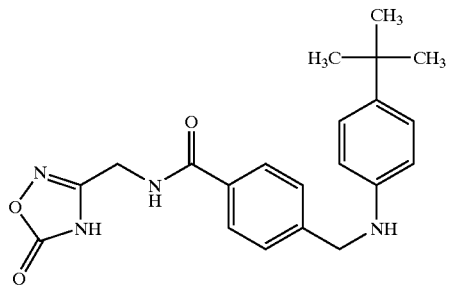

N-(4-tert-Butylphenyl)-N-{4-[5-oxo-4,5-dihydro-[1,2,4]oxadiazol-3-ylmethyl)-carbamoyl]benzyl}carbamic acid tert-butyl ester (0.20 g, 0.45 mmol) was suspended in ethyl acetate (4 ml) and dry hydrogen chloride in ethyl acetate (3 M, 4 ml) was added. After 2.5 hours at 40° C. the reaction mixture was concentrated in vacuo and the residue was crystallised from ethyl acetate to afford 0.15 g of 4-[(4-tert-butyl-phenylamino)methyl]-N-(5-oxo-4,5-dihydro-[1,2,4]oxadiazol-3-ylmethyl)benzamide hydrochloride.

$^1$H NMR (DMSO-$d_6$): δ 1.22 (9H, s), 4.39 (2H, d), 4.48 (2H, s), 7.05 (2H, broad), 7.31 (2H, d), 7.55 (2H, d), 7.86 (2H, d), 9.05 (1H, t), 12.45 (1H, broad); HPLC-MS (Method A): m/z: 355; $R_t$=4.23 min; HPLC-MS (Method B): m/z= 381 (M+1); $R_t$=4.77 min.

Step 7:

To a solution of 4-[(4-tert-butylphenylamino)methyl]-N-(5-oxo-4,5-dihydro-[1,2,4]oxadiazol-3-ylmethyl)benzamide hydrochloride (100 mg, 0.26 mmol) and diisopropylethylamine (33.6 mg, 0.26 mmol) in acetonitrile (5 ml) was added 4-(trifluoromethoxy)phenylisocyanate (52.8 mg, 0.26 mmol). The reaction mixture was stirred for 4.5 hours at 20° C. and concentrated in vacuo. The residue was purified by column chromatography on silica gel (33 g) eluting with a mixture of DCM and 10% ammonia in ethanol (85:15) to afford 100 mg of the title compound.

$^1$H NMR (DMSO-$d_6$): δ 1.25 (9H, s), 4.34 (2H, d), 4.96 (2H, s), 7.15–7.28 (4H, dd), 7.38 (4H, d), 7.55 (2H, d), 7.82 (2H, d), 8.45 (1H, s), 8.95 (1H, t); HPLC-MS (Method A): m/z: 584; $R_t$=7.37 min.

Example 2

General Procedure (A)

4-[1-(4-tert-Butylphenyl)-3-(3-fluoro-5-trifluoromethyl-phenyl)ureidomethyl]-N-(5-oxo-4,5-dihydro[1,2,4]oxadiazol-3-ylmethyl)benzamide

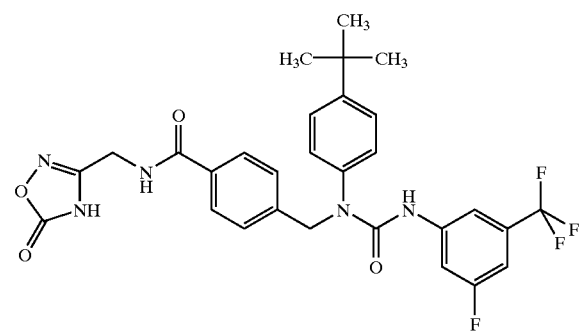

3-Amino-5-fluorobenzotrifluoride (70 mg, 0.34 mmol) was dissolved in ethyl acetate (1 ml) and dry hydrogen chloride in ethyl acetate (3.4 M, 3 ml) was added. After 10 min the mixture was concentrated in vacuo and the residue was evaporated from toluene three times (4 ml). The residue was suspended in toluene (4 ml) and diphosgene (0.20 ml, 1.7 mmol) was added. The reaction mixture was stirred at 120° C. for 3 hours and concentrated in vacuo. The residue was evaporated from toluene three times (4 ml). The residue was dissolved in DCM (1 ml) and added to a solution of 4-[(4-tert-butylphenylamino)methyl]-N-(5-oxo-4,5-dihydro-[1,2,4]oxadiazol-3-yl-methyl)benzamide hydrochloride (130 mg, 0.31 mmol) and diisopropylethylamine (44 mg, 0.34 mmol) in DCM (2 ml). The reaction mixture was stirred for 16 hours at 20° C. and concentrated in vacuo. The residue was purified by column chromatography on silica gel (33 g) using a mixture of DCM and 10% ammonia in ethanol (7:3) to afford 54 mg of the title compound.

$^1$H NMR (DMSO-$d_6$): δ 1.25 (9H, s), 4.20 (2H, d), 4.98 (2H, s), 7.16–7.26 (4H, dd), 7.35–7.43 (4H, dd), 7,73 (1H, s), 7.82 (2H, d), 8.8 (1H, s); HPLC-MS (Method A): m/z: 586; $R_t$=7.48 min.

General Procedure (B)

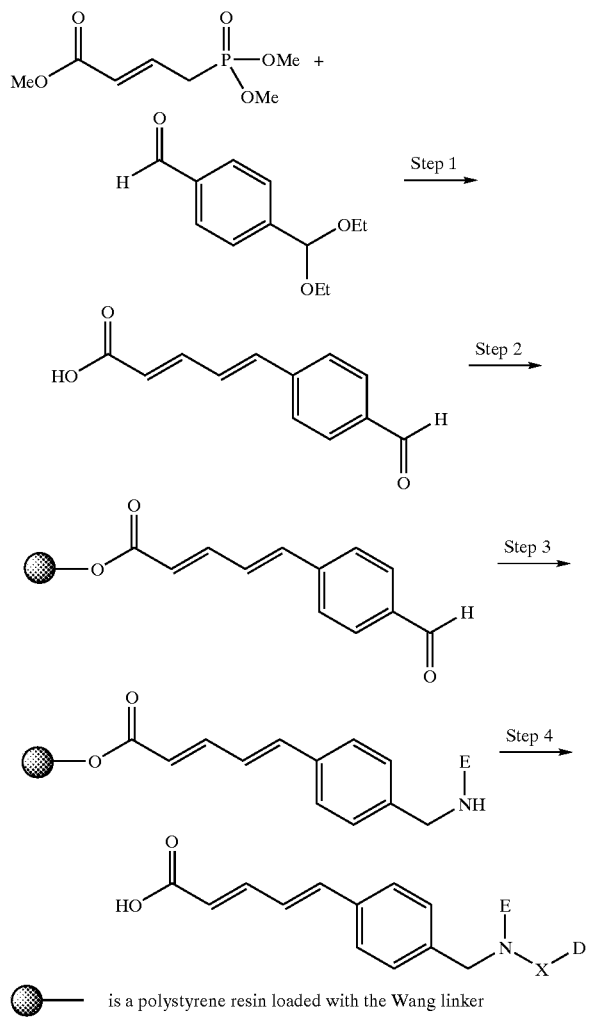

○ is a polystyrene resin loaded with the Wang linker wherein X is —C(O)NH—, —C(O)NHCH$_2$—, —C(O)NHCH(CH$_3$)—, —C(O)NHCH$_2$CH$_2$— or —C(O)O—, and D and E are as defined for formula (I).

The procedure is illustrated in example 3 below.

Example 3

General Procedure (B)

5-{4-[1-(4-tert-Butylphenyl)-3-(2,2,4,4-tetrafluoro-4H-benzo[1,3]dioxin-6-yl)ureidomethyl]phenyl}penta-2,4-dienoic Acid

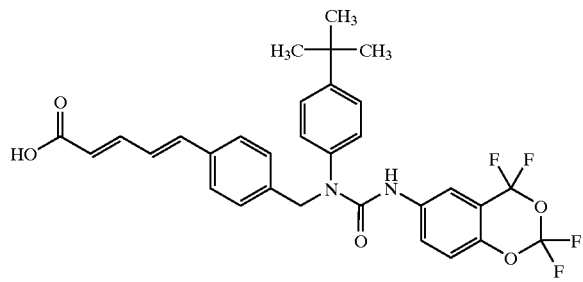

Step 1: Preparation of 5-(4-Formylphenyl)penta-2,4-dienoic Acid

To an ice cooled solution of sodium hydride (2.26 g, 67.2 mmol as a 60% mineral oil suspension) in dry THF (100 ml) was added dropwise a solution of trimethyl4-phosphonocrotonate (10.5 g, 50.4 mmol) in dry THF (200 ml), and the solution was stirred under an inert atmosphere at 0° C. for 3 hours. Terephthaldialdehyde mono diethyl acetal (7.00 g, 33.6 mmol) was dissolved in dry THF (200 ml) and slowly added to the above solution. Stirring was continued for 2 hours at 0° C. Water (400 ml) was slowly added, and followed by ethyl acetate (500 ml) and the layers were mixed. The organic layer was collected and dried with anhydrous sodium sulphate. Solvent was removed by rotary evaporation to leave 10.0 g of a crude orange product that was dissolved in ethanol (20 ml) and added a solution of 20% potassium hydroxide (100 ml). The mixture was stirred at room temperature for 5 hours, and then partitioned between ethyl acetate (500 ml) and water (500 ml). The organic layer was washed with water (200 ml), and the combined water phases back extracted once with ethyl acetate (300 ml). The water phase was acidified with glacial acetic acid to pH 3.5, and extracted with ethyl acetate (2×500 ml). The organic layer was dried with sodium sulphate, and taken to dryness to leave the title material as an orange powder. Yield: 6.78 g (100%).

$^1$H NMR (DMSO-$d_6$): δ 12.35 (s, 1H); 9.98 (s, 1H); 7.90 (d, 2H); 7.77 (d, 2H); 7.38 (d, 1H); 7.30 (d, 1H); 7.15 (d, 1H); 6.08 (d, 1H). HPLC-MS (Method B): m/z=203 (M+1); $R_t$=2.71 min.

Step 2: Preparation of Resin Bound 5-(4-Formylphenyl)penta-2,4-dienoic Acid 5-(4-Formylphenyl)penta-2,4-dienoic acid (510 mg, 2.52 mmol) was suspended in ethanol (5 ml), and water (1.3 ml) was added followed by solid cesium carbonate (684 mg, 2.1 mmol). The mixture was stirred at room temperature for 30 min and then taken to dryness. The cesium salt was re-suspended in DMF (25 ml) and potassium iodide (35 mg, 0.21 mmol) was added. This suspension was then added to bromo-wang resin (2.0 g, loading 1.05 mmol/g). The reaction mixture was shaken at 50° C. overnight, then drained and washed with DMF (2×30 ml); water:DMF (2×30 ml), DMF (2×30 ml) and DCM (3×30 ml). Resin was dried overnight in a vacuum oven at 40° C.

Step 3: Preparation of Resin Bound 5-{4-[(4-tert-Butylphenylamino)methyl]phenyl}-penta-2,4-dienoic Acid Resin linked 5-(4-formylphenyl)penta-2,4-dienoic acid (50 mg) was suspended in NMP:DCP (2 ml, 1:1) for 30 min, then washed with DMF (3×2 ml). The solvent was removed, and a solution of tert-butylaniline (30 mg, 0.2 mmol) in DMF:TMOF (1.5 ml, 1:1) was added followed by HOAc (100 μl). The mixture was stirred at 2 hours at room temperature, before adding a solution of sodium cyanoborohydride (11 mg, 0.15 mmol) in DMF-MeOH (1 ml, 1:1). The mixture was stirred overnight at room temperature, then drained for solvent and washed with DMF (3×2 ml) and DCM (2 ml). A solution of 50% DIPEA in DCM (2 ml) was added and the resin was left stirring for 30 min. The resin was subsequently washed with DCM (3×2 ml), MeOH (1×2 ml) and DCP (2×2 ml).

Step 4: Preparation of 5-{4-[1-(4-tert-Butylphenyl)-3-(2,2,4,4-tetrafluoro-4H-benzo-[1,3]dioxin-6-yl)ureidomethyl]phenyl}penta-2,4-dienoic Acid To the above prepared resin was added a solution of 2,2,4,4-tetrafluoro-6-isocyanato-4H-benzo[1,3]dioxine (124 mg, 0.5 mmol) in DCP (1 ml). The solution was shaken overnight at room temperature, and then washed with DMF (3×2 ml) and DCM (10×2 ml). The title product was cleaved from resin by treating the resin with a 50% solution of TFA in DCM (2 ml 1:1) for 40 min. Solvent was removed by nitrogen air-flow to leave the title material as a crystalline solid.

HPLC-MS (Method B): m/z=586 (M+1); $R_t$=8.23 min.

In a similar way the following compounds were prepared:

Example 4

General Procedure (B)

5-{4-[3-(3,5-bis(Trifluoromethyl)phenyl)-1-(4-tert-butylphenyl)ureidomethyl]phenyl}-penta-2,4-dienoic Acid

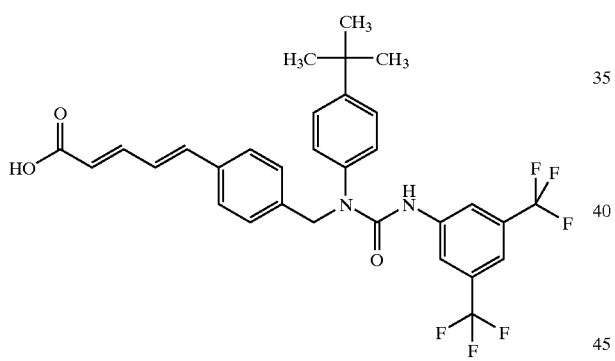

HPLC-MS (Method B): m/z=591 (M+1); $R_t$=8.38 min.

Example 5

(General Procedure (B))

5-{4-[3-[1-(4-Bromophenyl)ethyl]-1-(4-tert-butylphenyl)ureidomethyl]phenyl}penta-2,4-dienoic Acid

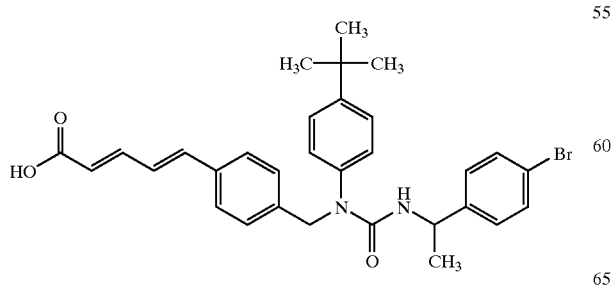

HPLC-MS (Method B): m/z=562 (M+1); $R_t$=7.78 min.

Example 6

General Procedure (B)

5-{4-[1-(4-tert-Butylcyclohexyl)-3-(2,2,4,4-tetrafluoro-4H-benzo[1,3]dioxin-6-yl)ureidomethyl]phenyl}penta-2,4-dienoic Acid

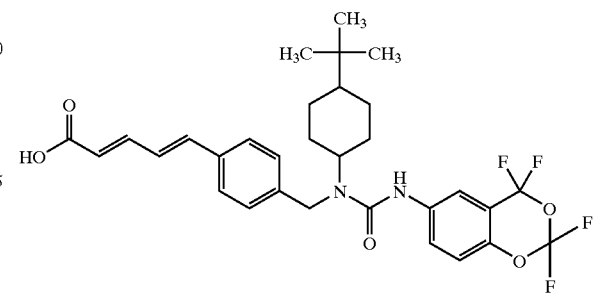

HPLC-MS (Method B): m/z=591 (M+1); $R_t$=8.20 min.

Example 7

(General Procedure (B))

5-{4-[3-(3,5-bis(Trifluoromethyl)phenyl)-1-(4-tert-butylcyclohexyl)ureidomethyl]-phenyl}penta-2,4-dienoic Acid

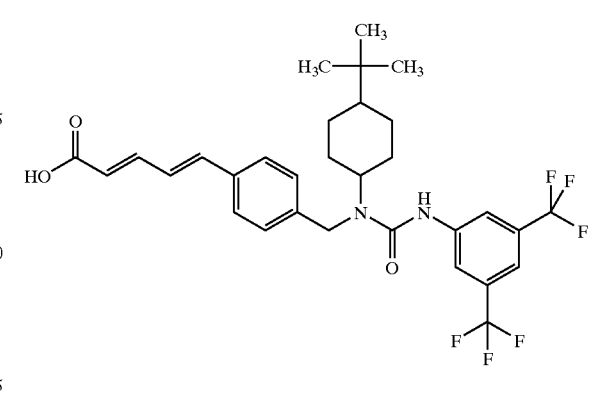

HPLC-MS (Method B): m/z=597 (M+1); $R_t$=8.87 min.

Example 8

(General Procedure (B))

5-{4-[3-[1-(4-Bromophenyl)ethyl]-1-(4-tert-butylcyclohexyl)ureidomethyl]phenyl}penta-2,4-dienoic Acid

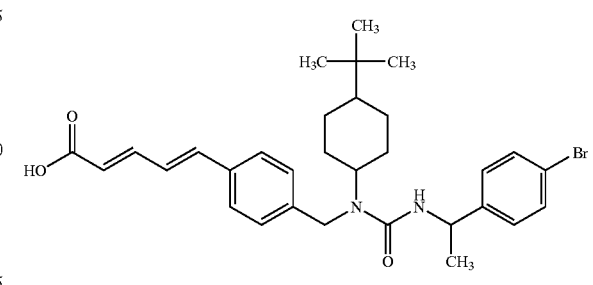

HPLC-MS (Method B): m/z=568 (M+1); $R_t$=8.23 min.

Example 9

(General Procedure (B))

5-{4-[1-(4-Cyclohex-1-enylphenyl)-3-(2,2,4,4-tetrafluoro-4H-benzo[1,3]dioxin-6-yl)-ureidomethyl]phenyl}penta-2,4-dienoic Acid

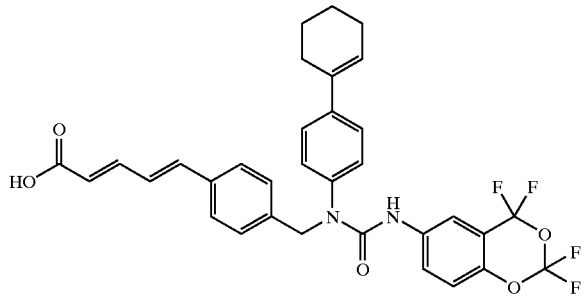

HPLC-MS (Method B): m/z=609 (M+1); $R_t$=8.42 min.

Example 10

(General Procedure (B))

5-{4-[3-(3,5-bis(Trifluoromethyl)phenyl)-1-(4-cyclohex-1-enylphenyl)ureidomethyl]-phenyl}penta-2,4-dienoic Acid

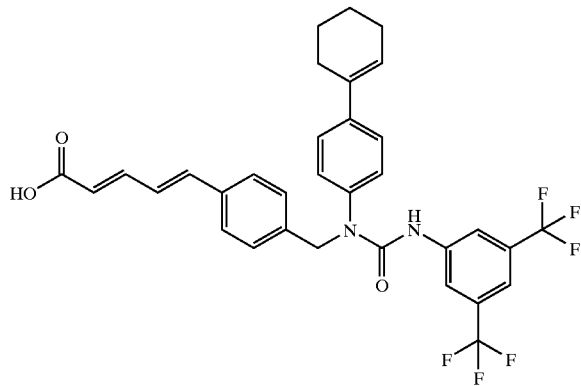

HPLC-MS (Method B): m/z=615 (M+1), $R_t$=8.70 min.

Example 11

(General Procedure (B))

5-{4-[3-[1-(4-Bromophenyl)ethyl]-1-(4-cyclohex-1-enylphenyl)ureidomethyl]-phenyl}penta-2,4-dienoic Acid

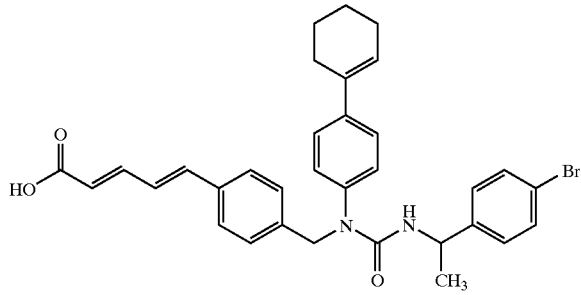

HPLC-MS (Method B): m/z 586 (M+1); $R_t$=8.22 min.

Example 12

5-{4-[1-(4-Cyclohex-1-enylphenyl)-3-(3,5-dichlorophenyl)ureidomethyl]phenyl}penta-2,4-dienoic Acid

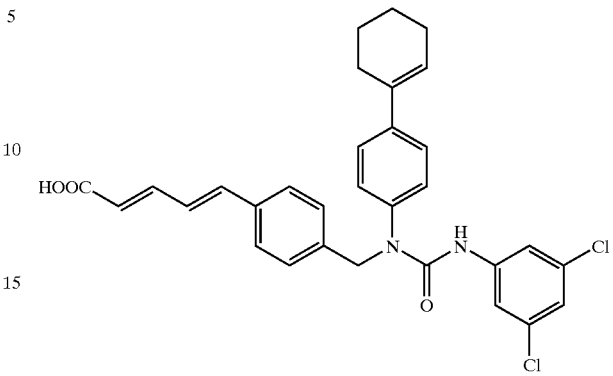

Step 1: 1-(4-Cyclohex-1-enylphenyl)-3-(3,5-dichlorophenyl)-1-(4-[hydroxymethyl]benzyl)urea 4-[1-(4-Cyclohex-1-enylphenyl)-3-(3,5-dichlorophenyl)ureidomethyl]benzoic acid methyl ester (20 g; 39 mmol) was dissolved in toluene (750 mnl) and the solution was cooled to −78° C. A solution of diisobutyl aluminium hydride (163 ml; 1.2 M in toluene) was added dropwise while maintaining the temperature below −65° C. The mixture was stirred for 40 minutes at −78° C. and for 3 hours at room temperature. The mixture was neutralised with 1 N hydrochloric acid in ether (200 ml), before adding water (750 ml). The organic layer was separated, dried with anhydrous sodium sulphate and taken to dryness by rotary evaporation in vacuo, to give 1-(4-cyclohex-1-enylphenyl)-3-(3,5-dichlorophenyl)-1-(4-[hydroxymethyl]benzyl)urea. Yield: 18.0 g (96%).

$^1$H NMR (DMSO-$d_6$): δ 8.50 (s, 1H); 7.61 (d, 2H); 7.38 (d, 2H); 7.22 (d, 2H); 7.20–7.10 (m, 5H). 6.18 (m, 1H); 5.12 (t, 1H); 4.89 (s, 2H); 4.45 (d, 2H); 2.34 (m, 2H); 2.15 (m, 2H); 1.70 (M, 2H); 1.58 (m, 2H).

Step 2: 1-(4-Cyclohex-1-enylphenyl)-3-(3,5-dichlorophenyl)-1-(4-formylbenzyl)urea 1-(4-Cyclohex-1-enylphenyl)-3-(3,5-dichlorophenyl)-1-(4-[hydroxymethyl]-benzyl)urea (10.0 g; 20.8 mmol) was dissolved in DCM (200 ml) and pyridinium dichromate was added (15.6 g, 41.5 mmol). The mixture was stirred at ambient temperature until judged completed (7 hours) by TLC (ethyl acetate/heptane (50:50), $R_f$=0.6). Insoluble material was filtered off, and solvent was removed by rotary evaporation to leave an oil. The oil was dissolved in hot ethyl acetate (400 ml). After filtration, the solvent was reduced to half its volume by rotary evaporation in vacuo. The solution was then chilled on an ice-bath to initiate crystallization. The product was filtered off and washed with cold ethyl acetate. A second crop of crystals was obtained by reducing the volume of the mother liquid, cool, and filter off precipitated crystals. Total yield of 1-(4-cyclohex-1-enylphenyl)-3-(3,5-dichlorophenyl)-1-(4-formylbenzyl)urea was 6.20 g (62%).

$^1$H NMR (DMSO-$d_6$): δ 9.95 (s, 1H); 8.60 (s, 1H); 7.86 (d, 2H); 7.62 (s, 2H); 7.50 (d, 2H); 7.41 (d, 2H); 7.21 (d, 2H); 7.15 (s, 1H); 6.20 (s, 1H); 5.01 (s, 2H) 2.35 (m, 2H); 2.18 (m, 2H); 1.70 (m, 2H); 1.60 (m, 2H).

Triethyl 4-phosphonocrotonate (145 mg; 0.65 mmol) was dissolved in dry THF (2.0 ml) and sodium hydride (50 mg; 60% oil suspension, 1.24 mmol) was added. The mixture was stirred a 0° C. for 10 minutes before introducing a solution of 1-(4-cyclohex-1-enylphenyl)-3-(3,5- dichlorophenyl)-1-(4-formylbenzyl)urea (150 mg; 0.31 mmol) in THF (2.0 ml). The solution was stirred at 0° C. for 1 hour. Water (1 ml) was added and stirring was continued for further 30 min at room temperature. Solvent was removed by rotary evaporation, and the residual oil was dissolved in water (5 ml). The title compound was precipitated out of solution by addition of acetic acid (1.0 ml), collected by filtration and washed with water. Yield: 150 mg.

$^1$H NMR (DMSO-d$_6$): δ 12.40 (bs, 1H); 8.50 (s, 1H); 7.57 (s, 2H); 7.40 (d, 2H); 7.38 (d, 2H); 7.24 (d, 2H); 7.20 (s, 1H); 7.15 (d, 2H); 7.10 (d, 1H); 7.05 (s, 1H); 7.01 (s, 1H); 6.18 (s, 1H); 5.95 (d, 1H); 4.90 (s, 2H); 2.35 (m, 2H); 2.20 (m, 2H); 1.70 (m, 2H); 1.55 (m, 2H); HPLC-MS (method B): m/z=547 (M+1); R$_t$=6.14 min.

General Procedure (C)

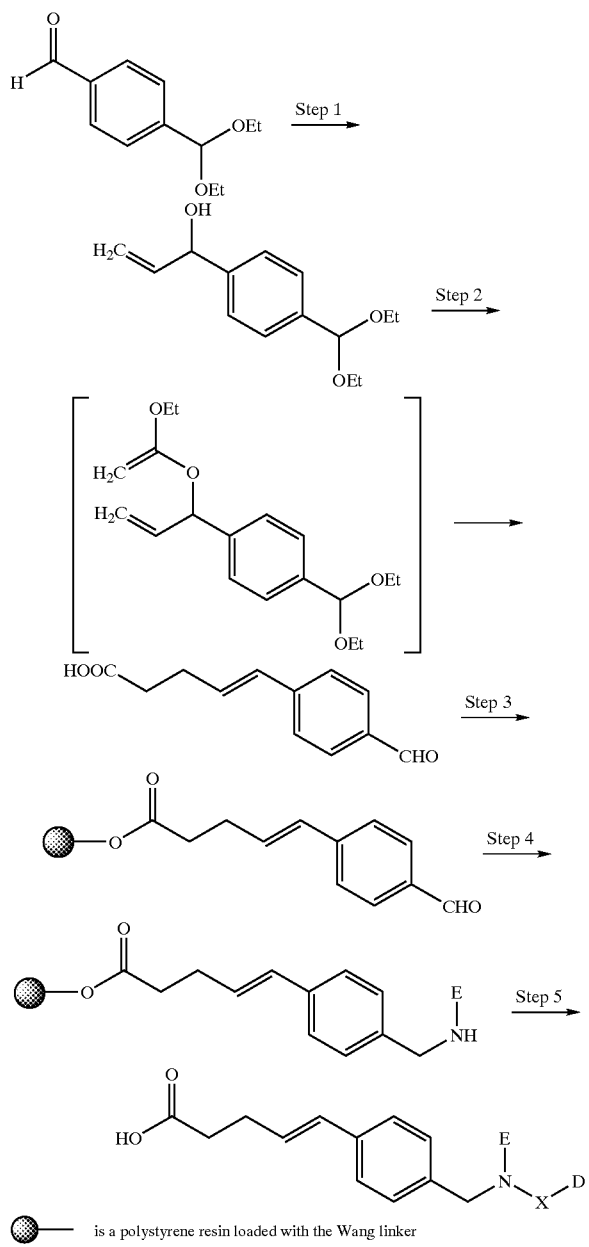

○ is a polystyrene resin loaded with the Wang linker wherein X is —C(O)NH—, —C(O)NHCH$_2$—, —C(O)NHCH(CH$_3$)— or —C(O)NHCH$_2$CH$_2$— and D and E are as defined for formula (I).

Example 13

General Procedure (C)
5-{4-[1-(4-tert-Butylphenyl)-3-(4-trifluoromethoxyphenyl)ureidomethyl]phenyl}penta-4-enoic Acid

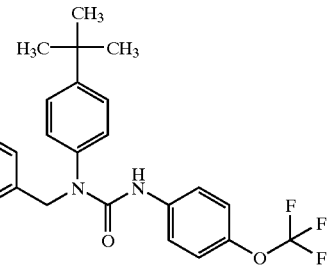

Step 1: 1-(4-Diethoxymethylphenyl)prop-2-en-1-ol

To an ice-cooled solution of terephthaldialdehyde monodiethylacetal (9.95 ml, 50 mmol) in THF (100 ml) was added dropwise a solution of vinyl magnesium bromide in THF (55 ml, 1 M, 55 mmol) at such rate, that the internal reaction temperature did not exceed 10° C. After addition, the solution was stirred at room temperature for 2 hours, before slow quenching with a saturated solution of aqueous ammonium chloride (100 ml). Water (100 ml) and ethyl acetate (200 ml) was added, and the two-phase system was stirred vigorously for 10 min. The organic phase was separated, washed once with saturated aqueous ammonium chloride (100 ml), dried over anhydrous sodium sulphate and then evaporated to dryness. The crude product was further purified by silica gel column chromatography using 25% ethyl acetate in heptane as eluent. Pure fractions were pooled and evaporated to dryness to give the title material as faint yellow oil. Yield: 3.60 g (31%).

$^1$H NMR (CDCl$_3$): δ 7.45 (d, 2H); 7.34 (d, 2H); 6.02 (m, 1H); 5.48 (s, 1H); 5.35 (d, 1H); 5.18 (s, 1H); 5.16 (d, 1H); 3.55 (m, 4H); 1.20 (t, 6H).

Step 2: 5-(4-Formylphenyl)pent-4-enoic Acid 1-(4-Diethoxymethylphenyl)prop-2-en-1-ol (9.90 g, 42 mmol) was dissolved in triethyl ortho formiate (50 ml), and propionic acid (1.0 ml) was added. The solution was heated to 140° C. for 48 hours. Solvent was removed by rotary evaporation, and the orange oil was re-suspended in aqueous HCl (200 ml, 2 N). The mixture was heated to reflux for 4 hours, then cooled on an ice-bath for 30 min. Precipitated material was collected and washed twice with water and dried in a vacuum oven. Yield: 3.02 g (35%).

$^1$H NMR (CDCl$_3$): δ 12.10 (s, 1H); 9.93 (s, 1H); 7.82 (d, 2H); 7.60 (d, 2H); 6.53 (ds, 2H); 2.55 (m, 2H); 2.50 (m, 2H).

Step 3: Preparation of Resin Bound 5-(4-Formylphenyl)pent-4-enoic Acid 5-(4-Formylphenyl)penta-4-enoic acid (700 mg, 3.40 mmol) was suspended in ethanol (8 ml), water (2 ml) was added followed by solid cesium carbonate (1095 mg, 3.36 mmol). The mixture was stirred at room temperature for 90 min after which a clear solution was obtained. Solvent was removed by rotary evaporation, and subsequently evaporated twice from dioxane. The cesium salt was re-suspended in DMF (30 ml) and potassium iodide (35 mg, 0.21 mmol) was added. This suspension was added to bromo-wang resin (2.8 g, loading 1.05 mmol/g). The reaction mixture was shaken at 50° C. overnight, then drained and washed with DMF (2×30 ml); water:DMF (2×30 ml, 1:1), DMF (2×30 ml) and DCM (3×30 ml). Resin was dried overnight in a vacuum oven at 40° C. to give 3.00 g of the product.

Step 4: Preparation of Resin Bound 5-{4-[(4-tert-Butylphenylamino)methyl]phenyl}-penta-4-enoic Acid Resin linked 5-(4-formylphenyl)penta-4-enoic acid (50 mg) was suspended in NMP:DCP (2 ml, 1:1) for 30 min and then washed with DMF (3×2 ml). The solvent was removed, and a solution of tert-butylaniline (30 mg, 0.2 mmol) in DMF-TMOF (1.5 ml, 1:1) was added followed by HOAc (100 μl). The mixture was stirred at 2 hours at room temperature, before adding a solution of sodium cyanoborohydride (11 mg, 0.15 mmol) in DMF:MeOH (1 ml, 1:1). The mixture was stirred overnight at room temperature, then drained for solvent and washed with DMF (3×2 ml) and DCM (2 ml). A solution of 50% DIPEA in DCM (2 ml) was added and the resin was left stirring for 30 min. The resin was subsequently washed with DCM (3×2 ml), MeOH (1×2 ml) and DCP (2×2 ml).

Step 5: Preparation of 5-{4-[1-(4-tert-Butylphenyl)-3-(4-trifluoromethoxyphenyl)-ureidomethyl]phenyl}penta-4-enoic Acid To the above prepared resin was added a solution of trifluoromethoxyphenyl isocyanate (101 mg, 0.5 mmol) in DCP (1 ml). The solution was shaken overnight at room temperature, and then washed with DMF (3×2 ml) and DCM (10×2 ml). The title product was cleaved from resin by treating the resin with a 50% solution of TFA in DCM (2 ml 1:1) for 40 min. Solvent was removed by nitrogen air-flow to leave the title material as a crystalline solid. HPLC-MS (Method B): m/z=541 (M+1); $R_t$=6.56 min.

In a similar way the following compounds were prepared.

Example 14

(General Procedure (C))
5-{4-[3-[1-(4-Bromophenyl)ethyl]-1-(4-tert-butylphenyl)ureidomethyl]phenyl}pent-4-enoic Acid

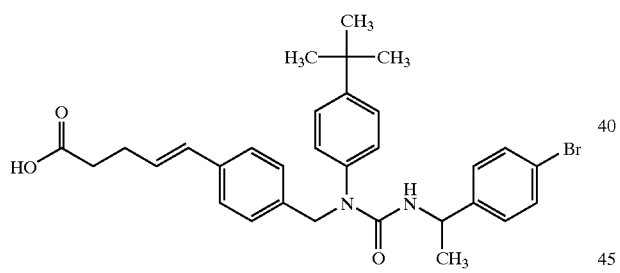

HPLC-MS (Method B): m/z=564 (M+1); $R_t$=6.39 min.

Example 15

(General Procedure (C))
5-{4-[1-(4-tert-Butylphenyl)-3-(3,5-dichlorophenyl)ureidomethyl]phenyl}pent-4-enoic Acid

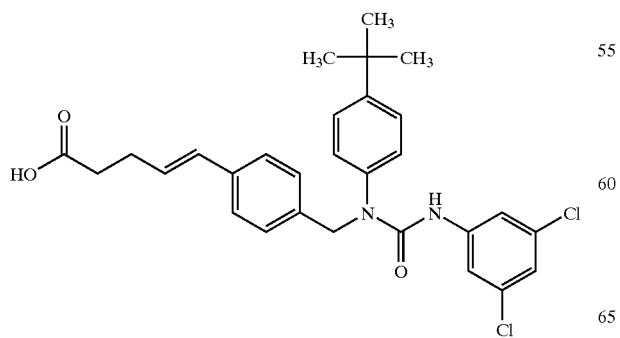

HPLC-MS (Method B): m/z=526 (M+1); $R_t$=6.95 min.

Example 16

(General Procedure (C))

5-{4-[1-(4-Cyclohex-1-enylphenyl)-3-(4-trifluoromethoxyPhenyl)ureidomethyl]phenyl}pent-4-enoic Acid

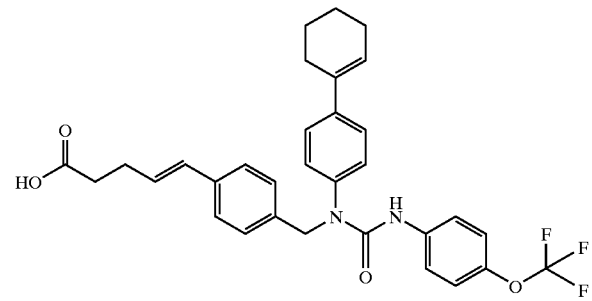

HPLC-MS (Method B): m/z=565 (M+1); $R_t$=6.90 min.

Example 17

(General Procedure (C))

5-{4-[1-(4-Cyclohex-1-enylphenyl)-3-(3,5-dichlorophenyl)ureidomethyl]phenyl}pent-4-enoic Acid

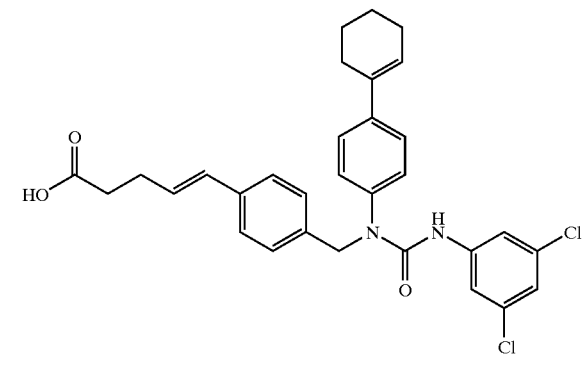

HPLC-MS (Method B): m/z=550 (M+1); $R_t$=7.33 min.

General Procedure (D)

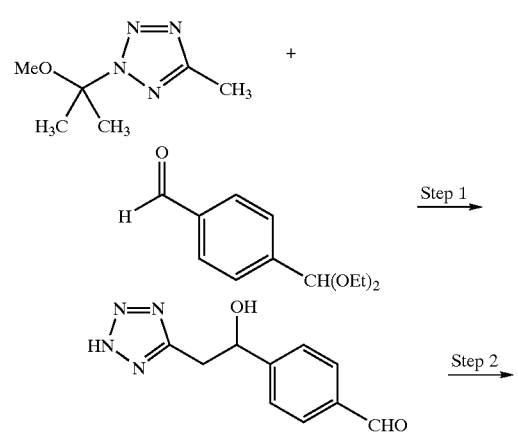

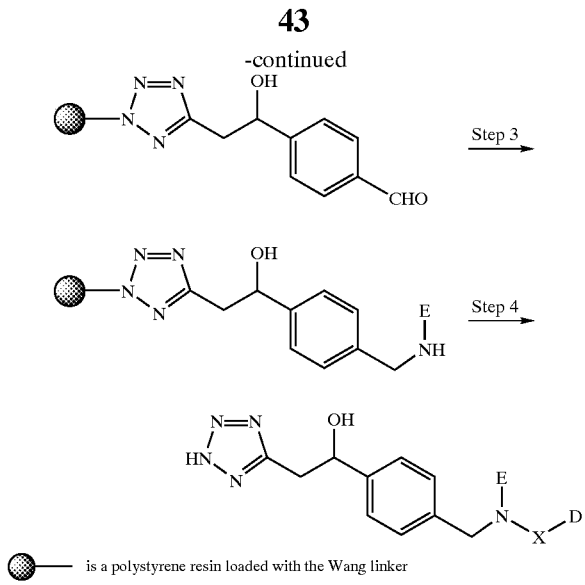

-continued

○— is a polystyrene resin loaded with the Wang linker wherein X is —C(O)NH—, —C(O)NHCH$_2$—, —C(O)NHCH(CH$_3$)— or —C(O)NHCH$_2$CH$_2$— and D and E are as defined for formula (I).

Example 18

(General Procedure (D))
3-(3,5-Bis(trifluoromethyl)phenyl)-1-(4-tert-butylcyclohexyl)-1-{4-[1-hydroxy-2-(2H-tetrazol-5-yl)ethyl]benzyl}urea

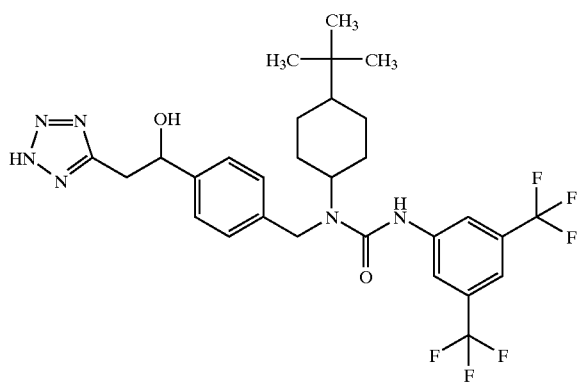

Starting Material for Step 1: 2-(1-Methoxy-1-methylethyl)-5-methyl-2H-tetrazole 5-methyl-2H-tetrazole (3.50 g; 42.2 mmol) is suspended in toluene (100 ml). 2,2-dimethoxypropane (20 ml) is added, and the mixture is heated for reflux for 3 h, to give a clear colorless solution. Solvent is removed, by rotary-evaporation to leave the title material as a colorless oil, which according to NMR contained 20% of the regioisomer. The crude product is used which out further purification.

$^1$H NMR (CDCl$_3$): δ 3.13 (s, 3H; minor isomer); 3.11 (s, 3H; major isomer); 2.72 (s, 3H, minor isomer); 2.57 (s, 3H; major isomer) 1.98 (s, 6H, major isomer); 1.92 (s, 6H, minor isomer).

Step 1: 4-[1-Hydroxy-2-(2H-tetrazol-5-yl)ethyl]benzaldehyde

To a solution of 2-(1-methoxy-1-methylethyl)-5-methyl-2H-tetrazole in dry THF (100 ml), cooled to −78° C. on dry-ice-acetone bath, was slowly added a solution of n-butyl lithium in hexanes (32 ml, 1.6 M) while maintaining the internal reaction temperature below −65° C. The temperature was allowed to rise to 0° C. over 40 min. The temperature was then lowered to −78° C., and a solution of terephthaldialdehyde mono-diethylacetal (6.8 ml, 34 mmol) in THF (100 ml) was added dropwise over 10 min, while the clear dark reacton mixture changed color from dark to yellow. Temperature was again raised to 0° C., and the mixture was quenched with acetic acid (4.3 ml). The mixture was stirred at room temperature for 5 hours and then partitioned between ethyl acetate (500 ml) and water (500 ml). The organic layer was washed once with water (500 ml), then in a row with 1 N aqueous sodium hydroxide (2×250 ml), 10% aqueous sodium sulphite solution (2×250 ml) and brine (250 ml). The organic phase was then dried with anhydrous sodium sulphate and taken to dryness by rotary evaporation. The residue was suspended in 1 N aqueous HCl (100 ml) and heated to reflux for 2 hours. The clear solution thus obtained was filtered while hot, then cooled and taken to dryness. The residue was stripped twice from acetonitrile to give pure title material as off-white crystals.

$^1$H NMR (DMSO-d$_6$): δ 9.96 (s, 1H); 7.88 (d, 2H); 7.57 (d, 2H); 5.09 (dd, 1H); 3.22 (ddd, 2H).

Step 2: Preparation of Resin Bound 4-[1-Hydroxy-2-(2H-tetrazol-5-yl)ethyl]benzaldehyde To 2-chlorotrityl resin (1.3 g, loading 1.26 mmol/g) pre-swelled in DCM for 1 hour was added a solution of 4-[1-hydroxy-2-(2H-tetrazol-5-yl)ethyl]benzaldehyde (1,4 g, 4.4 mmol) and DIPEA (0.931 ml, 5.4 mmol) in DMF (10 ml) and DCM (5 ml). The mixture was allowed to react at room temperature overnight under nitrogen. The resin was then drained and washed with DMF (3×30 ml) and DCM (5×30 ml) and dried in a vacuum oven overnight.

Step 3: Preparation of Resin Bound 1-{4-[(4-tert-Butylcyclohexylamino)methyl]phenyl}-2-(2H-tetrazol-5-yl)ethanol Resin bound 4-[1-hydroxy-2-(2H-tetrazol-5-yl)ethyl]benzaldehyde (50 mg) was swelled in DCM for 30 min. Solvent was removed, and the resin was washed once with DMF. A solution of 4-tert-butylcyclohexyl amine (25 mg, 0.164 mmol) in 50% TMOF in DMF (1 ml,) was added followed by acetic acid (50 μl). The mixture was shaken at room temperature for 3 hours, then a solution of sodium cyanoborohydride (13 mg, 0.20 mmol) in 50% MeOH in DMF (1 ml) was added. The resin-mixture was shaken overnight at room temperature, then drained and washed with DMF (3×2 ml) and DCP (3×2 ml).

Step 4: Preparation of 3-(3,5-bis(Trifluoromethyl)phenyl)-1-(4-tert-butylcyclohexyl)-1-{4-[1-hydroxy-2-(2H-tetrazol-5-yl)ethyl]benzyl}urea Resin bound 1-{4-[(4-tert-butylcyclohexylamino)methyl]phenyl}-2-(2H-tetrazol-5-yl)ethanol (50 mg) was suspended in DCP (500 μl) and N,O-bis(trimethylsilyl)acetamide (100 μl) was added. The mixture was shaken at room temperature for 1 hour, then a solution of 3,5-bis(trifluoromethyl) phenylisocyanate (48 mg, 0.19 mmol) in DCP (500 μl) was added. The resin mixture was shaken overnight at room temperature, then drained and washed with DCM (3×2 ml); DMF (3×2 ml); water (2×2 ml, each 20 min washes), THF (3×2 ml) and finally DCM (6×2 ml). The resin was then treated with 50% TFA in DCM for 30 min. Solvent was collected by filtration, and taken to dryness by evaporation in vacuo.

In a similar way the following compounds were prepared:

Example 19

(General Procedure (D))

3-[1-(4-Bromophenyl)ethyl]-1-(4-tert-butylcyclohexyl)-1-{4-[1-hydroxy-2-(2H-tetrazol-5-yl)ethyl]benzyl Urea

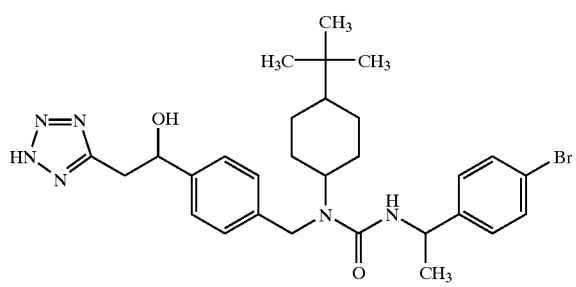

HPLC-MS (Method B): m/z=584 (M+1); $R_t$=5.70 min.

Example 20

(General Procedure (D))

3-(3-Methylthiophenyl)-1-(4-tert-butylcyclohexyl)-1-{4-[1-hydroxy-2-(2H-tetrazol-5-yl)-ethyl]benzyl Urea

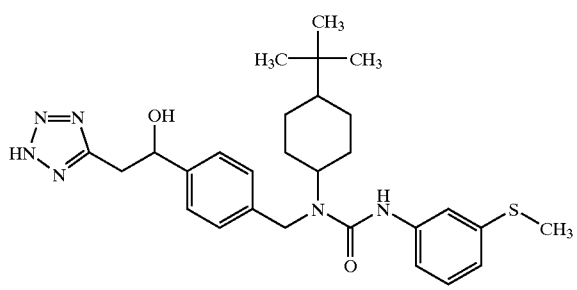

HPLC-MS (Method B): m/z=523 (M+1); $R_t$=5.62 min.

Example 21

(General Procedure (D))

3,4-Trifluoromethoxyphenyl)-1-(4-tert-butylcyclohexyl)-1-{4-[1-hydroxy-2-(2H-tetrazol-5-yl)ethyl]benzyl Urea

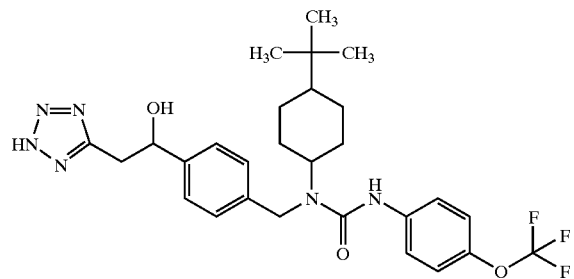

HPLC-MS (Method B): m/z=561 (M+1); $R_t$=5.62 min.

Example 22

(General Procedure (D))

3-(3,5-Dichlorophenyl)-1-(4-tert-Butylcyclohexyl)-1-{4-[1-hydroxy-2-(2H-tetrazol-5-yl)-ethyl]benzyl Urea

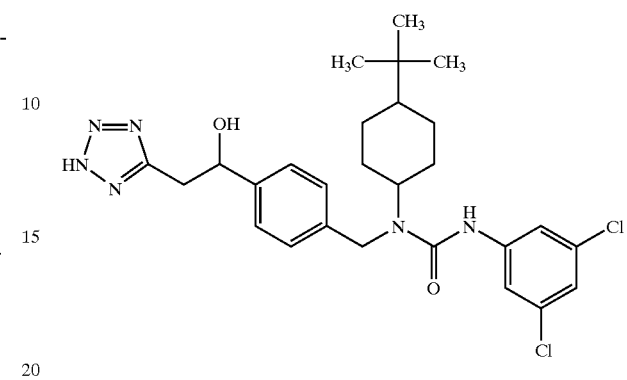

HPLC-MS (Method B): m/z=546 (M+1); $R_t$=6.30 min.

Example 23

(General Procedure (D))

3-(3-Fluoro-5-trifluoromethylphenyl)-1-(4-tert-butylcyclohexyl)-1-{4-[1-hydroxy-2(2H-tetrazol-5-yl)ethyl]benzyl Urea

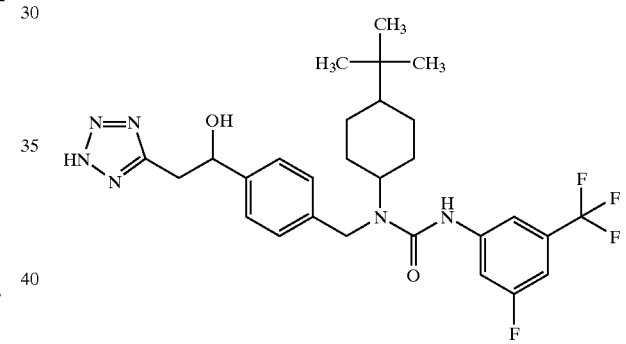

HPLC-MS (Method B): m/z=588 (M+1); $R_t$=6.22 min.

General Procedure (E)

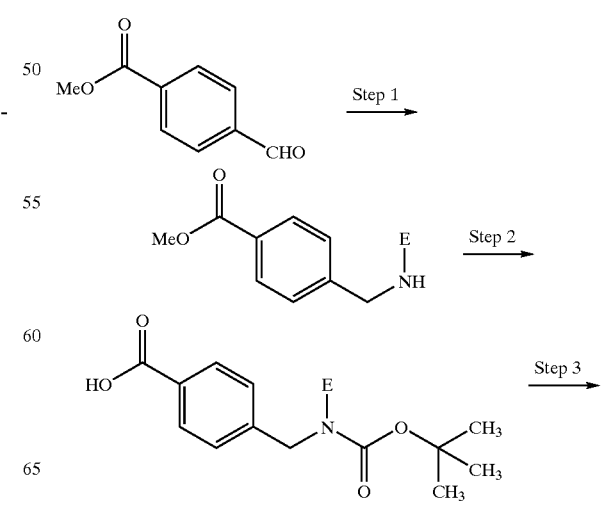

-continued

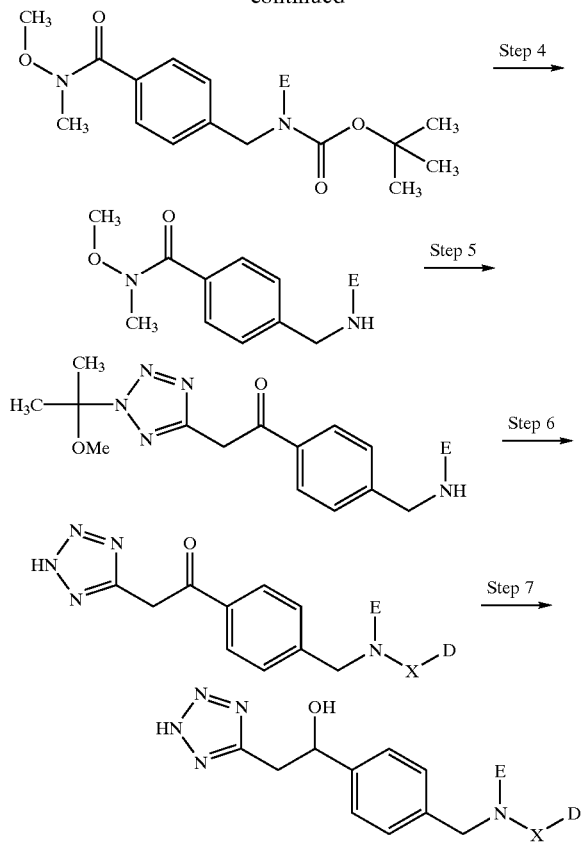

wherein X is —C(O)NH—, —C(O)NHCH₂—, —C(O)NHCH(CH₃)— or —C(O)NHCH₂CH₂— and D and E are as defined for formula (I).

Example 24

(General Procedure (E))
3-(3,5-Bis(trifluoromethyl)phenyl)-1-(4-tert-butylcyclohexyl)-1-{4-[1-hydroxy-2-(2H-tetrazol-5-yl)ethyl]benzyl}-urea (as Pure Enantiomer)

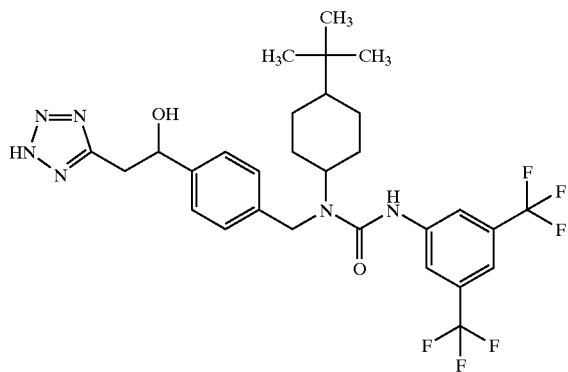

Step 1: trans-4-[(4-tert-Butylcyclohexylamino)methyl] benzoic Acid Methyl Ester

4-Formylbenzoic acid methyl ester (10.6 g, 64.4 mmol) was dissolved in methanol (200 ml). A 17:83 cis/trans mixture of 4-tert-butylcyclohexylamine (10.0 g, 64.4 mmol, Aldrich) was added, leading to immediate precipitation of white crystals. The mixture was heated to reflux for 30 min to complete imin formation, then cooled to 0° C. on an ice bath. The crystalline pure trans form was then collected by filtration, and dried overnight in vacuo. Yield: 15.3 g (78%).

¹H NMR (CDCl₃), 300 MHz: δ 8.37 ppm (s, 1H); 8.06 (d, 2H); 7.77 (d, 2H); 3.92 (s; 3H); 3.17 (m, 1H); 1.83 (m, 4H); 1.60 (m, 2H), 1.09 (m, 3H); 0.87 (s, 9H). Microanalysis: Calculated for C₁₉H₂₇NO₂ C: 75.71%, H: 9.03%, N: 4.65%. Found: C: 75.60%, H: 9.37%, N: 4.68%.

trans-4-[(4-tert-Butylcyclohexylimino)methyl]benzoic acid methyl ester (21.0 g, 69.2 mmol) was suspended in methanol (300 ml), and acetic acid (50 ml) was added. To the resulting clear solution was added sodium cyanoborohydride (3.5 g, 55.5 mmol), and the mixture was stirred at ambient temperature for 30 min. The reaction volume was then reduced to one-third by rotary evaporation, and ethyl acetate (500 ml) was added. The organic phase was washed with sodium carbonate solution (5%, 500 ml), and dried with sodium sulphate. The solvent was removed by rotary evaporation to leave the title material as a white crystalline solid sufficiently pure for further reactions. Yield: 21.1 g (100%).

¹H NMR (CDCl₃), 300 MHz: δ 7.98 ppm. (d, 2H); 7.38 (d, 2H); 3.90 (s, 3H); 3.86 (s, 2H); 2.39 (m, 1H); 2.01 (m, 2H); 1.77 (m, 2H); 1.51 (bs, 1H); 0.93–1.18 (m, 5H); 0.82 (s, 9H).

LC-MS (method) Calculated for C₁₉H₂₉NO₂: 303.4; Found 304.2 (M+H)⁺.

Step 2: trans-4-{[tert-Butoxycarbonyl-(4-tert-butylcyclohexyl)amino]methyl}benzoic Acid trans-4-[(4-tert-Butylcyclohexylamino)methyl]benzoic Acid Methyl Ester (20.0 g, 65.9 mmol) was dissolved in THF (300 ml). Di-tert-butylpyrocarbonate (16.0 g, 73.4 mmol) and diisopropylethylamine (12.0 g, 92.9 mmol) was added and the clear solution stirred overnight at ambient temperature. Solvent was removed by rotary evaporation and the crystalline residue re-dissolved in ethanol (200 ml). Aqueous sodium hydroxide solution (100 ml, 4 N) was added and the mixture was heated to 70° C. for 4 hours. After cooling, the reaction volume was reduced to one third by rotary evaporation, and water (300 ml) was added. The mixture was extracted with diethyl ether (2×200 ml) to remove traces of non hydrolysed material. The water phase was then acidified to pH 3.0 by addition of aqueous 4 N HCl, whereupon the title material separated out of solution as compact crystals. The crystals were washed once with water and dried overnight in a vacuum oven (40° C.). Yield: 24.3 g (93%). ¹H NMR (CDCl₃), 300 MHz: δ 8.04 ppm. (d, 2H); 7.31 (d, 2H); 4.39 (bs, 2H); 4.05 (bs, 1H); 1.78 (bd, 4H); 0.95–1.65 (m, 14H); 0.83 (s, 9H). The signals were broaden due to the presence of cis/trans carbamate isomers.

Microanalysis: Calculated for C₂₃H₃₅NO₄: C: 70.92%, H: 9.06%, N: 3.60%. Found: C: 70.67%, H: 9.36%, N: 3.57%.

Step 3: N-Methoxy-N-methyl-trans-4-{[tert-Butoxycarbonyl-(4-tert-butylcyclohexyl)-amino]methyl}benzamide trans-4-[tert-Butoxycarbonyl-(4-tert-butylcyclohexyl) amino]methyl}benzoic acid (5.0 g, 12.8 mmol) was dissolved in 50% DMF in DCM (50 ml). 1-Hydroxybenzotriazole (1.0 g, 14.1 mmol) was added followed by N-ethyl-N'-dimethylaminopropylcarbodiimide hydrochloride (2.7 g, 14.1 mmol). The mixture was stirred at room temperature for 1 hour, before adding N,O-dimethylhydroxylamine hydrochloride (1.4 g, 14.1 mmol) and DIPEA (2.4 ml, 14.1 mmol). The reaction mixture was stirred at room temperature overnight, then partitioned between ethyl acetate (300 ml) and saturated aqueous sodium hydrogen carbonate (200 ml). The organic phase was collected, dried with anhydrous sodium sulphate and taken to dryness by rotary evaporation, to leave the title material as a clear yellow oil. Yield: 4.8 g (87%).

¹H NMR (CDCl₃), δ 7.60 (d, 2H); 7.25 (d, 2H); 4.38 (bs, 2H); 4.02 (bs, 1H); 3.55 (s, 3H); 3.35 (s, 3H); 1.78 (bd, 4H); 0.95–1.65 (m, 14 H); 0.81 (s, 9H).

Step 4: N-Methoxy-N-methyl-trans-4-{[4-tert-butylcyclohexylamino]methyl}benzamide N-Methoxy-N-methyl-trans-4-{[tert-butoxycarbonyl-(4-tert-butylcyclohexyl)amino]methyl}benzamide (1.0 g, 2.3 mmol) was dissolved in DCM (10 ml), and TFA (10 ml) was added. The reaction mixture was stirred at ambient temperature for 2 hours and then taken to dryness by rotary evaporation. The crystal-line residue was then dissolved in ethyl acetate (100 ml), and the organic phase was washed with saturated aqueous sodium carbonate solution (2×100 ml). The combined water phases were back extracted once with ethyl acetate (100 ml); and the combined organic phases dried with anhydrous sodium sulphate. Solvent was removed by rotary evaporation, to leave the title product as fine white crystals. Yield: 760 mg (99%).

¹H NMR (CDCl₃) δ 7.62 (d, 2H); 7.34 (d, 2H); 3.83 (s, 2H); 3.53 (s, 3H); 3.33 (s, 3H); 2.40 (m, 1H); 2.01 (m, 2H); 1.78 (m, 2H); 1.20–0.95 (m, 4H), 0.84 (s, 9H).

Microanalysis: Calculated for C₂₀H₃₂N₂O₂: C: 72.25%, H: 9.70%, N: 8.43%. Found: C: 71.22%, H: 9.79%, N: 8.29%.

Step 5: 1-{4-[(4-tert-Butylcyclohexylamino)methyl]phenyl}-2-[2-(1-methoxy-1-methyl-ethyl)-2H-tetrazol-5-yl]ethanone To a solution of 2-(1-methoxy-1-methylethyl)-5-methyl-2H-tetrazole (893 mg, 5.7 mmol) in THF (10 ml) cooled to −78° C. on a dry-ice-acetone bath was added dropwise a solution of n-butyl lithium in hexanes (3.6 ml, 1.6 M, 5.7 mmol). The mixture was stirred at −78° C. for 30 min, and at 0° C. for an additional 30 min, then recooled to −78° C. This solution was then slowly transferred (by cannulation) to a solution of N-methoxy-N-methyl-trans-4-{[4-tert-butylcyclohexylamino]methyl}benzamide (760 mg, 2.3 mmol) in THF (15 ml) maintained at −78° C. The reaction mixture was stirred for 30 min at −78° C. and then quenched by the addition of methanol (2 ml). Solvent was removed by rotary evaporation, and the residue was dissolved in ethyl acetate (100 ml). The organic phase was washed once with saturated aqueous sodium hydrogen carbonate (100 ml); dried over anhydrous sodium sulphate and taken to dryness by rotary evaporation to leave 1.0 g (100%) of the title material as an clear oil.

¹H NMR (CDCl₃), δ 7.96 (d, 2H); 7.42 (d, 2H); 4.62 (s, 2H); 3.88 (s, 2H); 3.10 (s, 3H); 2.38 (m, 1H); 1.99 (s, 6H); 1.85 (m, 2H); 1.78 (m, 2H); 1.20–0.95 (m, 4H), 0.84 (s, 9H). HPLC-MS (Method B): m/z=356.2 (M+1); R$_t$=2.57 min.

Step 6: 3-(3,5-bis(Trifluoromethyl)phenyl)-1-(4-tert-butylcyclohexyl)-1-[4-(2-2H-tetrazol-5-yl-acetyl)benzyl]urea 1-{4-[(4-tert-Butylcyclohexylamino)methyl]phenyl}-2-[2-(1-methoxy-1-methylethyl)-2H-tetrazol-5-yl]ethanone (320 mg, 0.75 mmol) was dissolved in THF (5 ml), and 3,5-bis(trifluoromethyl)phenyl isocyanate (191 mg, 0.75 mmol) was added. The reaction mixture was stirred at room temperature for 2 hours and then taken to dryness by rotary evaporation. The residue was stripped twice from acetonitrile to give 450 mg (88%) of title material.

¹H NMR (DMSO-d₆): δ 9.05 (s, 1H); 8.22 (s, 2H); 8.02 (d, 2H); 7.60 (s, 1H); 7.45 (d, 2H); 4.89 (s, 2H); 4.68 (s, 2H); 4.08 (m, 1H); 1.72 (m, 4H); 1.45 (m, 2H); 1.15 (m, 2H); 8.82 (s, 9H). HPLC-MS (Method B): m/z=611.2 (M+1); R$_t$=5.94 min.

Step 7:

To a solution of (R)-tetrahydro-1-methyl-3,3-diphenyl-1H,3H-pyrrolo[1,2-c]-[1,3,2]oxazaborole in toluene (17 μl, 0.17 mmol, 1 M) in THF (1 ml) was added boran-THF complex (328 μl, 0.32 mmol, 1 M in THF). Then a solution of 3-(3,5-bis(trifluoromethyl)phenyl)-1-(4-tert-butylcyclohexyl)-1-[4-(2-2H-tetrazol-5-yl-acetyl)-benzyl]urea (100 mg, 0.17 mmol) in THF (1.0 ml) was added dropwise over a period of 30 min. The reaction mixture was stirred at room temperature overnight and then quenched with 1 N aqueous HCl (100 μl). Solvent was removed by rotary evaporation. The residue was dissolved in THF (500 μl) and injected into a preparative HPLC on a Gilson 2.11 with auto sampler (Xterra MS C₁₈ 5 μm 19 mm×100 mm, gradient: 10% acetonitrile in water→100% acetonitrile).

¹H NMR (DMSO-d₆): δ 9.02 (s, 1H); 8.25 (s, 2H); 7.58 (s, 1H); 7.26 (d, 2H); 7.20 (d, 2H); 4.92 (m, 1H); 4.55 (s, 2H); 4.05 (m, 1H); 3.15 (ddd, 2H); 1.63 (m, 4H); 1.42 (m, 2H); 1.10 (m, 2H); 0.92 (m, 1H); 0.80 (s, 9H).

Example 25

General Procedure (E)

3-(3,5-bis(Trifluoromethyl)phenyl)-1-(4-tert-butylcyclohexyl)-1-{4-[1-hydroxy-2-(2H-tetrazol-5-yl)ethyl]benzyl}urea (as the Other Pure Enantiomer)

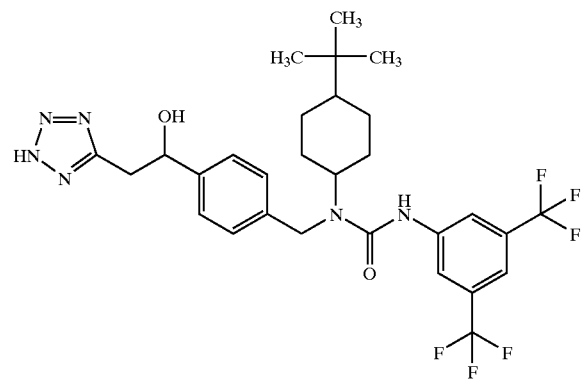

To a solution of (S)-tetrahydro-1-methyl-3,3-diphenyl-1H,3H-pyrrolo[1,2-c]-[1,3,2]oxazaborole in toluene (17 μl, 0.17 mmol, 1 M) in THF (1 ml) was added boran-THF complex (328 μl, 0.32 mmol, 1 M in THF). Then a solution of 3-(3,5-bis(trifluoromethyl)phenyl)-1-(4-tert-butyl-cyclohexyl)-1-[4-(2-2H-tetrazol-5-yl-acetyl)-benzyl]urea (100 mg, 0.17 mmol) in THF (1.0 ml) was added dropwise over a period of 30 min. The reaction mixture was stirred at room temperature overnight and then quenched with 1 N aqueous HCl (100 μl). Solvent was removed by rotary evaporation. The residue was dissolved in THF (500 μl) and injected into a preparative HPLC on a Gilson 2.11 with auto sampler (Xterra MS C₁₈ 5 μm 19 mm×100 mm, gradient: 10% acetonitrile in water→100% acetonitrile).

¹H NMR (DMSO-d₆): δ 9.02 (s, 1H); 8.25 (s, 2H); 7.58 (s, 1H); 7.26 (d, 2H); 7.20 (d, 2H); 4.92 (m, 1H); 4.55 (s, 2H); 4.05 (m, 1H); 3.15 (ddd, 2H); 1.63 (m, 4H); 1.42 (m, 2H); 1.10 (m, 2H); 0.92 (m, 1H); 0.80 (s, 9H).

Example 26
1-(4-Cyclohex-1-enylphenyl)-3-(3,5-dichlorophenyl)-1-{4-[1-hydroxy-2-(2H-tetrazol-5-yl)ethyl]benzyl}urea

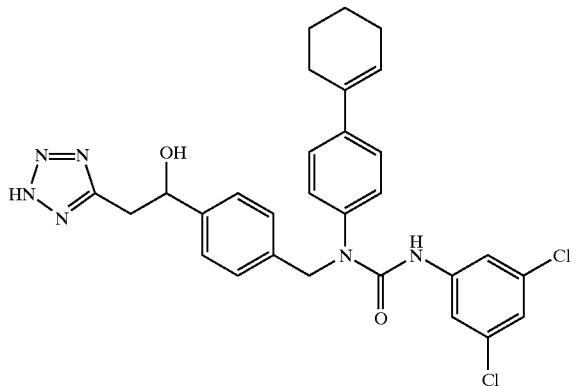

To a solution of 2-(1-methoxy-1-methylethyl)-5-methyl-2H-tetrazole (1000 mg, 6.41 mmol) in THF (5 ml) cooled to −78° C. on a dry-ice-acetone bath was added dropwise a solution of n-butyl lithium in hexanes (4.0 ml, 1.6 M, 6.4 mmol). The mixture was stirred at −78° C. for 30 min, and at 0° C. for an additional 30 min, then recooled to −78° C. 1-(4-Cyclohex-1-enylphenyl)-3-(3,5-dichlorophenyl)-1-(4-formylbenzyl)urea (250 mg, 0.52 mmol, from step 2, example 12) was then added as a solid, and the mixture was maintained at −78° C. for 20 min. Reaction temperature was raised to 0° C. and the mixture was stirred for 20 min before addition of acetic acid (2 ml). Upon standing, a white solid starts to precipitate, which is collected and washed with cold acetonitrile. The solid is oven dried under vacuum, to yield 582 mg (95%).

$^1$H NMR (DMSO-d$_6$): δ 8.50 (s, 1H); 7.59 (s, 2H); 7.38 (d, 2H); 7.25 (d, 2H); 7.20 (d, 2H); 7.12 (d, 2H); 7.09 (s, 1H); 6.18 (s, 1H); 4.92 (m, 1H); 4.86 (s, 2H); 3.14 (ddd, 2H); 2.32 (m, 2H); 2.15 (m, 2H); 1.70 (m, 2H); 1.52 (m, 2H). HPLC-MS (Method B): m/z=564.1 (M+1); R$_t$=5.35 min

Example 27
Methanesulphonic Acid 1-{4-[1-(4-cyclohex-1-enylphenyl)-3-(3,5-dichlorophenyl)-ureidomethyl]phenyl}-2-(2H-tetrazol-5-yl)ethyl Ester

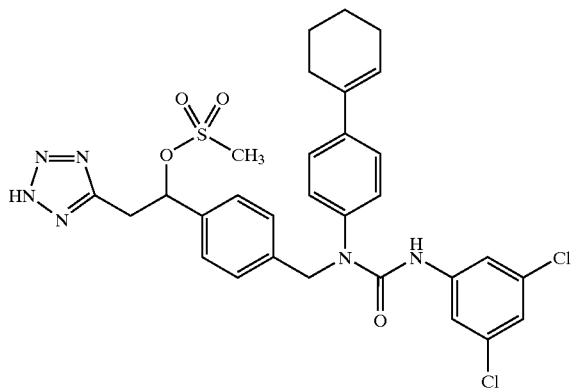

1-(4-Cyclohex-1-enylphenyl)-3-(3,5-dichlorophenyl)-1-{4-[1-hydroxy-2-(2H-tetrazol-5-yl)ethyl]benzyl}urea (100 mg, 0.17 mmol) was dissolved in DCM (1 ml) and triethyl amine (27 μl, 0.195 mmol) was added. The mixture was cooled to 0° C. and methansulphonyl chloride (15 μl, 0.195 mmol) was added followed by 1,8-diazabicyclo[5,4,0]-undec-7-ene (29 μl, 0.195 mmol). The mixture was stirred at 0° C. for 2 hours, and at room temperature overnight, then diluted with DCM (20 ml) and washed with brine (20 ml). The organic solution was dried with anhydrous sodium sulphate and evaporated to dryness, to give pure title material as a white powder. Yield: 113 mg (100%).

$^1$H NMR (DMSO-d$_6$): δ 8.54 (s, 1H); 7.60 (s, 2H); 7.40 (d, 2H); 7.30 (d, 2H); 7.25 (d, 2H); 7.18 (d, 2H); 7.14 (s, 1H); 6.20 (s, 1H); 6.05 (m, 1H); 4.88 (s, 2H); 3.45 (ddd, 2H); 2.34 (bs, 2H); 2.18 (bs, 2H); 2.10 (s, 3H); 1.70 (m, 2H); 1.60 (m, 2H).

Example 28
Acetic Acid 1-{4-[1-(4-cyclohex-1-enylphenyl)-3-(3,5-dichlorophenyl)ureidomethyl]-phenyl}-2-(2H-tetrazol-5-yl)ethyl Ester

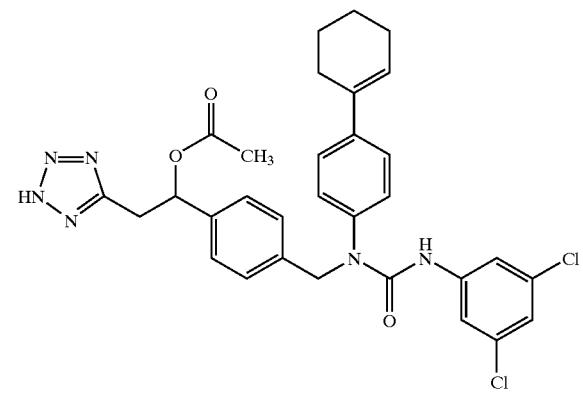

1-(4-Cyclohex-1-enylphenyl)-3-(3,5-dichlorophenyl)-1-{4-[1-hydroxy-2-(2H-tetrazol-5-yl)ethyl]benzyl}urea (30 mg, 0.05 mmol) was dissolved in DCM (1.5 ml) and acetic acid anhydride (15 μl) was added. The mixture was stirred at room temperature overnight, and then taken to dryness. The residual oil was dissolved in ethanol (2 ml), and heated to reflux for 0.5 min. Then cooled and evaporated to dryness. The residue was stripped twice from acetonitrile to give a quantitative yield of the title compound.

$^1$H NMR (DMSO-d$_6$): δ 8.52 (s, 1H); 7.60 (d, 2H); 7.90 (d, 2H); 7.30 (d, 2H); 7.22 (d, 2H); 7.15 (d, 2H); 7.10 (s, 1H); 6.18 (s, 1H); 6.05 (dd, 1H); 4.85 (s, 2H); 3.38 (ddd, 2H); 2.32 (m, 2H); 2.15 (m, 2H); 1.98 (s, 3H); 1.68 (m, 2H); 1.57 (m, 2H).

The following compounds are also within the scope of the present invention and may be prepared in analogy to example 12:

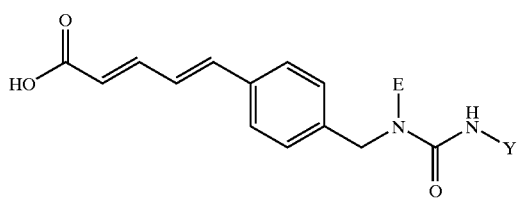
wherein
| E | Y |
|---|---|
| 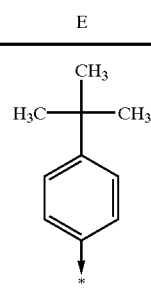 | 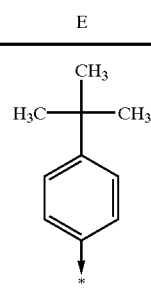 |
| 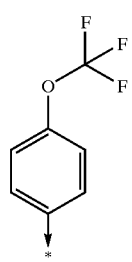 | 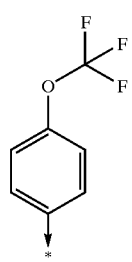 |
| 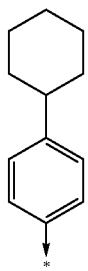 | 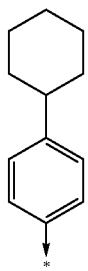 |
| 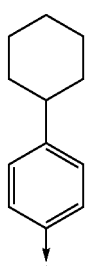 | 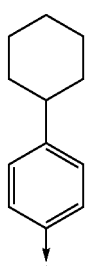 |
| 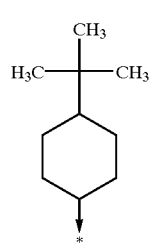 | 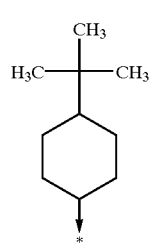 |
-continued
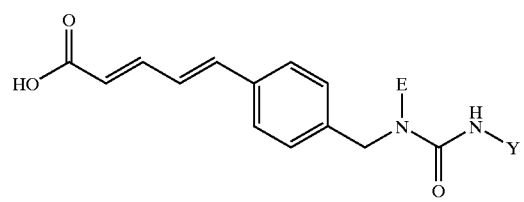
wherein
| E | Y |
|---|---|
| 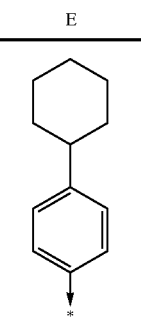 | 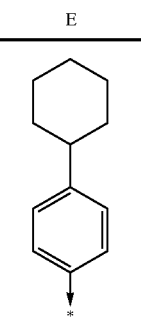 |
| 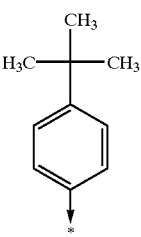 | 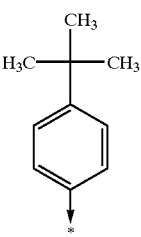 |
| 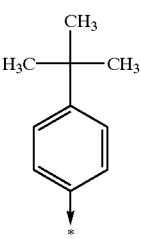 | 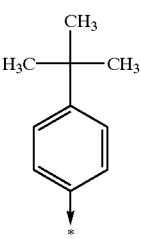 |
| 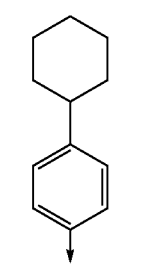 | 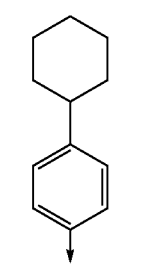 |
| 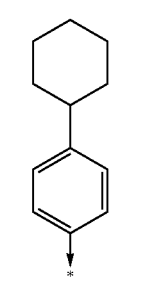 | 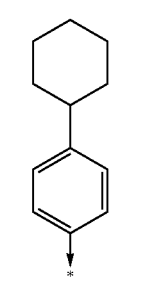 |

-continued
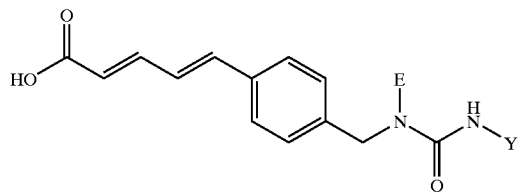
wherein
| E | Y |
|---|---|
| 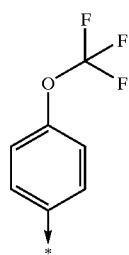 | 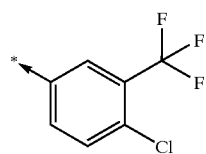 |
| 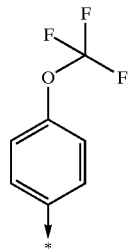 | 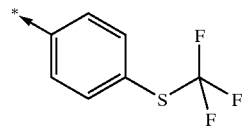 |
| 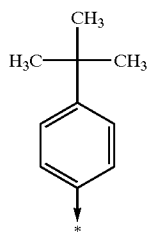 | 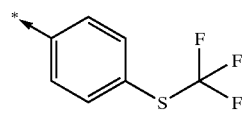 |
| 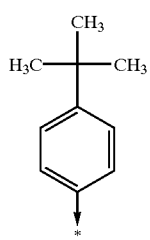 | 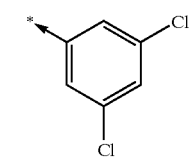 |
| 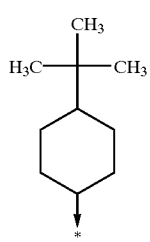 | 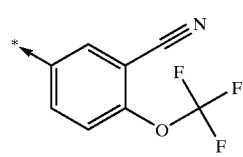 |
-continued
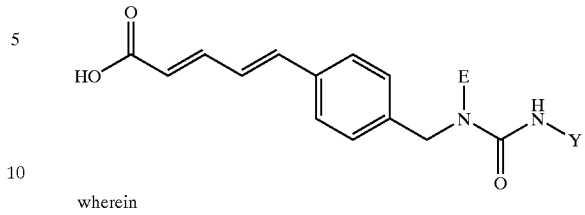
wherein
| E | Y |
|---|---|
| 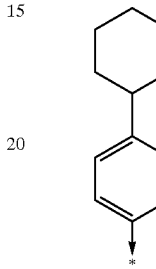 | 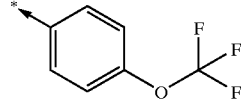 |
| 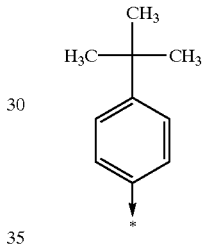 | 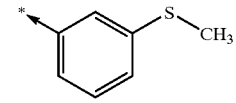 |
| 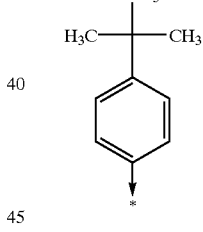 | 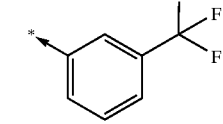 |
| 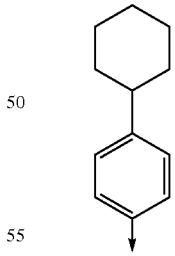 | 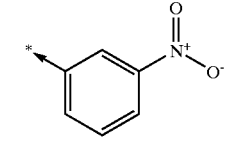 |
| 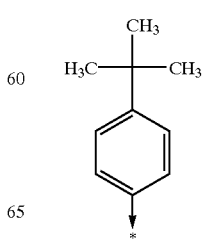 | 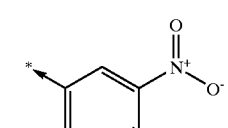 |

-continued
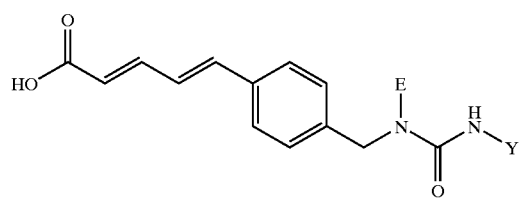
wherein
| E | Y |
|---|---|
| 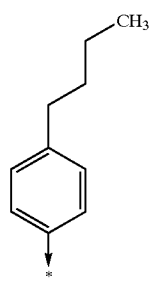 | 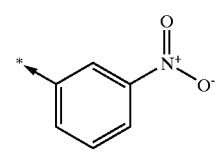 |
| 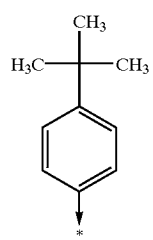 | 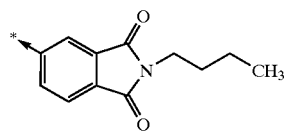 |
| 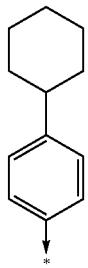 | 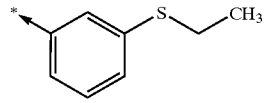 |
| 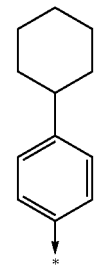 | 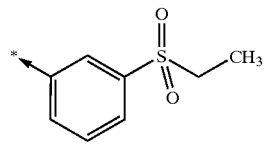 |
| 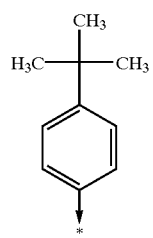 | 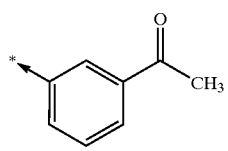 |
-continued
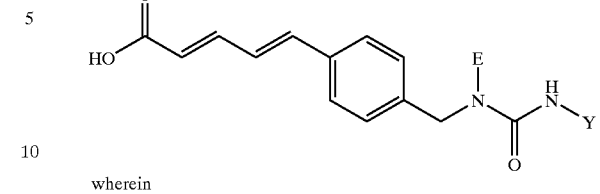
wherein
| E | Y |
|---|---|
| 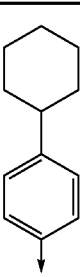 | 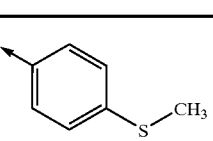 |
| 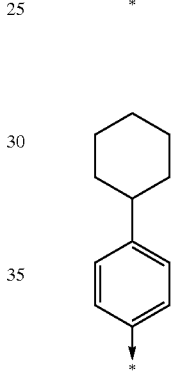 | 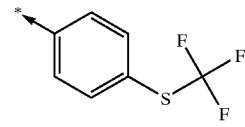 |
| 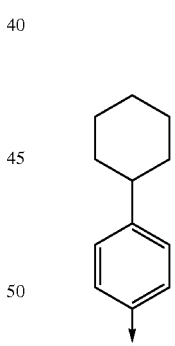 | 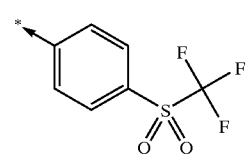 |
| 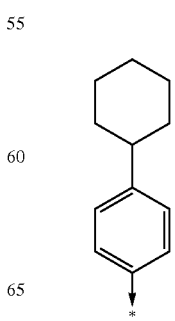 | 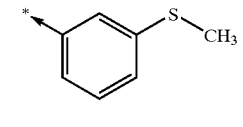 |

-continued
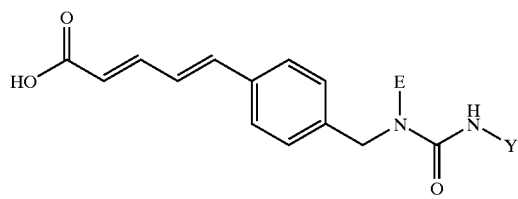
wherein
| E | Y |
|---|---|
| 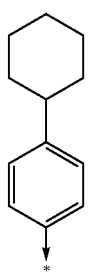 | 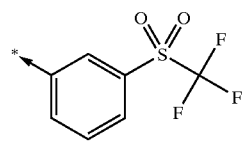 |
| 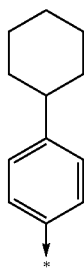 | 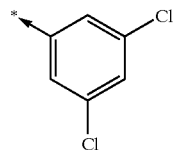 |
| 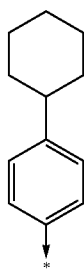 | 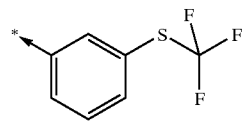 |
| 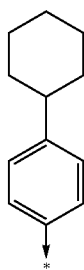 | 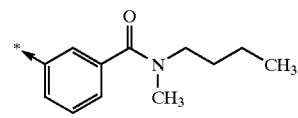 |
-continued
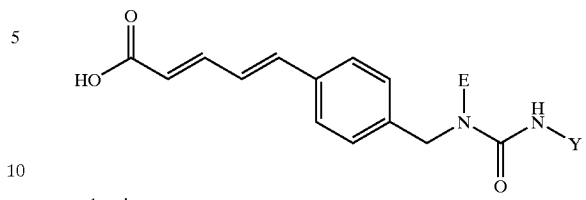
wherein
| E | Y |
|---|---|
| 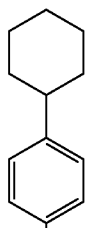 | 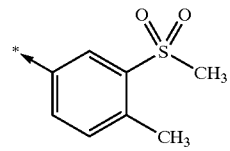 |
| 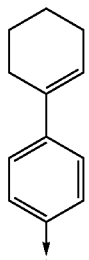 | 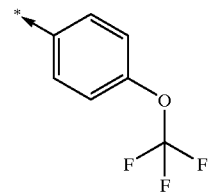 |
| 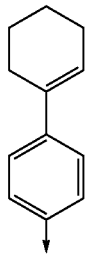 | 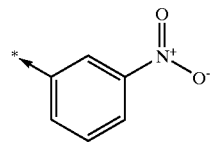 |
| 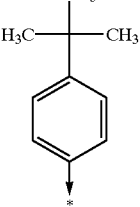 | 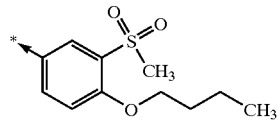 |

-continued
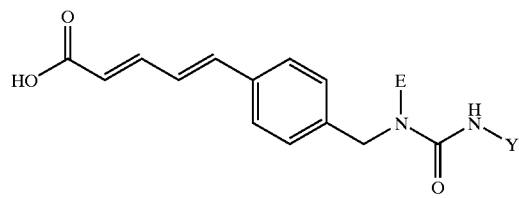
wherein
| E | Y |
|---|---|
| 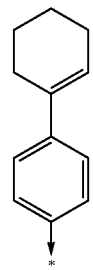 | 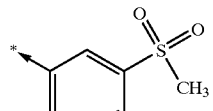 |
| 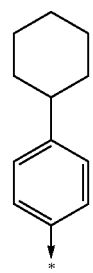 | 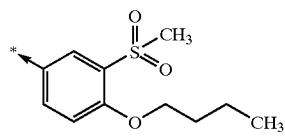 |
| 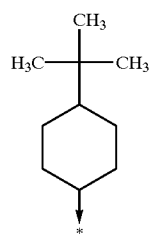 | 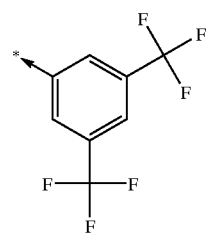 |
| 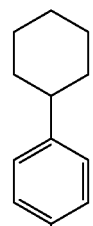 | 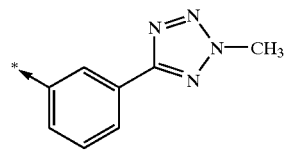 |
| 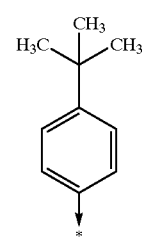 | 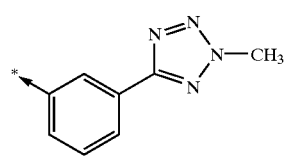 |
-continued
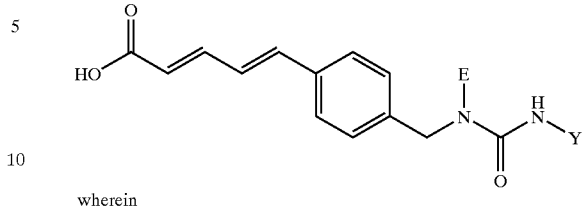
wherein
| E | Y |
|---|---|
| 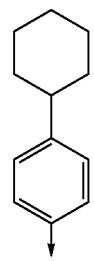 | 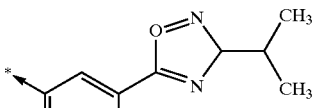 |
| 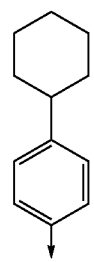 | 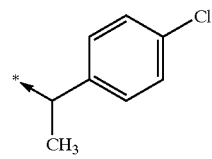 |
| 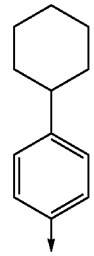 | 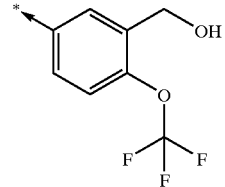 |
| 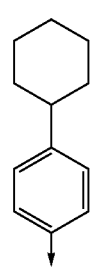 | 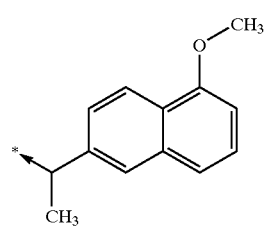 |

-continued wherein

| E | Y |
|---|---|
| cyclohexyl-phenyl- | 4-chlorophenyl-CH(CH₃)- |
| cyclohexyl-phenyl- | 3-trifluoromethyl-5-fluorophenyl- |
| tert-butyl-phenyl- | 3-methylsulfonyl-4-trifluoromethoxyphenyl- |
| tert-butyl-cyclohexyl- | 3-methylsulfonyl-4-trifluoromethoxyphenyl- |
| cyclohexyl-phenyl- | 3-methylsulfonyl-4-trifluoromethoxyphenyl- |

-continued wherein

| E | Y |
|---|---|
| cyclohexenyl-phenyl- | 3-methylsulfonyl-4-trifluoromethoxyphenyl- |
| cyclohexyl-phenyl- | ethyl benzothiazole-6-carboxylate-2-yl- |
| tert-butyl-phenyl- | 3-trifluoromethyl-5-bromophenyl- |
| cyclohexyl-phenyl- | 3-trifluoromethyl-5-bromophenyl- |

-continued
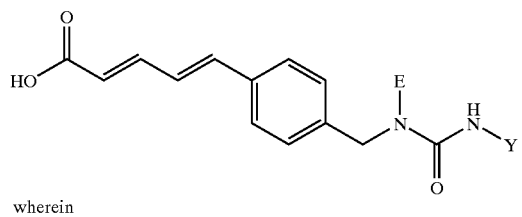
wherein
| E | Y |
|---|---|
| 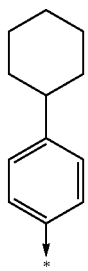 | 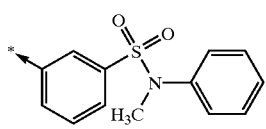 |
| 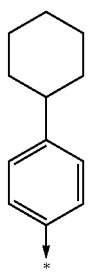 | 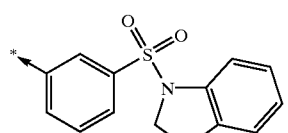 |
| 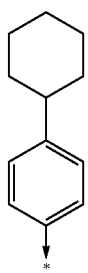 | 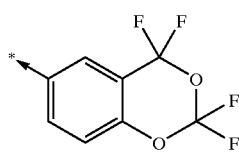 |
| 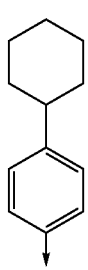 | 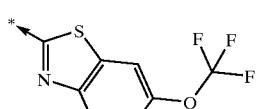 |
-continued
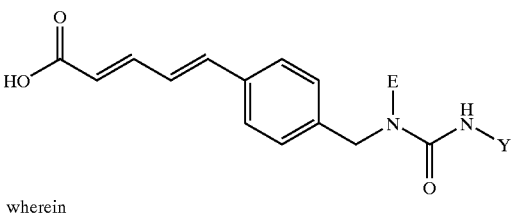
wherein
| E | Y |
|---|---|
| 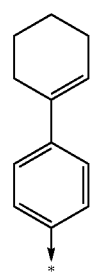 | 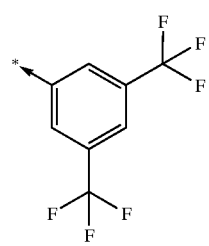 |
| 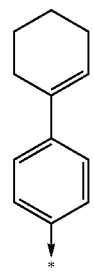 | 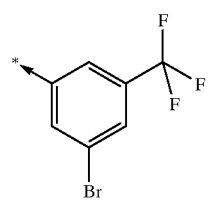 |
| 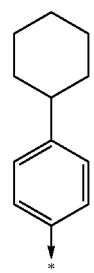 | 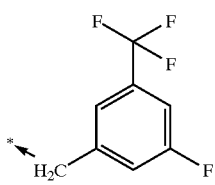 |
| 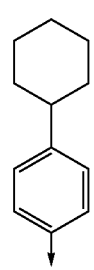 | 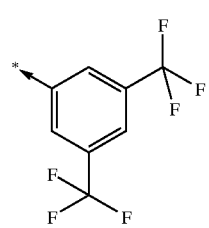 |

-continued
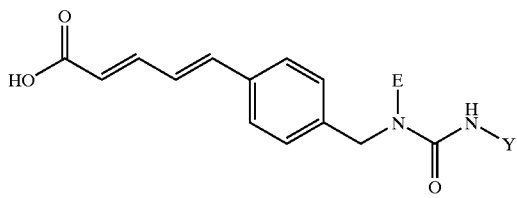
wherein
| E | Y |
|---|---|
| 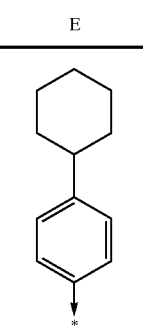 | 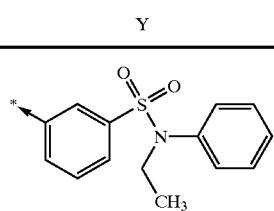 |
| 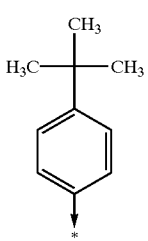 | 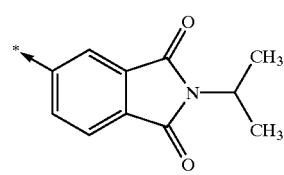 |
| 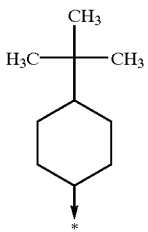 | 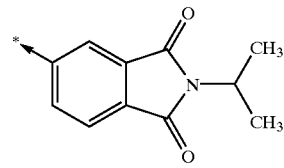 |
| 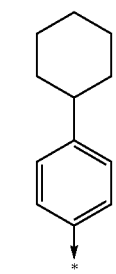 | 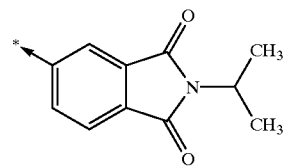 |
| 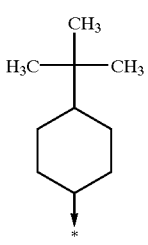 | 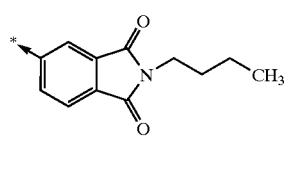 |
-continued
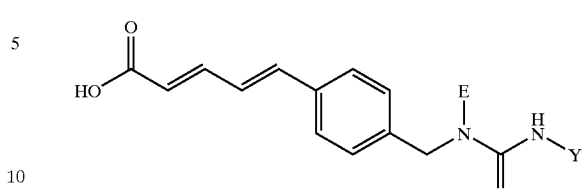
wherein
| E | Y |
|---|---|
| 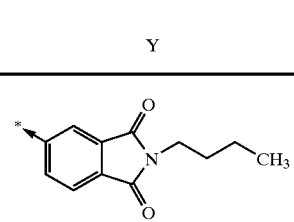 | 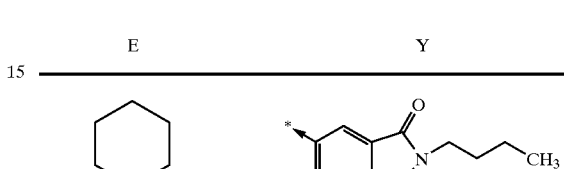 |
|  | |
|  | |
|  | |
|  | |
|  | |
|  | |
|  | |
|  | |

-continued
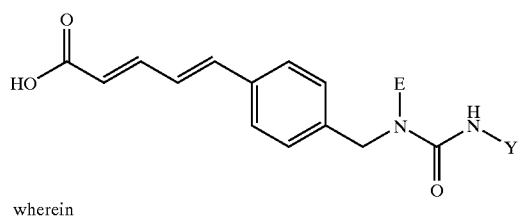
wherein
| E | Y |
|---|---|
| 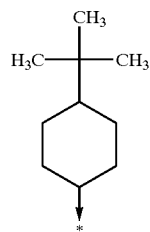 | 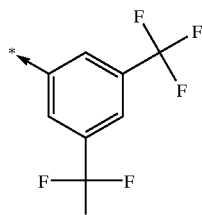 |
| 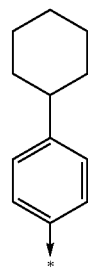 | 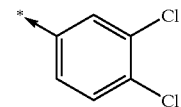 |
| 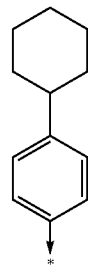 | 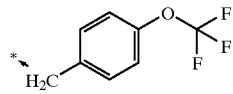 |
| 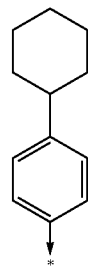 | 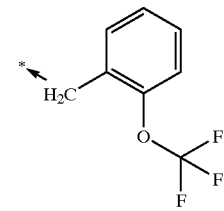 |
| 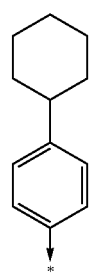 | 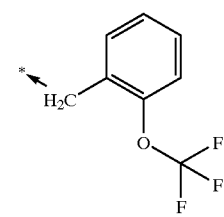 |
-continued
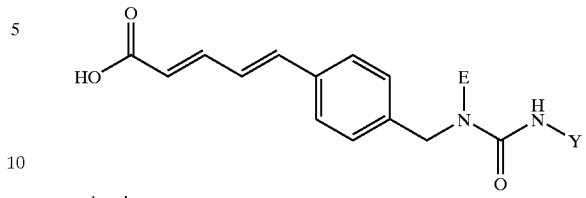
wherein
| E | Y |
|---|---|
| 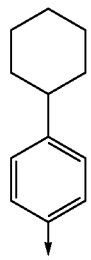 | 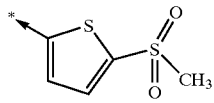 |
|  | |
|  | 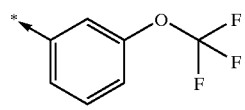 |
|  |  |
|  | 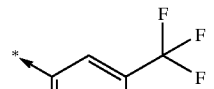 |
|  | 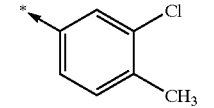 |
|  | |

-continued
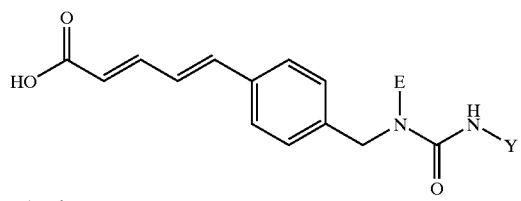
wherein
| E | Y |
|---|---|
| 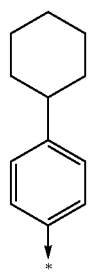 | 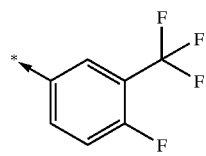 |
| 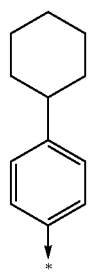 | 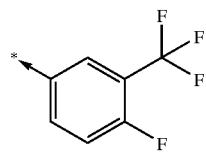 |
| 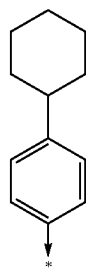 | 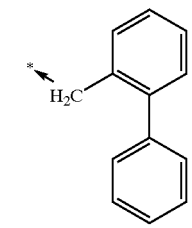 |
| 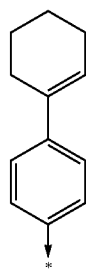 | 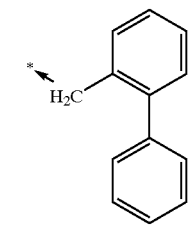 |
-continued
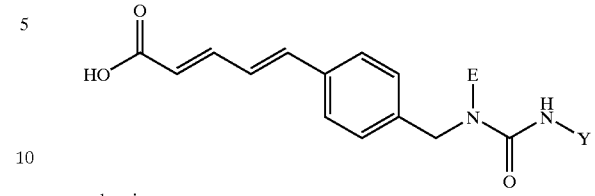
wherein
| E | Y |
|---|---|
| 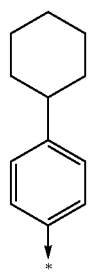 | 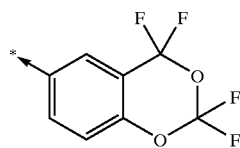 |
| 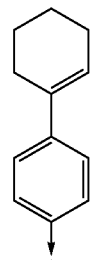 | 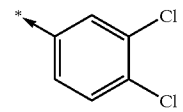 |
| 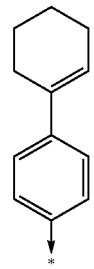 |  |
| 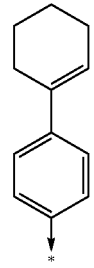 | 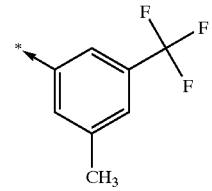 |

-continued
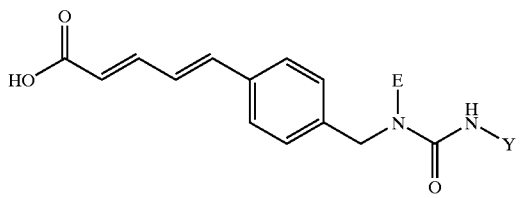
wherein
| E | Y |
|---|---|
| 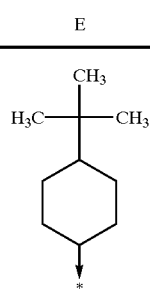 | 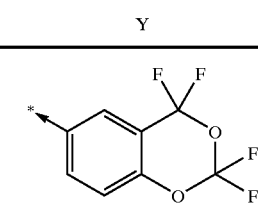 |
| 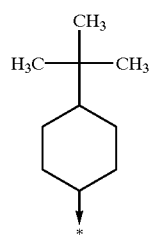 | 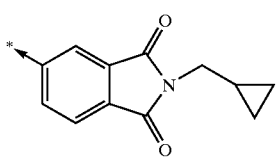 |
| 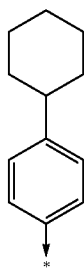 | 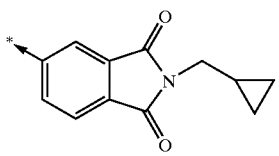 |
| 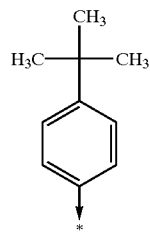 | 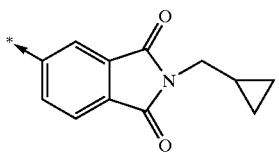 |
| 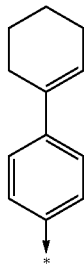 | 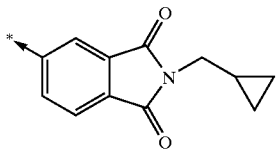 |
-continued
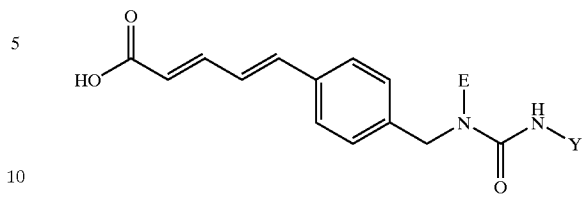
wherein
| E | Y |
|---|---|
| 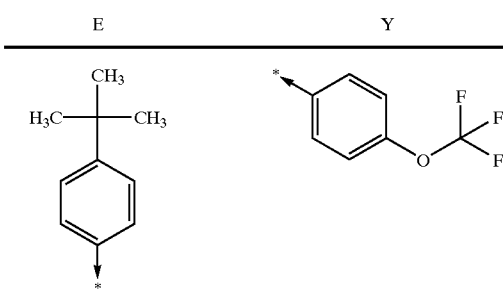 | 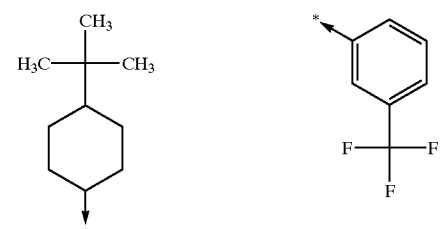 |
| 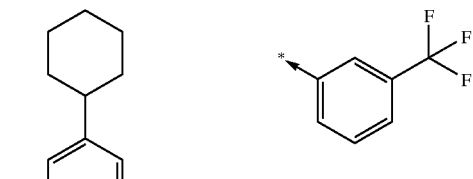 | 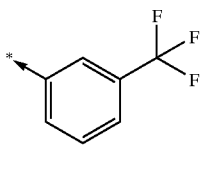 |
| 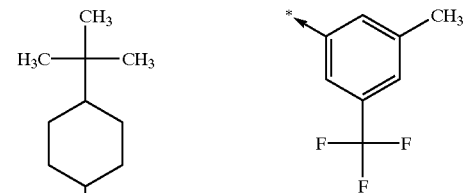 | 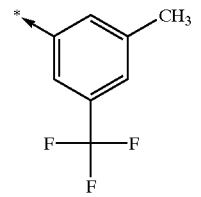 |
| 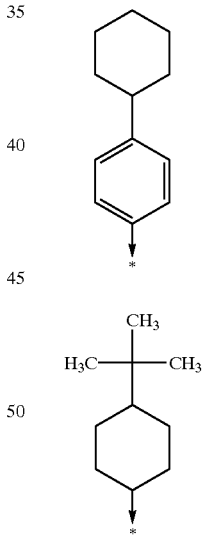 | 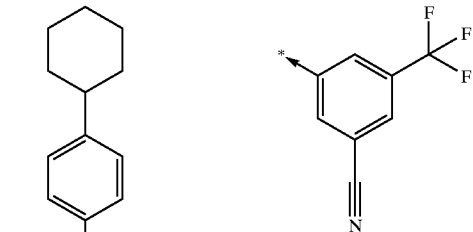 |
| 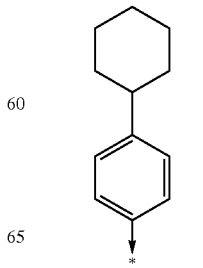 | 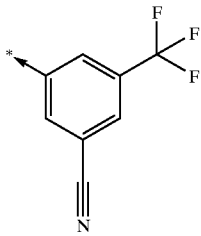 |

| 75 | 76 |
|---|---|
| -continued | -continued |
| 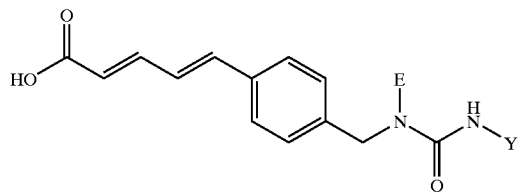 | 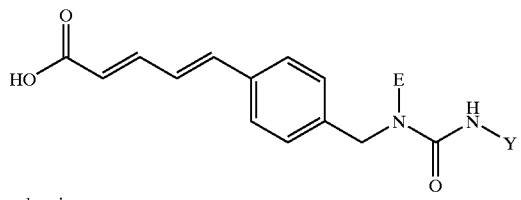 |
| wherein | wherein |
| E | Y | E | Y |
|---|---|---|---|
| 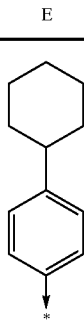 | 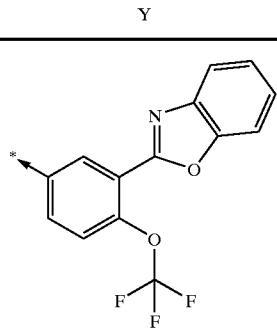 | 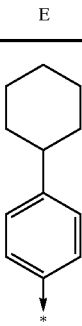 | 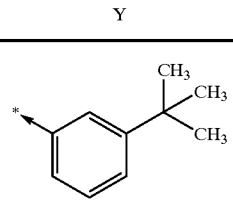 |
| 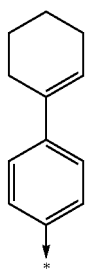 | 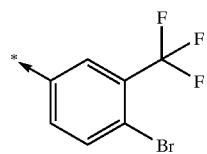 | 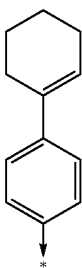 | 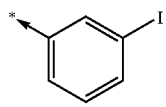 |
| 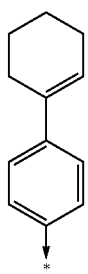 | 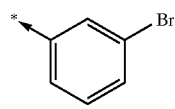 | 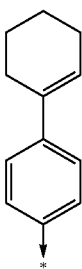 | 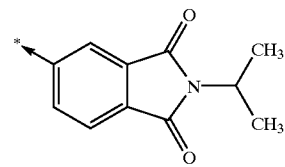 |
| 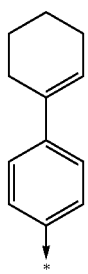 | 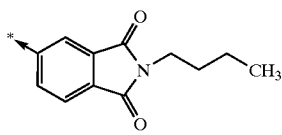 | 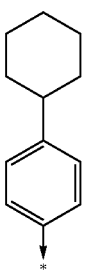 | 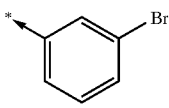 |

-continued
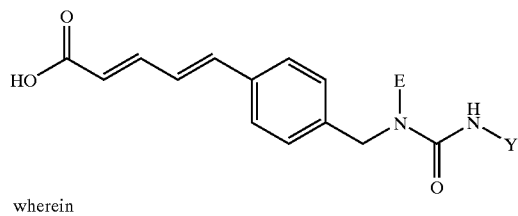
wherein
| E | Y |
|---|---|
| 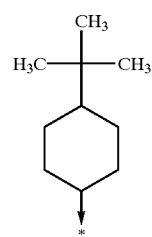 | 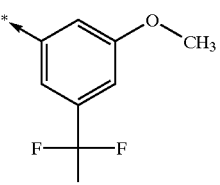 |
| 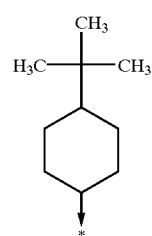 | 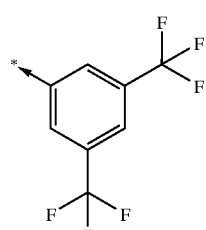 |
| 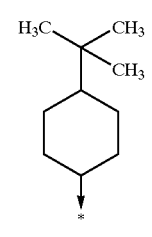 | 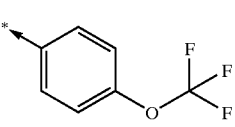 |
| 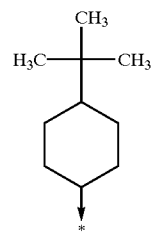 | 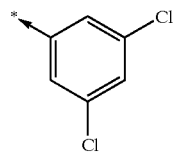 |
| 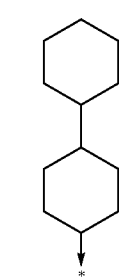 | 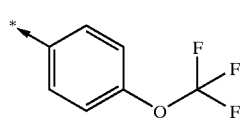 |
-continued
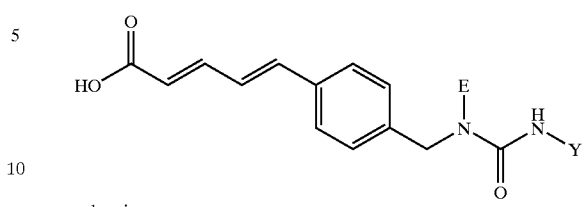
wherein
| E | Y |
|---|---|
| 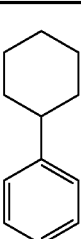 | 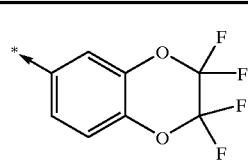 |
| 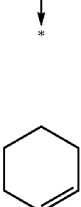 | 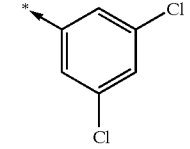 |
| 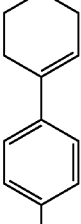 |  |
| 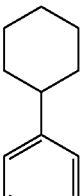 | 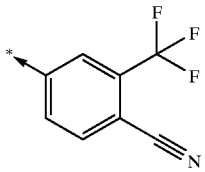 |
| 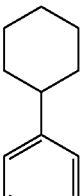 |  |

-continued
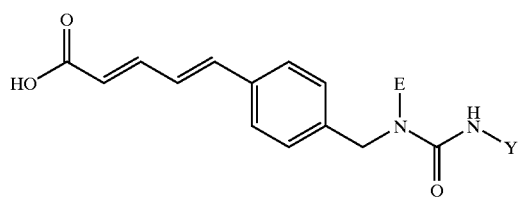
wherein
| E | Y |
|---|---|
| 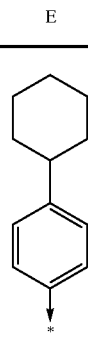 | 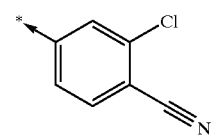 |
| 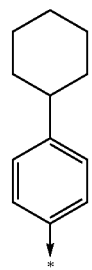 | 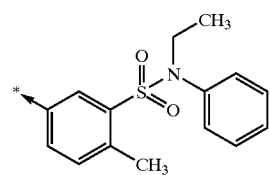 |
| 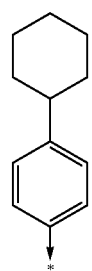 | 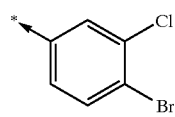 |
| 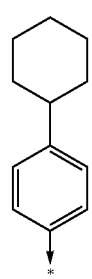 | 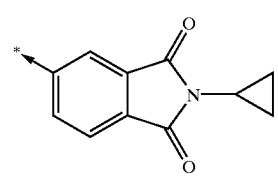 |
-continued
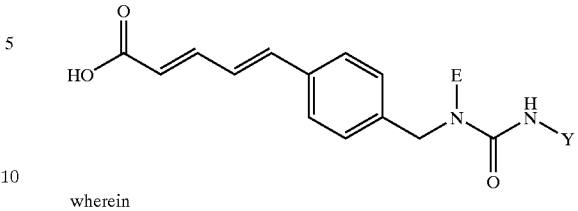
wherein
| E | Y |
|---|---|
| 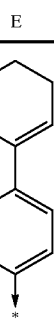 | 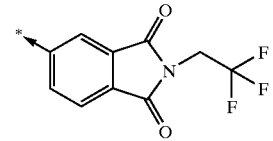 |
| 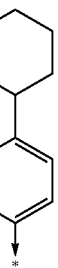 | 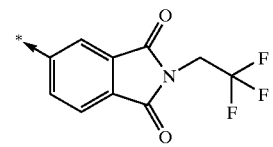 |
| 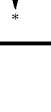 | 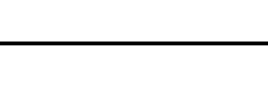 |
The following compounds are also within the scope of the present invention and may be prepared in analogy to examples 1 and 12:
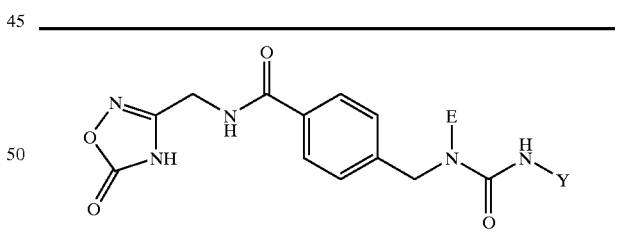
wherein
| E | Y |
|---|---|
| 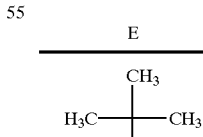 | 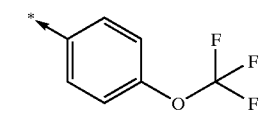 |
| 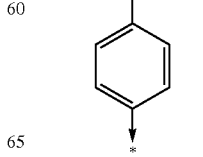 |  |

81
-continued
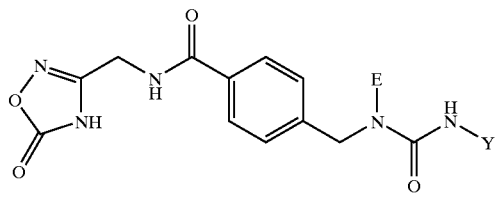
wherein
| E | Y |
|---|---|
| 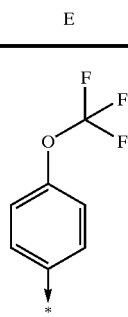 | 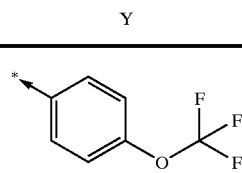 |
| 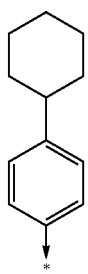 | 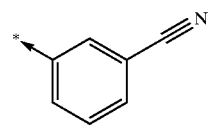 |
| 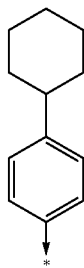 | 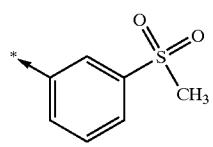 |
| 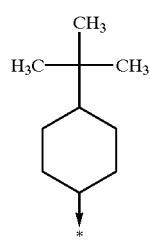 | 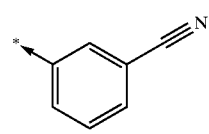 |
82
-continued
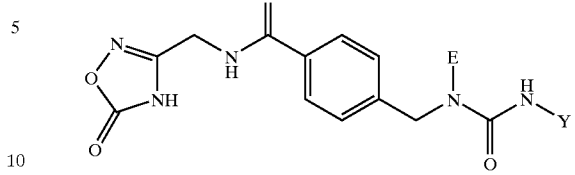
wherein
| E | Y |
|---|---|
| 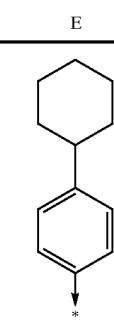 | 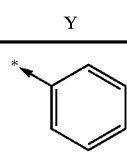 |
| 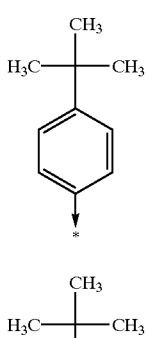 | 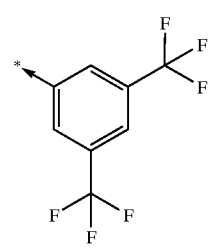 |
| 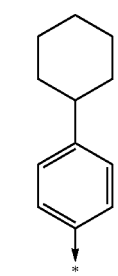 | 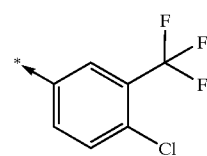 |
| 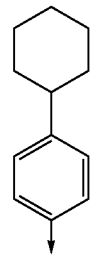 | 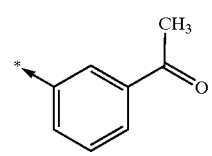 |

-continued

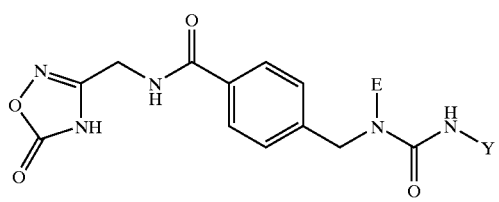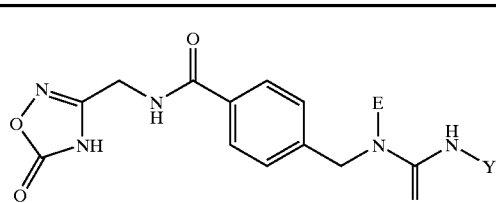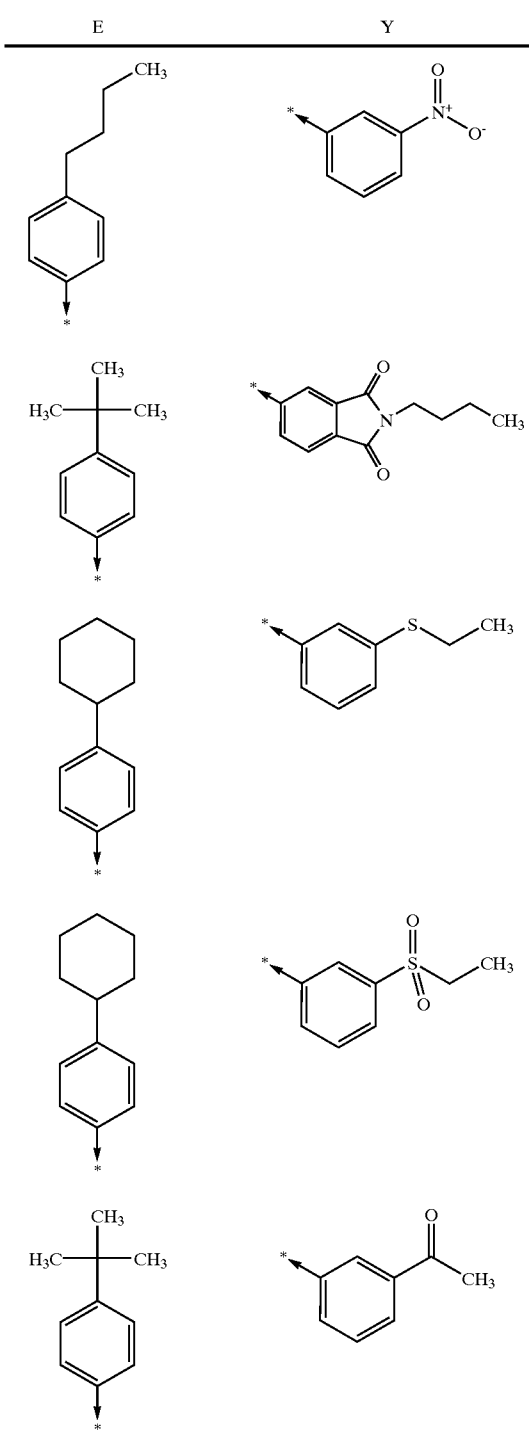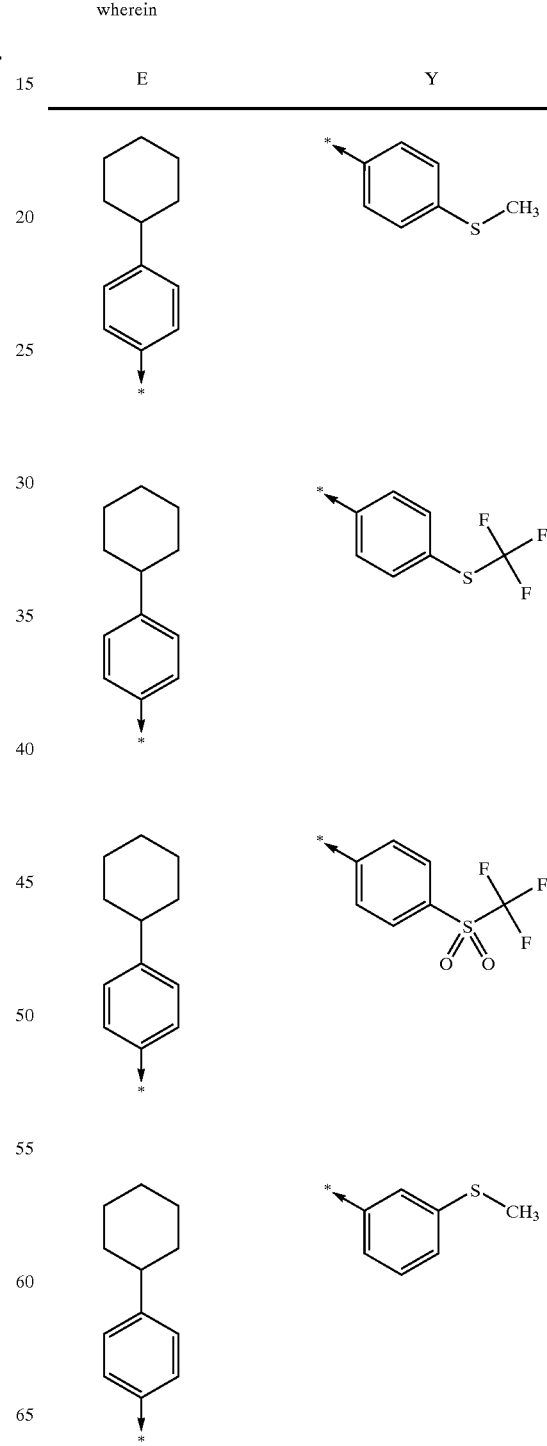

-continued wherein

| E | Y |
|---|---|

-continued
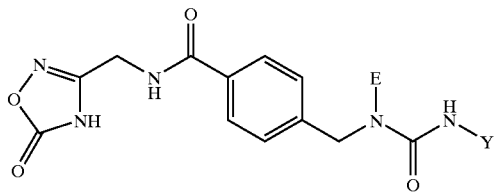
wherein
| E | Y |
|---|---|
| 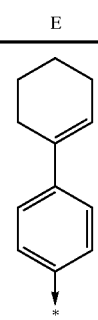 | 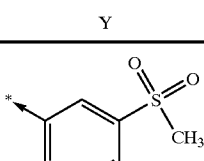 |
| 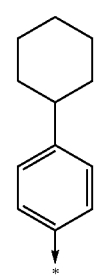 | 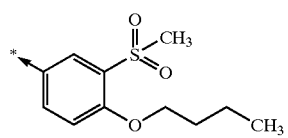 |
| 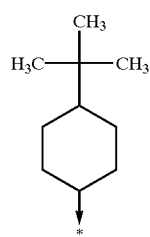 | 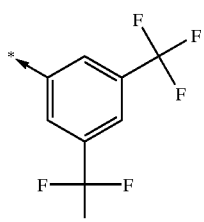 |
| 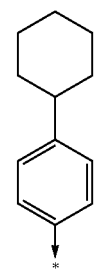 | 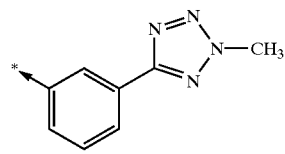 |
| 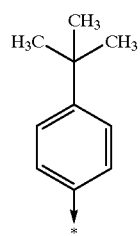 | 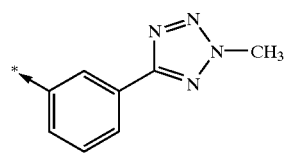 |
-continued
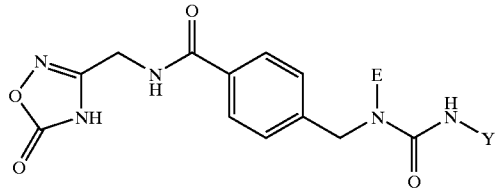
wherein
| E | Y |
|---|---|
| 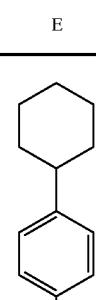 | 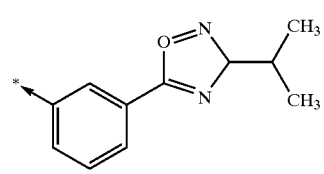 |
| 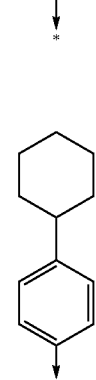 | 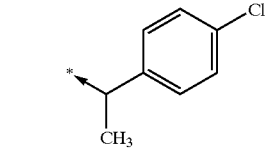 |
| 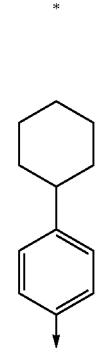 | 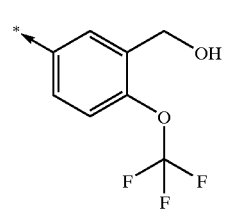 |
| 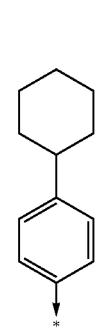 | 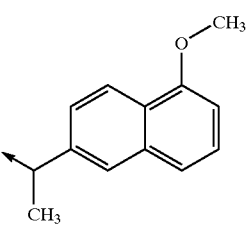 |

-continued

-continued

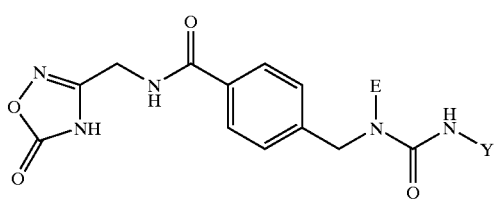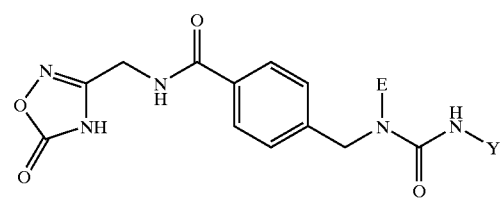

-continued wherein

| E | Y |
|---|---|
| 1-methyl-1-(4-cyclohexyl)ethyl (tert-butylcyclohexyl) | 3,5-bis(trifluoromethyl)phenyl |
| 4-cyclohexylphenyl | 3,4-dichlorophenyl |
| 4-cyclohexylphenyl | 4-(trifluoromethoxy)benzyl |
| 4-cyclohexylphenyl | 2-(trifluoromethoxy)benzyl |

-continued wherein

| E | Y |
|---|---|
| 4-cyclohexylphenyl | 2-(trifluoromethoxy)benzyl |
| 4-cyclohexylphenyl | 5-(methylsulfonyl)thien-2-yl |
| 4-(cyclohex-1-enyl)phenyl | 3-(trifluoromethoxy)phenyl |
| 4-(cyclohex-1-enyl)phenyl | 4-cyano-2-(trifluoromethyl)phenyl |

-continued

| E | Y |
|---|---|

-continued
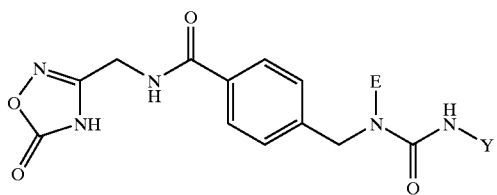
wherein
| E | Y |
|---|---|
| 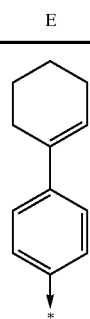 | 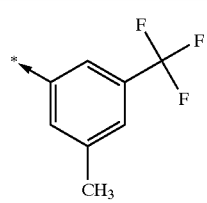 |
| 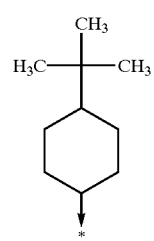 | 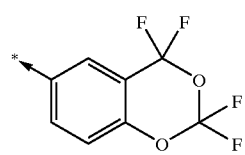 |
| 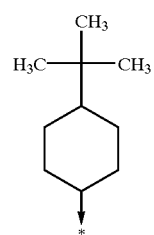 | 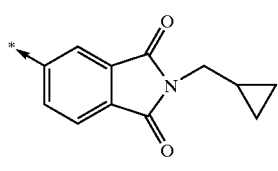 |
| 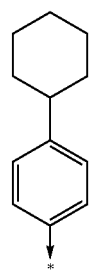 | 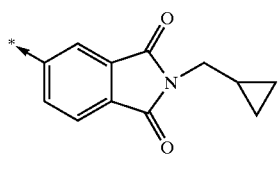 |
| 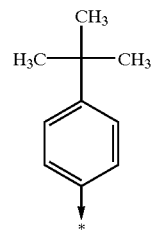 | 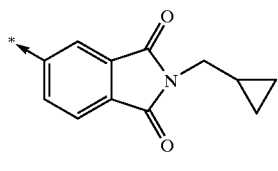 |
-continued
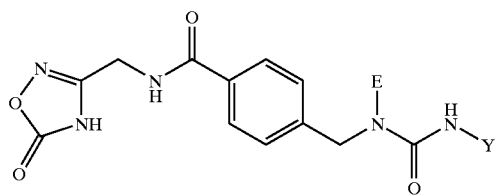
wherein
| E | Y |
|---|---|
| 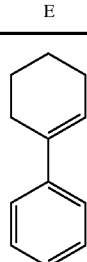 | 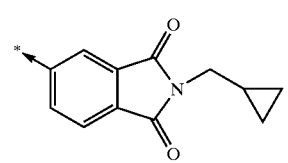 |
| 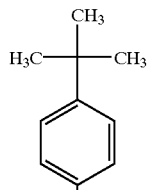 | 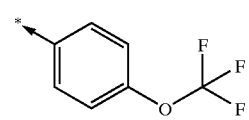 |
| 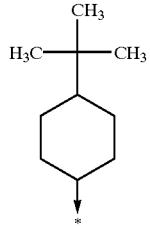 | 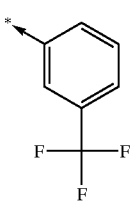 |
| 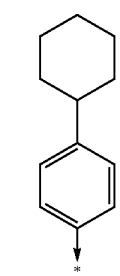 |  |
| 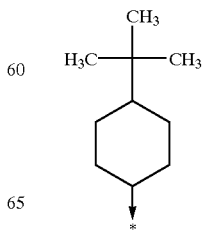 | |

| 103 | | 104 | |
|---|---|---|---|
| -continued | | -continued | |
| 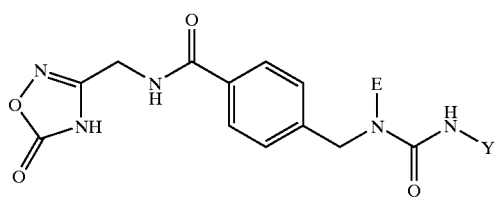 | | 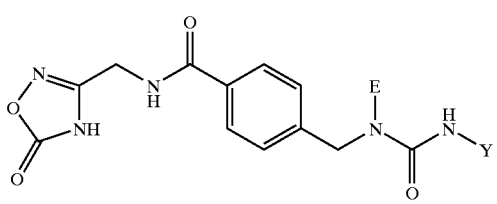 | |
| wherein | | wherein | |
| E | Y | E | Y |
| 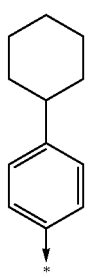 | 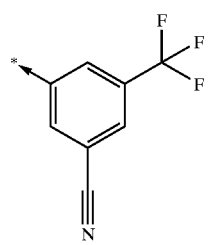 | 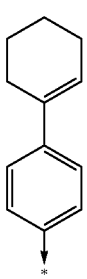 | 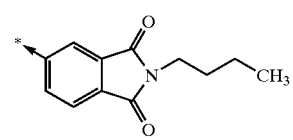 |
| 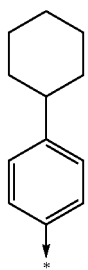 | 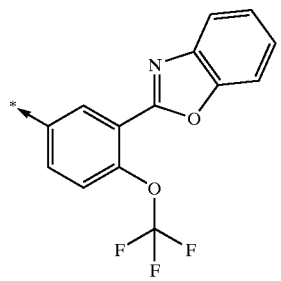 | 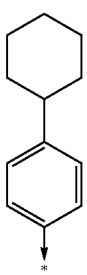 | 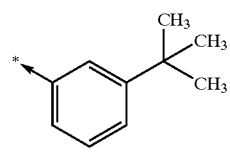 |
| 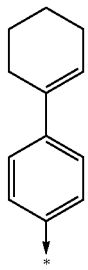 | 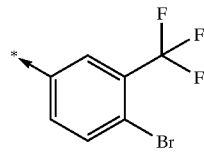 | 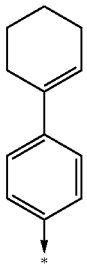 | 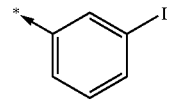 |
| 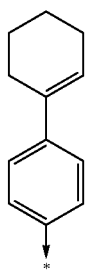 | 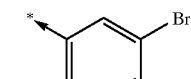 | 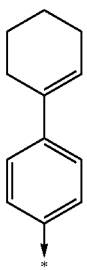 | 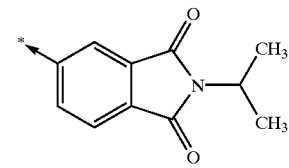 |

-continued
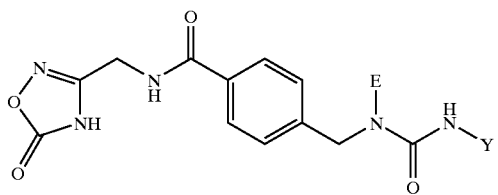
wherein
| E | Y |
|---|---|
| 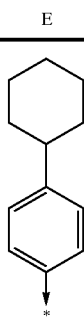 | 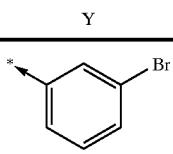 |
| 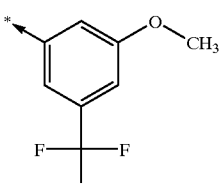 | 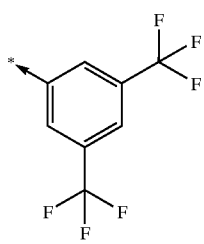 |
| 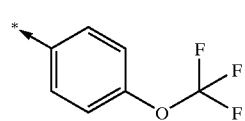 | 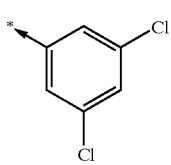 |
-continued
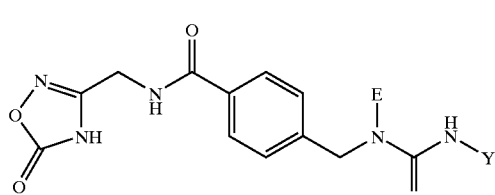
wherein
| E | Y |
|---|---|
| 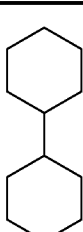 | 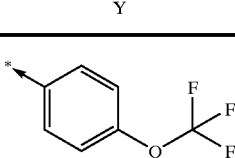 |
| 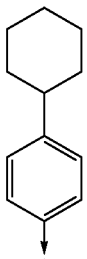 | 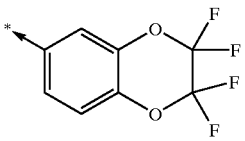 |
| 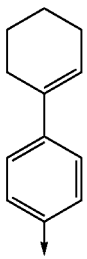 | 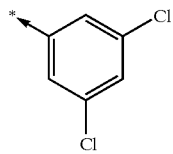 |
| 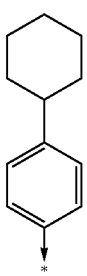 | 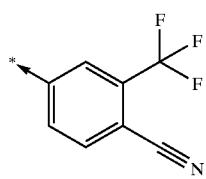 |

-continued

| E | Y |
|---|---|
| 4-cyclohexylphenyl | 1-phenylethyl |
| 4-cyclohexylphenyl | 4-(2-chloro-4-cyano)phenyl |
| 4-cyclohexyl-(4H-pyran) | 2-methyl-5-(N-ethyl-N-phenylsulfamoyl)phenyl |
| 4-cyclohexylphenyl | 3-chloro-4-bromophenyl |

-continued

| E | Y |
|---|---|
| 4-cyclohexylphenyl | N-cyclopropylphthalimidyl |
| 4-(cyclohex-1-enyl)phenyl | N-(2,2,2-trifluoroethyl)phthalimidyl |
| 4-cyclohexylphenyl | N-(2,2,2-trifluoroethyl)phthalimidyl |

Pharmacological Methods

In the following section binding assays as well as functional assays useful for evaluating the efficiency of the compounds of the invention are described.

Binding of compounds to the glucagon receptor may be determined in a competition binding assay using the cloned human glucagon receptor.

Antagonism may be determined as the ability of the compounds to inhibit the amount of cAMP formed in the presence of 5 nM glucagon.

Glucagon Binding Assay (I)

Receptor binding is assayed using cloned human receptor (Lok et al., Gene 140, 203–209 (1994)). The receptor inserted in the pLJ6' expression vector using EcoRI/SSt1 restriction sites (Lok et al.) is expressed in a baby hamster kidney cell line (A3 BHK 570–25). Clones are selected in the presence of 0.5 mg/ml G-418 and are shown to be stable for more than 40 passages. The $K_d$ is shown to be 0.1 nM.

Plasma membranes are prepared by growing cells to confluence, detaching them from the surface and resuspending the cells in cold buffer (10 mM tris/HCl, pH 7.4 containing 30 mM NaCl, 1 mM dithiothreitol, 5 mg/l leupeptin (Sigma), 5 mg/l pepstatin (Sigma), 100 mg/l bacitracin (Sigma) and 15 mg/l recombinant aprotinin (Novo Nordisk A/S)), homogenization by two 10-s bursts using a Polytron PT 10–35 homogenizer (Kinematica), and centrifugation upon a layer of 41 w/v % sucrose at 95.000×g for 75 min. The white band located between the two layers is diluted in buffer and centrifuged at 40.000×g for 45 min. The precipitate containing the plasma membranes is suspended in buffer and stored at $-80°$ C. until use.

Glucagon is iodinated according to the chloramine T method (Hunter and Greenwood, Nature 194, 495 (1962)) and purified using anion exchange chromatography (Jøorgensen et al., Hormone and Metab. Res. 4, 223–224 (1972). The specific activity is 460 $\mu Ci/\mu g$ on the day of iodination. Tracer is stored at $-18°$ C. in aliquots and are used immediately after thawing.

Binding assays are carried out in triplicate in filter microtiter plates (MADV N65, Millipore). The buffer used in this assay is 50 mM HEPES, 5 mM EGTA, 5 mM $MgCl_2$, 0.005% tween 20, pH 7.4. Glucagon is dissolved in 0.05 M HCl, added an equal amount (w/w) of human serum albim and freeze-dried. On the day of use, it is dissolved in water and diluted in buffer to the desired concentrations.

Test compounds are dissolved and diluted in DMSO. 140 $\mu l$ buffer, 25 $\mu l$ glucagon or buffer, and 10 $\mu l$ DMSO or test compound are added to each well. Tracer (50.000 cpm) is diluted in buffer and 25 $\mu l$ are added to each well. 1–4 $\mu g$ freshly thawed plasma membrane protein diluted in buffer is then added in aliquots of 25 $\mu l$ to each well. Plates are incubated at 30° C. for 2 hours. Non-specific binding is determined with 104 M of glucagon. Bound tracer and unbound tracer are then separated by vacuum filtration (Millipore vacuum manifold). The plates are washed with 2×100 $\mu l$ buffer/well. The plates are air dried for a couple of hours, whereupon the filters are separated from the plates using a Millipore Puncher. The filters are counted in a gamma counter.

Functional Assay (I)

The functional assay is carried out in 96 well microtiter plates (tissue culture plates, Nunc). The resulting buffer concentrations in the assay are 50 mM tris/HCl, 1 mM EGTA, 1.5 mM magnesium sulphate, 1.7 mM ATP, 20 $\mu M$ GTP, 2 mM IBMX, 0.02% tween-20 and 0.1% human serum albim. pH is 7.4. Glucagon and proposed antagonist are added in aliquots of 35 $\mu L$ diluted in 50 mM tris/HCl, 1 mM EGTA, 1.85 mM magnesium sulphate, 0.0222% tween-20 and 0.111% human serum albim, pH 7.4. 20 $\mu l$ of 50 mM tris/HCl, 1 mM EGTA, 1.5 mM magnesium sulphate, 11.8 mM ATP, 0.14 mM GTP, 14 mM IBMX and 0.1% human serum albim, pH 7.4 is added. GTP is dissolved immediately before the assay.

50 $\mu l$ containing 5 $\mu g$ of plasma membrane protein is added in a tris/HCl, EGTA, magnesium sulphate, human serum albumin buffer (the actual concentrations are dependent upon the concentration of protein in the stored plasma membranes).

The total assay volume is 140 $\mu l$. The plates are incubated for 2 hours at 37° C. with continuous shaking. Reaction is terminated by addition of 25 $\mu l$ 0.5 N HCl. CAMP is measured by the use of a scintillation proximity kit (Amersham).

Glucagon Binding Assay (II)

BHK (baby hamster kidney cell line) cells are transfected with the human glucagon receptor and a membrane preparation of the cells is prepared. Wheat Germ Agglutinin derivatized SPA beads containing a scintillant (WGA beads) (Amersham) bound the membranes. $^{125}$I-glucagon bound to human glucagon receptor in the membranes and excited the scintillant in the WGA beads to light emission. Glucagon or samples binding to the receptor competed with $^{125}$I-glucagon.

All steps in the membrane preparation are kept on ice or performed at 4° C. BHK cells are harvested and centrifuged. The pellet is resuspended in homogenisation buffer (25 mM HEPES, pH=7.4, 2.5 mM $CaCl_2$, 1.0 mM $MgCl_2$, 250 mg/l bacitracin, 0.1 mM Pefabloc), homogenised 2×10 sec using Polytron 10–35 homogenizer (Kinematica) and added the same amount of homogenisation buffer as used for resuspension. After centrifugation (15 min at 2000×g) the supernatant is transferred to cold centrifuge tubes and centrifuged for 45 min at 40.000×g. The pellet is resuspended in homogenisation buffer, homogenised 2×10 sec (Polytron) and additional homogenisation buffer is added. The suspension is centrifuged for 45 min at 40.000×g and the pellet is resuspended in resuspension buffer (25 mM HEPES, pH=7.4, 2.5 mM $CaCl_2$, 1.0 mM $MgCl_2$) and homogenised 2×10 sec. (Polytron). The protein concentration is normally around 1.75 mg/ml. Stabilisation buffer (25 mM HEPES, pH=7.4, 2.5 mM $CaCl_2$, 1.0 mM $MgCl_2$, 1% bovine serum albumin, 500 mg/l bacitracin, 2.5 M sucrose) is added and the membrane preparation is stored at $-80°$ C.

The glucagon binding assay is carried out in opti plates (Polystyrene Microplates, Packard). 50 $\mu l$ assay buffer (25 mM HEPES, pH=7.5, 2.5 mM $CaCl_2$, 1.0 mM $MgCl_2$, 0.003% Tween-20, 0.005% bacitracin, 0.05% sodium azide) and 5 $\mu l$ glucagon or test compound (in DMSO) are added to each well. 50 $\mu l$ tracer ($^{125}$I-porcine glucagon, 50.000 cpm) and 50 $\mu l$ membranes (7.5 $\mu g$) containing the human glucagon receptor are then added to the wells. Finally 50 $\mu l$ WGA beads containing 1 mg beads are transferred to the well. The plates are incubated for 4 hours on a shaker and then settled for 8–48 hours. The opti plates are counted in a Topcounter. Non-specific binding is determined with 500 nM of glucagon.

Most of the compounds according to the examples showed $IC_{50}$ values below 500 nM.

GIP Binding Assay

BHK (baby hamster kidney cell line) cells are transfected with the human GIP receptor and a membrane preparation of the cells is prepared. Wheat Germ Agglutinin derivatized SPA beads containing a scintillant (WGA beads) (Amersham) bound the membranes. $^{125}$I-GIP bound to human GIP receptor in the membranes and excited the scintillant in the WGA beads to light emission. GIP or samples binding to the receptor competed with $^{125}$I-GIP.

All steps in the membrane preparation are kept on ice or performed at 4° C. BHK cells are harvested and centrifuged. The pellet is resuspended in homogenisation buffer (25 mM HEPES, pH=7.4, 2.5 mM $CaCl_2$, 1.0 mM $MgCl_2$, 250 mg/l bacitracin, 0.1 mM Pefabloc), homogenised 2×10 sec using Polytron 10–35 homogenizer (Kinematica) and added the same amount of homogenisation buffer as used for resuspension. After centrifugation (15 min at 2000×g) the supematant is transferred to cold centrifuge tubes and centrifuged for 45 min at 40.000×g. The pellet is resuspended in homogenisation buffer, homogenised 2×10 sec (Polytron) and additional homogenisation buffer is added. The suspension is centrifuged for 45 min at 40.000×g and the pellet is resuspended in resuspension buffer (25 mM HEPES, pH=7.4, 2.5 mM CaCl$_2$, 1.0 mM MgCl$_2$) and homogenised 2×10 sec. (Polytron). The protein concentration is normally around 1.75 mg/ml. Stabilisation buffer (25 mM HEPES, pH=7.4, 2.5 mM CaCl$_2$, 1.0 mM MgCl$_2$, 1% bovine serum albumin, 500 mg/l bacitracin, 2.5 M sucrose) is added and the membrane preparation is stored at −80° C.

The GIP binding assay is carried out in opti plates (Polystyrene Microplates, Packard). 50 μl assay buffer (25 mM HEPES, pH=7.5, 2.5 mM CaCl$_2$, 1.0 mM MgCl$_2$, 0.003% Tween-20, 0.005% bacitracin, 0.05% sodium azide) and 5 μl GIP or test compound (in DMSO) are added to each well. 50 μl tracer ($^{125}$I-porcine GIP, 50.000 cpm) and 50 μl membranes (20 μg) containing the human GIP receptor are then added to the wells. Finally 50 μl WGA beads containing 1 mg beads are transferred to the well. The plates are incubated for 3.5 hours on a shaker and then settled for 8–48 hours. The opti plates are counted in a Topcounter. Non-specific binding is determined with 500 nM of GIP.

Generally, the compounds show a higher affinity for the glucagon receptor compared to the GIP receptor.

What is claimed is:

1. A compound of formula (I):

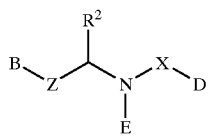

(I)

wherein $R^2$ is hydrogen or $C_{1-6}$-alkyl,

B is

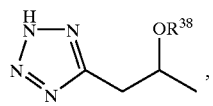

$R^{38}$ is hydrogen, —S(=O)$_2$—$C_{1-6}$-alkyl or —C(=O)—$C_{1-6}$-alkyl,

Z is arylene which may optionally be substituted with one or two groups $R^7$ and $R^8$ selected from halogen, —CN, —CF$_3$, —OCF$_3$, —NO$_2$, —OR$^9$, —NR$^9$R$^{10}$ and $C_{1-6}$-alkyl, wherein $R^9$ and $R^{10}$ independently are hydrogen or $C_{1-6}$-alkyl, X is

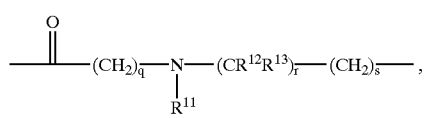

wherein r is 0 or 1, q and s independently are 0, 1, 2 or 3, $R^{11}$, $R^{12}$, and $R^{13}$ independently are hydrogen or $C_{1-6}$-alkyl, D is

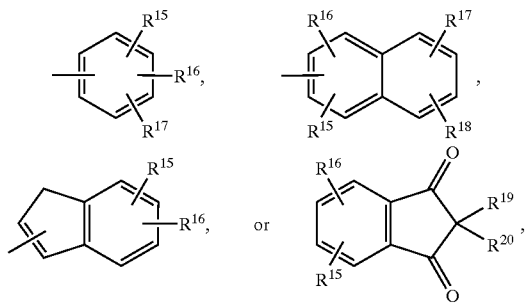

wherein $R^{15}$, $R^{16}$, $R^{17}$ and $R^{18}$ independently are hydrogen, halogen, —CN, —CH$_2$CN, —CHF$_2$, —CF$_3$, —OCF$_3$, —OCHF$_2$, —OCH$_2$CF$_3$, —OCF$_2$CHF$_2$, —S(O)$_2$CF$_3$, —SCF$_3$, —NO$_2$, —OR$^{21}$, —NR$^{21}$R$^{22}$, —SR$^{21}$, —NR$^{21}$S(O)$_2$R$^{22}$, —S(O)NR$^{21}$R$^{22}$, —S(O)R$^{21}$, —S(O)$_2$R$^{21}$, —C(O)NR$^{21}$R$^{22}$, —OC(O)NR$^{21}$R$^{22}$, —NR$^{21}$C(O)R$^{22}$, —CH$_2$C(O)NR$^{21}$R$^{22}$, —OCH$_2$C(O)NR$^{21}$R$^{22}$, —CH$_2$OR$^{21}$, —CH$_2$NR$^{21}$R$^{22}$, —OC(O)R$^{21}$ or —C(O)OR$^{21}$, $C_{1-6}$-alkyl, $C_{2-6}$-alkenyl or $C_{2-6}$-alkynyl, which may optionally be substituted with one or more substituents selected from halogen, —CN, —CF$_3$, —OCF$_3$, —NO$_2$, —OR$^{21}$, —NR$^{21}$R$^{22}$ and $C_{1-6}$-alkyl, $C_{3-8}$-cycloalkyl, $C_{4-8}$-cycloalkenyl, heterocyclyl, $C_{3-8}$-cycloalkyl-$C_{1-6}$-alkyl, $C_{3-8}$-cycloalkyl-$C_{1-6}$-alkoxy, $C_{3-8}$-cycloalkyloxy, $C_{3-8}$-cycloalkyl-$C_{1-6}$-alkylthio, $C_{3-8}$-cycloalkylthio, $C_{3-8}$-cycloalkyl-$C_{2-6}$-alkenyl, $C_{3-8}$-cycloalkyl-$C_{2-6}$-alkynyl, $C_{4-8}$-cycloalkenyl-$C_{1-6}$-alkyl, $C_{4-8}$-cycloalkenyl-$C_{2-6}$-alkenyl, $C_{4-8}$-cycloalkenyl-$C_{2-6}$-alkynyl, heterocyclyl-$C_{1-6}$-alkyl, heterocyclyl-$C_{2-6}$-alkenyl, heterocyclyl-$C_{2-6}$-alkynyl, aryl, aryloxy, aryloxycarbonyl, aroyl, aryl-$C_{1-6}$-alkoxy, aryl-$C_{1-6}$-alkyl, aryl-$C_{2-6}$-alkenyl, aryl-$C_{2-6}$-alkynyl, heteroaryl, heteroaryl-$C_{1-6}$-alkyl, heteroaryl-$C_{2-6}$-alkenyl or heteroaryl-$C_{2-6}$-alkynyl, of which the cyclic moieties optionally may be substituted with one or more substituents selected from halogen, —CN, —CF$_3$, —OCF$_3$, —NO$_2$, —OR$^{21}$, —NR$^{21}$R$^{22}$ and $C_{1-6}$-alkyl, wherein $R^{21}$ and $R^{22}$ independently are hydrogen, $C_{1-6}$-alkyl or aryl, or two of the groups $R^{15}$ to $R^{18}$ when placed in adjacent positions together may form a bridge —(CR$^{23}$R$^{24}$)$_a$—O—(CR$^{25}$R$^{26}$)$_c$—O—, wherein a is 0, 1 or 2, c is 1 or 2, $R^{23}$, $R^{24}$, $R^{25}$ and $R^{26}$ independently are hydrogen, $C_{1-6}$-alkyl or fluorine, $R^{19}$ and $R^{20}$ independently are hydrogen, $C_{1-6}$-alkyl, $C_{3-8}$-cycloalkyl or $C_{3-8}$-cycloalkyl-$C_{1-6}$-alkyl, E is

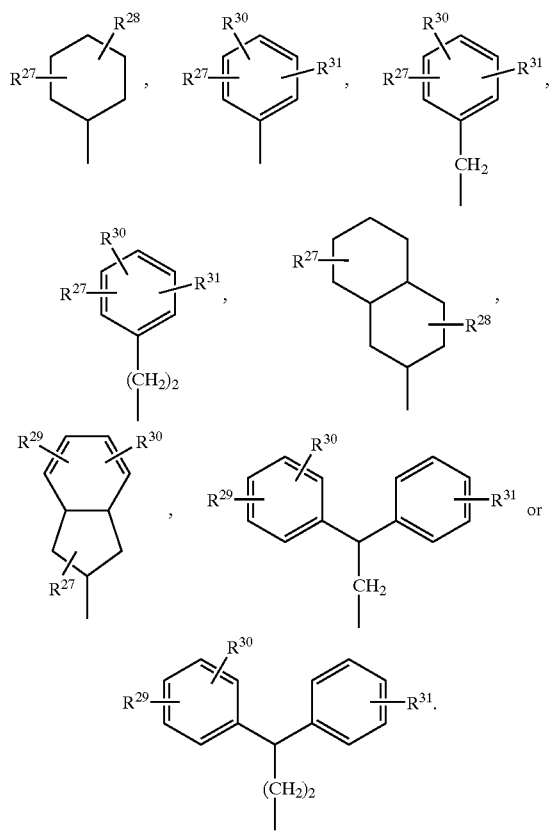

wherein
R²⁷ and R²⁸ independently are
hydrogen, halogen, —CN, —CF₃, —OCF₃, —OR³²,
—NR³²R³³, C₁₋₆-alkyl, C₃₋₆-cycloalkyl, C₄₋₈-cycloalkenyl or aryl,
wherein the aryl group optionally may be substituted with one or more substituents selected from halogen, —CN, —CF₃, —OCF₃, —NO₂, —OR³², —NR³²R³³ and C₁₋₆-alkyl,
wherein
R³² and R³³ independently are hydrogen or C₁₋₆-alkyl,
R²⁹, R³⁰ and R³¹ independently are
hydrogen, halogen, —CHF₂, —CF₃, —OCF₃, —OCHF₂, —OCH₂CF₃, —OCF₂CHF₂, —SCF₃, —OR³⁴, —NR³⁴R³⁵, —SR³⁴, —S(O)R³⁴, —S(O)₂R³⁴, —C(O)NR³⁴R³⁵, —OC(O)NR³⁴R³⁵, —NR³⁴C(O)R³⁵, —OCH₂C(O)NR³⁴R³⁵, —C(O)R³⁴ or —C(O)OR³⁴,
C₁₋₆-alkyl, C₂₋₆-alkenyl or C₂₋₆-alkynyl,
which may optionally be substituted with one or more substituents selected from halogen, —CN, —CF₃, —OCF₃, —NO₂, —OR³⁴, —NR³⁴R³⁵ and C₁₋₆-alkyl,
C₃₋₈-cycloalkyl, C₄₋₈-cycloalkenyl, heterocyclyl, C₃₋₈-cycloalkyl-C₁₋₆-alkyl, C₃₋₈-cycloalkyl-C₂₋₆-alkenyl, C₃₋₈-cycloalkyl-C₂₋₆-alkynyl, C₄₋₈-cycloalkenyl-C₁₋₆-alkyl, C₄₋₈-cycloalkenyl-C₂₋₆-alkenyl, C₄₋₈-cycloalkenyl-C₂₋₆-alkynyl, heterocyclyl-C₁₋₆-alkyl, heterocyclyl-C₂₋₆-alkenyl, heterocyclyl-C₂₋₆-alkynyl, aryl, aryloxy, aroyl, aryl-C₁₋₆-alkoxy, aryl-C₁₋₆-alkyl, aryl-C₂₋₆-alkenyl, aryl-C₂₋₆-alkynyl, heteroaryl, heteroaryl-C₁₋₆-alkyl, heteroaryl-C₂₋₆-alkenyl or heteroaryl-C₂₋₆-alkynyl, of which the cyclic moieties optionally may be substituted with one or more substituents selected from halogen, —CN, —CF₃, —OCF₃, —NO₂, —OR³⁴, —NR³⁴R³⁵ and C₁₋₆-alkyl,
wherein R³⁴ and R³⁵ independently are hydrogen, C₁₋₆-alkyl or aryl,
or two of the groups R²⁹, R³⁰ and R³¹ when attached to the same ring carbon atom or different ring carbon atoms together may form a radical —O—(CH₂)ₜ—CR³⁶R³⁷—(CH₂)ₗ—O—, —(CH₂)ₜ—CR³⁶R³⁷—(CH₂)ₗ— or —S—(CH₂)ₜ—CR³⁶R³⁷—(CH₂)ₗ—S—,
wherein
t and l independently are 0, 1, 2, 3, 4 or 5,
R³⁶ and R³⁷ independently are hydrogen or C₁₋₆-alkyl,
as well as any optical or geometric isomer or tautomeric form thereof and mixtures thereof or a pharmaceutically acceptable salt thereof.

2. A compound according to claim 1, wherein E is

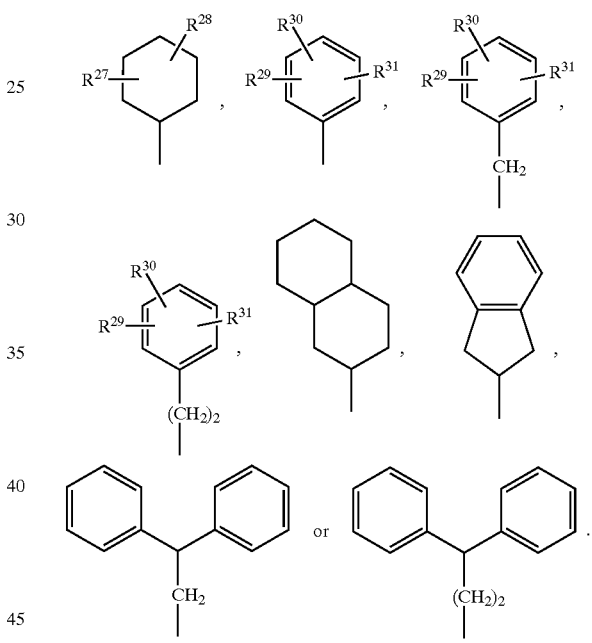

3. A compound according to claim 1, wherein E is

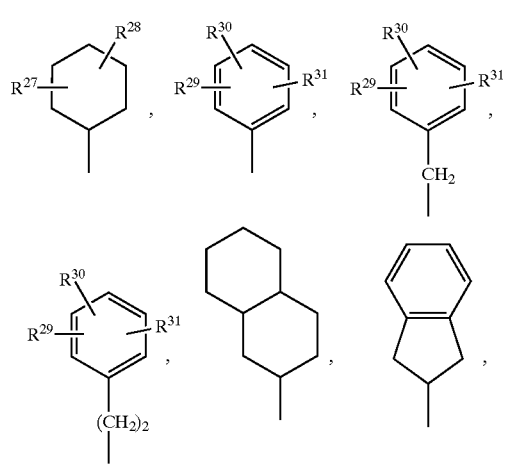

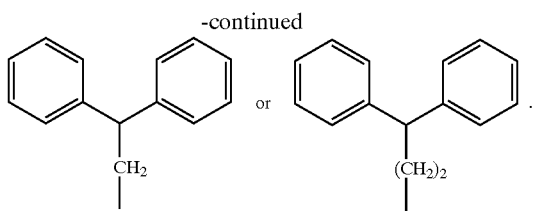

wherein $R^{27}$, $R^{28}$, $R^{29}$, $R^{30}$ and $R^{31}$ are as defined in claim 1.

4. A compound according to claim 3, wherein E is

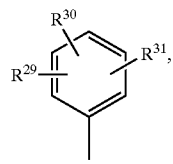

wherein $R^{29}$, $R^{30}$ and $R^{31}$ are as defined in claim 1.

5. A compound according to claim 4, wherein $R^{29}$, $R^{30}$ and $R^{31}$ independently are hydrogen, —CHF$_2$, —CF$_3$, —OCF$_3$, —OCHF$_2$, —OCH$_2$CF$_3$, —OCF$_2$CHF$_2$, —SCF$_3$, —OR$^{34}$, —NR$^{34}$R$^{35}$, —SR$^{34}$, —S(O)R$^{34}$, —S(O)$_2$R$^{34}$, —C(O)NR$^{34}$R$^{35}$, —OC(O)NR$^{34}$R$^{35}$, —NR$^{34}$C(O)R$^{35}$, —OCH$_2$C(O)NR$^{34}$R$^{35}$, —C(O)R$^{34}$ or —C(O)OR$^{34}$, C$_{1-6}$-alkyl, C$_{2-6}$-alkenyl or C$_{2-6}$-alkynyl,
which may optionally be substituted with one or more substituents selected from halogen, —CN, —CF$_3$, —OCF$_3$, —NO$_2$, —OR$^{34}$, —NR$^{34}$R$^{35}$ and C$_{1-6}$-alkyl, C$_{3-8}$-cycloalkyl or C$_{4-8}$-cycloalkenyl,
which may optionally be substituted with one or more substituents selected from halogen, —CN, —CF$_3$, —OCF$_3$, —NO$_2$, —OR$^{34}$, —NR$^{34}$R$^{35}$ and C$_{1-6}$-alkyl,
wherein $R^{34}$ and $R^{35}$ independently are hydrogen, C$_{1-6}$-alkyl or aryl,
or $R^{34}$ and $R^{35}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds.

6. A compound according to claim 5, wherein $R^{29}$, $R^{30}$ and $R^{31}$ independently are hydrogen, C$_{1-6}$-alkoxy, —CF$_3$, —OCF$_3$ or —NR$^{34}$R$^{35}$, wherein $R^{34}$ and $R^{35}$ are as defined in claim 1, or p1 C$_{1-6}$-alkyl, C$_{3-8}$-cycloalkyl or C$_{4-8}$-cycloalkenyl, which are optionally substituted as defined in claim 1.

7. A compound according to claim 1 of the general formula (Id):

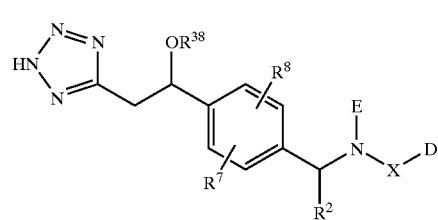

wherein $R^2$, $R^7$, $R^8$, $R^{38}$, X, D and E are as defined in claim 1 or in any one of the preceding claims.

8. A compound according to claim 3, wherein E is

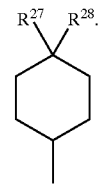

9. A compound according to claim 3, wherein E is

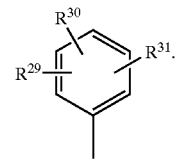

10. A compound according to claim 4, wherein E is

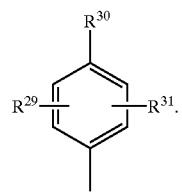

11. A compound according to claim 4, wherein $R^{29}$, $R^{30}$ and $R^{31}$ independently are hydrogen, —CHF$_2$, —CF$_3$, —OCF$_3$, —OCHF$_2$, —OCH$_2$CF$_3$, —OCF$_2$CHF$_2$, —SCF$_3$, —OR$^{34}$, —NR$^{34}$R$^{35}$, —SR$^{34}$, —S(O)R$^{34}$, —S(O)$_2$R$^{34}$, —C(O)NR$^{34}$R$^{35}$, —OC(O)NR$^{34}$R$^{35}$, —NR$^{34}$C(O)R$^{35}$, —OCH$_2$C(O)NR$^{34}$R$^{35}$, —C(O)R$^{34}$ or —C(O)OR$^{34}$, C$_{1-6}$-alkyl, C$_{2-6}$-alkenyl or C$_{2-6}$-alkynyl,
which may optionally be substituted with one or more substituents selected from halogen, —CN, —CF$_3$, —OCF$_3$, —NO$_2$, —OR$^{34}$, —NR$^{34}$R$^{35}$ and C$_{1-6}$-alkyl, C$_{3-8}$-cycloalkyl or C$_{4-8}$-cycloalkenyl,
which may optionally be substituted with one or more substituents selected from halogen, —CN, —CF$_3$, —OCF$_3$, —NO$_2$, —OR$^{34}$, —NR$^{34}$R$^{35}$ and C$_{1-6}$-alkyl,
wherein $R^{34}$ and $R^{35}$ independently are hydrogen, C$_{1-6}$-alkyl or aryl.

12. A compound according to claim 6, wherein $R^{29}$, $R^{30}$ and $R^{31}$ independently are
hydrogen or
C$_{1-6}$-alkyl, C$_{3-8}$-cycloalkyl or C$_{4-8}$-cycloalkenyl, which are optionally substituted.

13. A compound according to claim 1 of formula (Id):

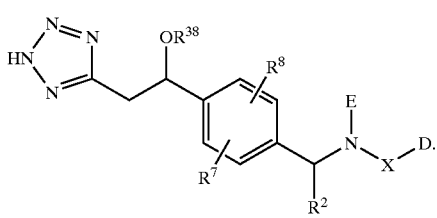

(Id)

14. A compound according to claim 7, wherein $R^2$, $R^7$ and $R^8$ are hydrogen.

15. A compound according to claim 13, wherein $R^{15}$, $R^{16}$ and $R^{17}$ independently are hydrogen, halogen, —CN, —NO$_2$, —CF$_3$, —OCF$_3$, —SCF$_3$, $C_{1\text{-}6}$-alkyl, $C_{1\text{-}6}$-alkoxy, —S—$C_{1\text{-}6}$-alkyl, —C(O)OR$^{21}$, —C(O)R$^2$, —CH$_2$OR$^{21}$, —C(O)NR$^{21}$R$^{22}$, —S(O)$_2$R$^{21}$, —S(O)$_2$CF$_3$, —S(O)$_2$NR$^{21}$R$^{22}$, $C_{3\text{-}8}$-cycloalkyl or aryl, or two of the groups $R^{15}$, $R^{16}$ and $R^{17}$ when placed in adjacent positions together form a bridge —(CR$^{23}$R$^{24}$)$_a$—O—(CR$^{25}$R$^{26}$)$_c$—O—, wherein $R^{21}$ and $R^{22}$ independently are hydrogen or $C_{1\text{-}6}$-alkyl, and a, c, $R^{23}$, $R^{24}$, $R^{25}$ and $R^{26}$ are as defined in claim 1.

16. A compound according to claim 15, wherein $R^{15}$, $R^{16}$ and $R^{17}$ independently are hydrogen, —S—$C_{1\text{-}6}$-alkyl, halogen, —CN, —CF$_3$, —OCF$_3$ or $C_{1\text{-}6}$-alkoxy, or wherein two of the substituents in adjacent positions form the bridge —CF$_2$—O—CF$_2$—O—.

17. A compound according to claim 16, wherein $R^{15}$, $R^{16}$ an $R^{17}$ independently are hydrogen, halogen, —S—CH$_3$, —CF$_3$ or —OCF$_3$, or wherein two of the substituents in adjacent positions form the bridge —CF$_2$—O—CF$_2$—O—.

18. A compound according to claim 3, wherein E is

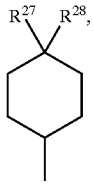

wherein $R^{27}$ and $R^{28}$ are as defined in claim 1.

19. A compound according to claim 3, wherein $R^{27}$ and $R^{28}$ independently are hydrogen, $C_{1\text{-}6}$-alkyl, $C_{3\text{-}8}$-cycloalkyl, $C_{4\text{-}8}$-cycloalkenyl or phenyl.

20. A compound according to claim 19, wherein $R^{27}$ is hydrogen and $R^{28}$ is $C_{1\text{-}6}$-alkyl, $C_{4\text{-}8}$-cycloalkenyl or $C_{3\text{-}8}$-cycloalkyl.

21. A compound according to claim 4, wherein E is

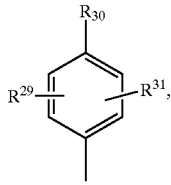

wherein $R^{29}$, $R^{30}$ and $R^{31}$ are as defined in claim 1.

22. A compound according to claim 6, wherein $R^{29}$, $R^{30}$ and $R^{31}$ independently are
hydrogen or
$C_{1\text{-}6}$-alkyl, $C_{3\text{-}8}$-cycloalkyl or $C_{4\text{-}8}$-cycloalkenyl, which are optionally substituted as defined in claim 1.

23. A compound according to claim 22, wherein $R^{29}$, $R^{30}$ and $R^{31}$ independently are hydrogen, $C_{1\text{-}6}$-alkyl, $C_{3\text{-}8}$-cycloalkyl or $C_{4\text{-}8}$-cycloalkenyl.

24. A compound according to claim 23, wherein $R^{29}$ and $R^{31}$ are both hydrogen and $R^{30}$ is $C_{1\text{-}6}$-alkyl, $C_{3\text{-}8}$-cycloalkyl or $C_{4\text{-}8}$-cycloalkenyl.

25. A compound according to claim 24, wherein $R^{29}$ and $R^{31}$ are both hydrogen and $R^{30}$ is $C_{1\text{-}6}$-alkyl.

26. A compound according to claim 1, wherein said compound has an IC$_{50}$ value of no greater than 5 μM as determined by Glucagon Binding Assay (I) or Glucagon Binding Assay (II).

27. A compound according to claim 26, wherein said compound has an IC$_{50}$ value of less than 1 μM as determined by Glucagon Binding Assay (I) or Glucagon Binding Assay (II).

28. A compound according to claim 1, wherein said compound is an agent useful for the treatment and/or prevention of an indication selected from the group consisting of hyperglycemia, impaired glucose tolerance, Type 2 diabetes, Type 1 diabetes and obesity.

29. A pharmaceutical composition comprising at least one compound according to claim 1 together with one or more pharmaceutically acceptable carriers or excipients.

30. A pharmaceutical composition according to claim 29, in unit dosage form, said composition comprising from about 0.05 mg to about 1000 mg of the compound according to claim 1.

31. A method for the treatment of glucagon-mediated disorders and diseases, said method comprising administering to a subject in need thereof an effective amount of a compound according to claim 1.

32. The method according to claim 31, wherein the effective amount of the compound is in the range of from about 0.05 mg to about 2000 mg per day.

33. The method according to claim 31, wherein the effective amount of the compound is in the range of from about 0.1 mg to about 1000 mg per day.

34. The method according to claim 31, wherein the effective amount of the compound is in the range of from about 0.5 mg to about 500 mg per day.

35. A method for the treatment of hyperglycemia, said method comprising administering to a subject in need thereof an effective amount of a compound according to claim 1.

36. A method for lowering blood glucose in a mammal, said method comprising administering to said mammal in need thereof an effective amount of a compound according to claim 1.

37. A method for the treatment of impaired glucose tolerance, said method comprising administering to a subject in need thereof an effective amount of a compound according to claim 1.

38. A method for the treatment of Type 2 diabetes, said method comprising administering to a subject in need thereof an effective amount of a compound according to claim 1.

39. A method for delaying the progression from impaired glucose tolerance to Type 2 diabetes, said method comprising administering to a subject in need thereof an effective amount of a compound according to claim 1.

40. A method for delaying the progression from non-insulin requiring Type 2 diabetes to insulin requiring Type 2 diabetes, said method comprising administering to a subject in need thereof an effective amount of a compound according to claim 1.

41. The method according to claim 31, said method further comprising administering to said subject an antidiabetic agent.

42. The method according to claim 31, said method further comprising administering to said subject an antiobesity agent.

43. The method according to claim 31, said method further comprising administering to said subject an antihypertensive agent.

44. A pharmaceutical composition according to claim 29, in unit dosage form, said composition comprising from about 0.1 mg to about 500 mg of the compound according to claim 1.

45. A pharmaceutical composition according to claim 29, in unit dosage form, said composition comprising from about 0.5 mg to about 200 mg of the compound according to claim 1.

46. A compound according to claim 26, wherein said compound has an $IC_{50}$ value of less than 500 nM as determined by Glucagon Binding Assay (I) or Glucagon Binding Assay (II).

47. A compound according to claim 26, wherein said compound has an $IC_{50}$ value of less than 100 nM as determined by Glucagon Binding Assay (I) or Glucagon Binding Assay (II).

48. A compound according to claim 1, wherein Z is

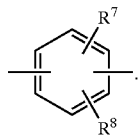

49. A compound according to claim 1, wherein X is

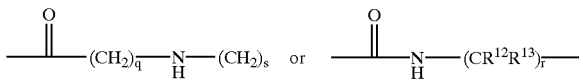

wherein q is 0 or 1, r is 0 or 1, s is 0, 1 or 2, and $R^{12}$ and $R^{13}$ independently are hydrogen or $C_{1-6}$-alkyl.

50. A compound according to claim 10, wherein X is —C(O)NH—, —C(O)NHCH$_2$—, or —C(O)NHCH$_2$CH$_2$—.

51. A compound according to claim 11, wherein X is —C(O)NH—.

52. A compound according to claim 1, wherein D is

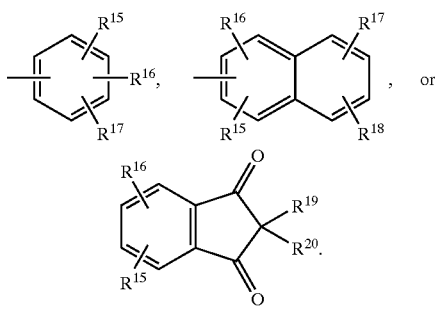

53. A compound according to claim 13, wherein D is

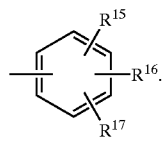

54. A compound according to claim 13, wherein $R^{15}$, $R^{16}$ and $R^{17}$ independently are hydrogen, halogen, —CN, —NO$_2$, —CF$_3$, —OCF$_3$, —SCF$_3$, $C_{1-6}$-alkyl, $C_{1-6}$-alkoxy, —S—$C_{1-6}$-alkyl, —C(O)OR$^{21}$, —C(O)R$^{21}$, —CH$_2$OR$^{21}$, —C(O)NR$^{21}$R$^{22}$, —S(O)$_2$R$^{21}$, —S(O)$_2$CF$_3$, —S(O)$_2$NR$^{21}$R$^{22}$, $C_{3-8}$-cycloalkyl or aryl, or two of the groups $R^{15}$, $R^{16}$ and $R^{17}$ when placed in adjacent positions together form a bridge —(CR$^{23}$R$^{24}$)$_a$—O—(CR$^{25}$R$^{26}$)$_c$—O— wherein $R^{21}$ and $R^{22}$ independently are hydrogen or $C_{1-6}$-alkyl.

55. A compound according to claim 5, wherein $R^{29}$, $R^{30}$ and $R^{31}$ independently are Hydrogen, $C_{1-6}$-alkoxy, —CF$_3$, —OCF$_3$ or NR$^{34}$R$^{35}$, or $C_{1-6}$-alkyl, $C_{3-8}$-cycloalkyl or $C_{4-8}$-cycloalkenyl, which are optionally substituted.

* * * * *